US012648581B2

(12) United States Patent
Bernardeau et al.

(10) Patent No.: US 12,648,581 B2
(45) Date of Patent: Jun. 9, 2026

(54) FEED COMPOSITIONS FOR ANIMAL HEALTH

(71) Applicant: INTERNATIONAL N&H DENMARK APS, Kongens Lyngby (DK)

(72) Inventors: Marion Bernardeau, Caen (FR); Qiong Cheng, Wilmington, DE (US); Raymond E. Jackson, Newark, DE (US); Jian Ping Lai, Wallingford, PA (US); Yang-Xiang Li, Newark, DE (US); Wenting Li, Marlborough (GB); Charlotte Horsmans Poulsen, Braband (DK); Yixin Ren, Palo Alto, CA (US); Luan Tao, Wallingford, PA (US); Qiong Wang, Palo Alto, CA (US); Derek Joseph Zimmer, Blackwood, NJ (US); Susan Hennessey, Rochester, NY (US)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 720 days.

(21) Appl. No.: 17/797,665

(22) PCT Filed: Feb. 5, 2021

(86) PCT No.: PCT/US2021/016837
§ 371 (c)(1),
(2) Date: Aug. 4, 2022

(87) PCT Pub. No.: WO2021/158927
PCT Pub. Date: Aug. 12, 2021

(65) Prior Publication Data
US 2023/0138517 A1     May 4, 2023

Related U.S. Application Data

(60) Provisional application No. 63/082,634, filed on Sep. 24, 2020, provisional application No. 62/971,503, filed on Feb. 7, 2020.

(51) Int. Cl.
| | |
|---|---|
| *A23K 10/18* | (2016.01) |
| *A23K 10/30* | (2016.01) |
| *A23K 20/189* | (2016.01) |
| *A23K 50/10* | (2016.01) |
| *C12N 1/205* | (2026.01) |
| *C12R 1/01* | (2006.01) |

(52) U.S. Cl.
CPC .............. *A23K 10/18* (2016.05); *A23K 10/30* (2016.05); *A23K 20/189* (2016.05); *A23K 50/10* (2016.05); *C12N 1/205* (2021.05); *C12R 2001/01* (2021.05)

(58) Field of Classification Search
None
See application file for complete search history.

(56) References Cited

U.S. PATENT DOCUMENTS

| | | | |
|---|---|---|---|
| 6,287,841 | B1 | 9/2001 | Mulleners et al. |
| 7,754,469 | B2 | 7/2010 | Baltzley et al. |
| 2008/0263688 | A1 | 10/2008 | Lassen et al. |
| 2017/0354697 | A1 | 12/2017 | Schneider et al. |
| 2019/0358272 | A1* | 11/2019 | Laldas ................... A23K 50/10 |

FOREIGN PATENT DOCUMENTS

| | | | |
|---|---|---|---|
| CN | 1681522 | A | 10/2005 |
| CN | 110475479 | A | 11/2019 |
| WO | WO8906270 | A1 | 7/1989 |
| WO | WO1992012645 | A1 | 8/1992 |
| WO | WO9219729 | A1 | 11/1992 |
| WO | WO9425583 | A1 | 11/1994 |
| WO | WO1997016076 | A1 | 5/1997 |
| WO | WO9820115 | A1 | 5/1998 |
| WO | WO2006043178 | A2 | 4/2006 |
| WO | WO2007044968 | A2 | 4/2007 |
| WO | WO2008092901 | A2 | 8/2008 |
| WO | WO2008097619 | A2 | 8/2008 |
| WO | WO2009129489 | A2 | 10/2009 |
| WO | WO2010122532 | A2 | 10/2010 |
| WO | WO2012110778 | A2 | 8/2012 |
| WO | WO2018154593 | A1 | 8/2018 |
| WO | WO2017218680 | A1 | 4/2019 |

OTHER PUBLICATIONS

Hillmann et al., "PerR acts as a switch for oxygen tolerance in the strict anaerobe Clostridium acetobutylicum", Molecular Microbiology, vol. 68(4), pp. 848-860. (Year: 2008).*
Shetty et al., "Comparative Genome Analysis of *Megasphaera* sp. Reveals Niche Specialization and Its Potential Role in the Human Gut", PLOS One, vol. 8, Issue 11, pp. 1-13. (Year: 2013).*
CP027570, Nucleotide [Internet]. Bethesda (MD): National Library of Medicine (US), National Center for Biotechnology Information; [2019]—Accession No. CP027570. Accessed Mar. 2025. (Year: 2019).*
Elghandour et al., "*Saccharomyces cerevisiae* as a probiotic feed additive to non and pseudo-ruminant feeding: a review", Journal of Applied Microbiology, vol. 128, pp. 658-674. (Year: 2019).*
Duarte & Latour, Future Med. Chem, (2013) 5(11), 1177-1179.

* cited by examiner

*Primary Examiner* — Melenie L Gordon
*Assistant Examiner* — Grant C Currens

(57) ABSTRACT
Provided herein, inter alia, are compositions comprising oxygen tolerant strains of *Megasphaera elsdenii* and methods of making and using the same to promote improvement of one or more metrics in an animal, such as increased bodyweight/carcass gain, increased feed intake, decreased feed conversion ratio (FCR), decreased medical costs, decreased transition period, decrease use of antibiotics, and reduced mortality.

17 Claims, 6 Drawing Sheets
Specification includes a Sequence Listing.

SEQUENCE LISTING

<160> NUMBER OF SEQ ID NOS: 7

<210> SEQ ID NO 1
<211> LENGTH: 1031
<212> TYPE: DNA
<213> ORGANISM: Megasphaera elsdenii

<400> SEQUENCE: 1

```
catggagagt ttgatcctgg ctcaggacga acgctggcgg cgtgcttaac acatgcaagt      60
cgaacgagaa gagatgagaa gcttgcttct tattgattcg agtggcaaac gggtgagtaa     120
cgcgtaagca acctgcccct cagatgggga caacagctg aaacggctgc taataccgaa      180
tacgttcttt ttgtcgcatg gcagagagaa gaaagggagg ctcttcggag ctttcgctga    240
aggaggggct tgcgtctgat tagctagttg gaggggtaac ggcccaccaa ggcgacgatc    300
agtagccggt ctgagaggat gaacggccac attgggactg agacacggcc cagactccta    360
cgggaggcag cagtggggaa tcttccgcaa tggacgaaag tctgacggag caacgccgcg    420
tgaacgatga cggccttcgg gttgtaaagt tctgttatac gggacgaatg cgtagcggt     480 caatacccgt tacgagtgac ggtaccgtaa gagaaagcca cggctaacta cgtgccagca    540
gccgcggtaa tacgtaggtg gcaagcgttg tccggaatta ttgggcgtaa agggcgcgca    600
ggcggcgtcg taagtcggtc ttaaaagtgc ggggcttaac cccgtgaggg gaccgaaact    660
gcgatgctag agtatcggag aggaaagcgg aattcctagt gtagcggtga aatgcgtaga    720
tattaggagg aacaccagtg gcgaaagcgg ctttctggac gacaactgac gctgaggcgc    780
gaaagccagg ggagcaaacg ggattagata ccccggtagt cctggccgta aacgatggat    840
actaggtgta ggaggtatcg accccttctg tgccggagtt aacgcaataa gtatcccgcc    900
tggggagtac ggccgcaagg ctgaaactca aaggaattga cgggggcccg cacaagcggt    960
ggagtatgtg gtttaattcg acgcaacgcg aagaaccttxa ccaagccttg acattgattg   1020
ctatgggtag a                                                        1031
```

<210> SEQ ID NO 2
<211> LENGTH: 1464
<212> TYPE: DNA
<213> ORGANISM: Megasphaera elsdenii

<400> SEQUENCE: 2

```
cgagtggcaa acgggtgagt aacgcgtaag caacctgccc ttcagatggg gacaacagct      60
ggaaacggct gctaataccg aatacgttct ttttgtcgca tggcagaggg aagaaaggga     120
ggctcttcgg agctttcgct gaaggagggg cttgcgtctg attagctagt tggaggggta    180
acggcccacc aaggcgacga tcagtagccg gtctgagagg atgaacggcc acattgggac    240
```

-continued

```
tgagacacgg cccagactcc tacgggaggc agcagtgggg aatcttccgc aatggacgaa       300
agtctgacgg agcaacgccg cgtgaacgat gacggccttc gggttgtaaa gttctgttat       360
acgggacgaa tggcgtagcg gtcaataccc gttacgagtg acggtaccgt aagagaaagc       420
cacggctaac tacgtgccag cagccgcggt aatacgtagg tggcaagcgt tgtccggaat       480
tattgggcgt aaagggcgcg caggcggcgt cgtaagtcgg tcttaaaagt gcggggctta       540
accccgtgag gggaccgaaa ctgcgatgct agagtatcgg agaggaaagc ggaattccta       600
gtgtagcggt gaaatgcgta gatattagga ggaacaccag tggcgaaagc ggctttctgg       660
acgacaactg acgctgaggc gcgaaagcca ggggagcaaa cgggattaga taccccggta       720
gtcctggccg taaacgatgg atactaggtg taggaggtat cgaccccttc tgtgccggag       780
ttaacgcaat aagtatcccg cctggggagt acggccgcaa ggctgaaact caaaggaatt       840
gacgggggcc cgcacaagcg gtggagtatg tggtttaatt cgacgcaacg cgaagaacct       900
taccaagcct tgacattgat tgctatggat agagatatcc agttcctctt cggaggacaa       960
gaaaacaggt ggtgcacggc tgtcgtcagc tcgtgtcgtg agatgttggg ttaagtcccg      1020
caacgagcgc aacccctatc ttctgttacc agcggttcgg ccgggactc aggagagact      1080 gccgcagaca atgcggagga aggcggggat gacgtcaagt catcatgccc cttatggctt      1140
gggctacaca cgtactacaa tggctcttaa tagagggaag cgaaggagcg atccggagca      1200
aaccccaaaa acagagtccc agttcggatt gcaggctgca actcgcctgc atgaagcagg      1260
aatcgctagt aatcgcaggt cagcatactg cggtgaatac gttcccgggc cttgtacaca      1320
ccgcccgtca caccacgaaa gtcattcaca cccgaagccg gtgaggtaac cttttggagc      1380
cagccgtcga aggtggggc gatgattggg gtgaagtcgt aacaaggtag ccgtatcgga      1440
aggtgcggct ggatcaccte cttt                                          1464
```

<210> SEQ ID NO 3
<211> LENGTH: 1018
<212> TYPE: DNA
<213> ORGANISM: Megasphaera elsdenii

<400> SEQUENCE: 3

```
catggagagt ttgatcctgg ctcaggacga acgctggcgg cgtgcttaac acatgcaagt        60
cgaacgagaa gagatgagaa gcttgcttct tattgattcg agtggcaaac gggtgagtaa       120
cgcgtaagca acctgccctt cagatgggga caacagctgg aaacggctgc taataccgaa       180
tacgttcttt ttgtcgcatg gcagaggga gaaaggggag ctcttcggag ctttcgctga       240 aggagggggct tgcgtctgat tagctagttg gagggggtaac ggcccaccaa ggcgacgatc       300
agtagccggc ctgagaggat gaacggccac attgggactg agacacggcc cagactccta       360
cgggaggcag cagtggggaa tcttccgcaa tggacgaaag tctgacggag caacgccgcg       420
tgaacgatga cggccttcgg gttgtaaagt tctgttatac gggacgaatg gcgtagcggt       480
caatacccgt tacgagtgac ggtaccgtaa gagaaagcca ggctaacta cgtgccagca       540 gccgcggtaa tacgtaggtg caagcgttg tccggaatta ttgggcgtaa agggcgcgca       600
ggcggcgtcg taagtcggtc ttaaaagtgc ggggcttaac cccgtgaggg gaccgaaact       660
gcgatgctag agtatcggag aggaaagcgg aattcctagt gtagcggtga aatgcgtaga       720
tattaggagg aacaccagtg gcgaaagcgg ctttctggac gacaactgac gctgaggcgc       780
gaaagccagg ggagcaaacg ggattagata ccccggtagt cctggccgta aacgatggat       840
```

```
actaggtgta ggaggtatcg accccttctg tgccggagtt aacgcaataa gtatcccgcc        900
tggggagtac ggccgcaagg ctgaaactca aaggaattga cggggggcccg cacaagcggt        960 ggagtatgtg gtttaattcg acgcaacgcg aagaacctta ccaagccttg acattgat         1018
```

```
<210> SEQ ID NO 4
<211> LENGTH: 411
<212> TYPE: DNA
<213> ORGANISM: Artificial Sequence
<220> FEATURE:
<223> OTHER INFORMATION: Transcriptional Regulator

<400> SEQUENCE: 4
atggaaattg ctgaagtttt gcgaaaaaac ggctataaag taactccgca gcgcctggct         60
gtgtacgaag ccatcaatca caatccgacg catcccaatg ccgaggcgat ttacaagata        120
ttacagccca attatccgtc tatgagtctg gctacggtct acaagacgat ggaaatcttt        180
gccaaaattg gcgttgtcca ggtcttgcag tgtgcagaag atgcccatcg ctatgattat        240
aatacaactc cccatgccca tattcgttgc gaaaaatgca accgcgtcat cgatatcgac        300
atggaccagg agggattgcg tcagcaggcg gctgaacaga gcggcttcgt cgtcaacggc        360
gtcagtattt cgtttgtcgg gatttgcccg gaatgtcggg aaaaatcgta a               411
```

```
<210> SEQ ID NO 5
<211> LENGTH: 136
<212> TYPE: PRT
<213> ORGANISM: Artificial Sequence
<220> FEATURE:
<223> OTHER INFORMATION: Transcriptional regulator

<400> SEQUENCE: 5

Met Glu Ile Ala Glu Val Leu Arg Lys Asn Gly Tyr Lys Val Thr Pro
1               5                   10                  15

Gln Arg Leu Ala Val Tyr Glu Ala Ile Asn His Asn Pro Thr His Pro
            20                  25                  30

Asn Ala Glu Ala Ile Tyr Lys Ile Leu Gln Pro Asn Tyr Pro Ser Met
        35                  40                  45

Ser Leu Ala Thr Val Tyr Lys Thr Met Glu Ile Phe Ala Lys Ile Gly
    50                  55                  60

Val Val Gln Val Leu Gln Cys Ala Glu Asp Ala His Arg Tyr Asp Tyr
65                  70                  75                  80

Asn Thr Thr Pro His Ala His Ile Arg Cys Glu Lys Cys Asn Arg Val
                85                  90                  95

Ile Asp Ile Asp Met Asp Gln Glu Gly Leu Arg Gln Gln Ala Ala Glu
            100                 105                 110

Gln Ser Gly Phe Val Val Asn Gly Val Ser Ile Ser Phe Val Gly Ile
        115                 120                 125

Cys Pro Glu Cys Arg Glu Lys Ser
    130                 135
```

```
<210> SEQ ID NO 6
<211> LENGTH: 136
<212> TYPE: PRT
<213> ORGANISM: Artificial Sequence
<220> FEATURE:
<223> OTHER INFORMATION: Transcriptional regulator

<400> SEQUENCE: 6

Met Glu Ile Ala Glu Val Leu Arg Lys Asn Gly Tyr Lys Val Thr Pro
1               5                   10                  15
```

-continued

```
Gln Arg Leu Ala Val Tyr Glu Ala Ile Asn His Asn Pro Thr His Pro
        20              25                  30

Asn Ala Glu Ala Ile Tyr Lys Ile Leu Gln Pro Asn Tyr Pro Ser Met
        35              40                  45

Ser Leu Ala Thr Val Tyr Lys Thr Met Glu Ile Phe Ala Lys Ile Gly
    50              55                  60

Val Val Gln Val Leu Gln Cys Ala Glu Asp Ala His Arg Tyr Asp Tyr
65              70                  75                  80

Asn Thr Thr Pro His Ala His Ile Arg Cys Glu Lys Cys Asn Arg Val
            85                  90                  95

Ile Asp Ile Asp Met Asp Gln Glu Gly Leu Arg Gln Gln Ala Ala Glu
            100                 105                 110

Gln Ser Gly Phe Val Val Asn Gly Val Ser Ile Ser Phe Val Gly Ile
        115                 120                 125

Phe Pro Glu Cys Arg Glu Lys Ser
    130                 135
```

```
<210> SEQ ID NO 7
<211> LENGTH: 411
<212> TYPE: DNA
<213> ORGANISM: Artificial Sequence
<220> FEATURE:
<223> OTHER INFORMATION: Transcriptional regulator

<400> SEQUENCE: 7
atggaaattg ctgaagtttt gcgaaaaaac ggctataaag taactccgca gcgcctggct      60
gtgtacgaag ccatcaatca caatccgacg catcccaatg ccgaggcgat ttacaagata     120
ttacagccca attatccgtc tatgagtctg gctacggtct acaagacgat ggaaatcttt     180
gccaaaattg gcgttgtcca ggtcttgcag tgtgcagaag atgcccatcg ctatgattat     240
aatacaactc cccatgccca tattcgttgc gaaaaatgca accgcgtcat cgatatcgac     300
atggaccagg agggattgcg tcagcaggcg gctgaacaga gcggcttcgt cgtcaacggc     360
gtcagtattt cgtttgtcgg gattttcccg gaatgtcggg aaaaatcgta a             411
```

FEED COMPOSITIONS FOR ANIMAL HEALTH

CROSS-REFERENCE TO RELATED APPLICATIONS

This application is a U.S. National Phase application under 35 U.S.C. § 371 of International Patent Application No. PCT/US2021/016837, filed Feb. 5, 2021, which claims the benefit of U.S. Provisional Patent Application No. 63/082,634, filed Sep. 24, 2020, and U.S. Provisional Patent Application No. 62/971,503, filed Feb. 7, 2020, the disclosure of each of which is incorporated by reference herein in its entirety.

FIELD OF THE INVENTION

Provided herein, inter alia, are feed and feed additive compositions comprising oxygen-tolerant strains of *Megasphaera elsdenii* direct fed microbials (DFMs) useful for improving animal health and/or performance, increasing useable shelf life, as well as methods of making and using the same.

INCORPORATION BY REFERENCE TO A SEQUENCE LISTING

The contents of the electronic submission of the text file Sequence Listing, named "20210203_NB41609WOPCT_SeqList_ST25.txt" was created on Feb. 3, 2021, and is 12,288 bytes in size, which is hereby incorporated by reference in its entirety.

BACKGROUND

In monogastric and ruminant animal species, the gastrointestinal tract and digestive system-associated microflora are not only involved in digestion and absorption but also interact with the immune and central nervous system to modulate health. The inside of the digestive tract is coated with a thin layer of sticky, viscous mucous, and embedded in this mucus layer are millions and millions of bacteria and other microbes. When the bacteria are in balance (i.e., the good bacteria outnumber the bad bacteria), the gut is said to be healthy. A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of "dysbiosis" or disrupted symbiosis, microbiota functions can be lost or deranged, resulting in increased susceptibility to pathogens, altered metabolic profiles, or induction of proinflammatory signals that can result in local or systemic inflammation or autoimmunity. Thus, the microbiota of the gastrointestinal tract of animals plays a significant role in the pathogenesis of many diseases and disorders, such as acidosis in ruminants.

Most of the current probiotics for human or direct fed microbials (DFMs) for animal nutrition on the market can either grow in the presence of oxygen and/or tolerate oxygen exposure. Examples of such microorganisms include the Bacilli, which is a class of aerobes containing two orders, and *Lactobacillus*, which is a genus of facultative anaerobes. However, more and more next-generation probiotics/DFMs are obligate anaerobes that are sensitive to oxygen. The stability of these products during processing, transport, and storage is a concern, primarily resulting in shorter shelf life due to inability to tolerate oxygen. Formulation and encapsulation with stabilizers may somewhat improve stability, though even then these products exhibit shelf lives significantly less than corresponding products containing aerobic microorganisms. For example, LactiPro® (MSBiotec, Wamego, KS) contains a pure culture of the obligate anaerobe *Megasphaera elsdenii* NCIMB41125 and is an effective DFM product for use in treating acidosis in ruminants. However, the shelf life of liquid formulated LactiPro is only about two weeks at 4° C. and this product instability limits the use of LactiPro in the market, particularly in areas of the world lacking access to refrigeration. What is needed, therefore, are anaerobic bacteria for use in treating conditions associated with dysbiosis in ruminant animals, such as acidosis, that exhibit tolerance to oxygen, increased viability following oxygen exposure, as well as increased shelf and storage life.

The subject matter disclosed herein addresses these needs and provides additional benefits as well.

SUMMARY

Provided herein, inter alia, are compositions comprising oxygen tolerant strains of *Megasphaera elsdenii* direct fed microbials (DFMs) and methods for making and using the same to promote improvement of one or more metrics in an animal, such as increased bodyweight/carcass gain, increased feed intake, decreased feed conversion ratio (FCR), decreased medical costs, reduced mortality, reduced transition time from a forage/grass/silage diet to a high concentrate diet, and/or reduced incidence of rumen acidosis. The anaerobic bacteria compositions disclosed herein additionally exhibit increased shelf life and viability upon exposure to oxygen.

Accordingly, in some aspects, provided herein is a feed additive composition comprising a direct fed microbial (DFM) comprising at least one biologically pure strain of an oxygen tolerant *Megasphaera elsdenii*. In some embodiments, the oxygen tolerant *M. elsdenii* comprises at least one mutation (a) in a gene encoding the transcriptional regulator PerR comprising SEQ ID NO: 4; or (b) immediately upstream of the gene encoding the transcriptional regulator PerR. In some embodiments of any of the embodiments described herein, the at least one mutation is (a) a nucleotide substitution resulting in an amino acid change in the PerR protein; and/or (b) an insertion of a nucleotide resulting in a frameshift mutation. In some embodiments, the nucleotide substitution is at a nucleotide position selected from the group consisting of 386, 155, 253, −99, and −125 corresponding to a gene encoded by the polynucleotide sequence of SEQ ID NO:4. In some embodiments, the nucleotide substitution comprises G386T, C155T, C253T, T-99C, or G-125A. In some embodiments of any of the embodiments described herein, the amino acid change comprises C129F, T52M, or H85Y corresponding to the polypeptide encoded by SEQ ID NO:5. In some embodiments, the PerR protein comprises the polypeptide encoded by SEQ ID NO:6. In some embodiments, the nucleotide insertion is at a nucleotide position selected from the group consisting of 30, 277, and 64 corresponding to SEQ ID NO:4. In some embodiments, the insertion is an A at position 30, an A at position 277, or a G at position 64. In some embodiments of any of the embodiments described herein, the composition comprises one or more of (a) an *M. elsdenii* strain having a 16S ribosomal RNA sequence displaying at least 97.0% sequence similarity to a 16S ribosomal DNA sequence of an *M. elsdenii* strain ACD1265 deposited at Westerdijk Fungal Biodiversity Institute (WFDI) under number CBS 146328; (b) an *M. elsdenii* strain having a 16S ribosomal RNA sequence displaying at least 97.0% sequence similarity to a 16S ribosomal DNA sequence of an *M. elsdenii* strain ACD1096-A01; (c) an *M. elsdenii* strain having a 16S ribosomal RNA sequence displaying at least 97.0% sequence similarity to a 16S ribosomal DNA sequence of an *M. elsdenii* strain ACD1096-B01; (d) an *M. elsdenii* strain having a 16S ribosomal RNA sequence displaying at least 97.0% sequence similarity to a 16S ribosomal DNA sequence of an *M. elsdenii* strain ACD1096-E01; (e) an *M. elsdenii* strain having a 16S ribosomal RNA sequence displaying at least 97.0% sequence similarity to a 16S ribosomal DNA sequence of an *M. elsdenii* strain ACD1096-C02; (f) an *M. elsdenii* strain having a 16S ribosomal RNA sequence displaying at least 97.0% sequence similarity to a 16S ribosomal DNA sequence of an *M. elsdenii* strain ACD1096-C05; (g) an *M. elsdenii* strain having a 16S ribosomal RNA sequence displaying at least 97.0% sequence similarity to a 16S ribosomal DNA sequence of an *M. elsdenii* strain ACD1096-H05; (h) an *M. elsdenii* strain having a 16S ribosomal RNA sequence displaying at least 97.0% sequence similarity to a 16S ribosomal DNA sequence of an *M. elsdenii* strain ACD1096-B03; (i) an *M. elsdenii* strain having a 16S ribosomal RNA sequence displaying at least 97.0% sequence similarity to a 16S ribosomal DNA sequence of an *M. elsdenii* strain ACD1141-C10; (j) an *M. elsdenii* strain having a 16S ribosomal RNA sequence displaying at least 97.0% sequence similarity to a 16S ribosomal DNA sequence of an *M. elsdenii* strain ACD1141-D10; (k) an *M. elsdenii* strain having a 16S ribosomal RNA sequence displaying at least 97.0% sequence similarity to a 16S ribosomal DNA sequence of an *M. elsdenii* strain ACD1141 deposited at WFDI under number CBS 146325; (1) an *M. elsdenii* strain having a 16S ribosomal RNA sequence displaying at least 97.0% sequence similarity to a 16S ribosomal DNA sequence of an *M. elsdenii* strain ACD1141E deposited at WFDI under number CBS 146326; (m) an *M. elsdenii* strain having a 16S ribosomal RNA sequence displaying at least 97.0% sequence similarity to a 16S ribosomal DNA sequence of an *M. elsdenii* strain ACD1141F deposited at WFDI under number CBS 146327; (n) an *M. elsdenii* strain having a 16S ribosomal RNA sequence displaying at least 97.0% sequence similarity to a 16S ribosomal DNA sequence of an *M. elsdenii* strain ACD1265E deposited at WFDI under number CBS 146329; and/or (o) an *M. elsdenii* strain having a 16S ribosomal RNA sequence displaying at least 97.0% sequence similarity to a 16S ribosomal DNA sequence of an *M. elsdenii* strain ACD1265F deposited at WFDI under number CBS 146330. In some embodiments of any of the embodiments described herein, the composition comprises one or more of (a) *M. elsdenii* strain ACD1265 or a live strain having all of the identifying characteristics of *M. elsdenii* strain ACD1265; (b) *M. elsdenii* strain ACD1096-A01 or a live strain having all of the identifying characteristics of *M. elsdenii* strain ACD1096-A01; (c) *M. elsdenii* strain ACD1096-B01 or a live strain having all of the identifying characteristics of *M. elsdenii* strain ACD1096-B01; (d) *M. elsdenii* strain ACD1096-E01 or a live strain having all of the identifying characteristics of *M. elsdenii* strain ACD1096-E01; (e) *M. elsdenii* strain ACD1096-C02 or a live strain having all of the identifying characteristics of *M. elsdenii* strain ACD1096-C02; (f) *M. elsdenii* strain ACD1096-C05 or a live strain having all of the identifying characteristics of *M. elsdenii* strain ACD1096-C05; (g) *M. elsdenii* strain ACD1096-H05 or a live strain having all of the identifying characteristics of *M. elsdenii* strain ACD1096-H05; (h) *M. elsdenii* strain ACD1096-B03 or a live strain having all of the identifying characteristics of *M. elsdenii* strain ACD1096-B03; (i) *M. elsdenii* strain ACD1141-C10 or a live strain having all of the identifying characteristics of *M. elsdenii* strain ACD1141-C10; (j) *M. elsdenii* strain ACD1141-D10 or a live strain having all of the identifying characteristics of *M. elsdenii* strain ACD1141-D10; (k) *M. elsdenii* strain ACD1141 or a live strain having all of the identifying characteristics of *M. elsdenii* strain ACD1141; (1) *M. elsdenii* strain ACD1141E or a live strain having all of the identifying characteristics of *M. elsdenii* strain ACD1141E; (m) *M. elsdenii* strain ACD1141F or a live strain having all of the identifying characteristics of *M. elsdenii* strain ACD1141F; (n) *M. elsdenii* strain ACD1265E or a live strain having all of the identifying characteristics of *M. elsdenii* strain ACD1265E; and/or (o) *M. elsdenii* strain ACD1265F or a live strain having all of the identifying characteristics of *M. elsdenii* strain ACD1265F, either (A) cultured alone; or (B) in combination with a culture supernatant derived from one or more these strains. In some embodiments of any of the embodiments described herein, the composition comprises one or more of (i) a bacterial strain having a 16S ribosomal RNA sequence displaying at least 97.0% sequence similarity to a 16S ribosomal RNA sequence of an *M. elsdenii* strain ACD1265 comprising SEQ ID NO:1; (ii) a bacterial strain having a 16S ribosomal RNA sequence displaying at least 97.0% sequence similarity to a 16S ribosomal RNA sequence of an *M. elsdenii* strain ACD1096-A01 comprising SEQ ID NO:2 or (iii) a bacterial strain having a 16S ribosomal RNA sequence displaying at least 97.0% sequence similarity to a 16S ribosomal RNA sequence of an *M. elsdenii* strain ACD1141 comprising SEQ ID NO:3, either (A) cultured alone; or (B) in combination with a culture supernatant derived from one or more of these strains. In some embodiments of any of the embodiments described herein, the oxygen tolerant *M. elsdenii* remains viable after at least about 7-12 days of exposure to oxygen. In some embodiments, at least about $5.73 \times 10^2$ to about $1.16 \times 10^8$ cfu/mL of the *M. elsdenii* remains viable after 7-12 days of exposure to oxygen. In some embodiments of any of the embodiments described herein, the oxygen tolerant *M. elsdenii* remains viable after at least 10 days after exposure to oxygen. In some embodiments of any of the embodiments described herein, the composition further comprises at least one yeast strain and/or yeast extract. In some embodiments, the yeast strain is from the genus *Saccharomyces* or *Pichia* or *Aspergillus*. In some embodiments, the yeast is *Saccharomyces cerevisiae* or *Pichia* kudriavzevii or *Saccharomyces boulardii* or *Aspergillus oryzae*. In some embodiments of any of the embodiments described herein, the oxygen tolerant *M. elsdenii* exhibits increased oxygen tolerance when in the presence of the at least one yeast strain and/or yeast extract versus when alone. In some embodiments of any of the embodiments described herein, the feed additive composition further comprises one or more excipients. In some embodiments, the excipient comprises one or more of a polysaccharide, a protein, an anti-oxidant, or an inorganic solid or oil. In some embodiments of any of the embodiments described herein, the one or more excipients improves or increases the on-feed cattle stability by greater than about 50% compared to a composition that lacks the one or more excipients. In some embodiments of any of the embodiments described herein, the composition further comprises one or more enzymes. In some embodiments, the one or more enzymes are selected from the group consisting of a phytase, a protease, an amylase, a xylanase, a glucoamylase, and a beta-glucanase. In some embodiments of any of the embodiments described herein, each *M. elsdenii* strain is present at a concentration of at least about $1\times10^3$ CFU/g feed additive composition to at least about $1\times10^{11}$ CFU/g feed additive composition. In some embodiments of any of the embodiments described herein, the composition is formulated as a liquid or a solid. In some embodiments of any of the embodiments described herein, the composition treats or prevents acidosis in a ruminant animal.

In another aspect, provided herein is a premix comprising any of the feed additive compositions disclosed herein and at least one mineral and/or at least one vitamin.

In a further aspect, provided herein is a feed comprising any of the feed additive compositions disclosed herein or the any of the premixes disclosed herein.

In other aspects, provided herein is a kit comprising a) any of the feed additive compositions disclosed herein; and b) written instructions for administration to an animal. In some embodiments, the kit further comprises one or more enzymes. In some embodiments, the one or more enzymes are selected from the group consisting of a phytase, a protease, an amylase, a xylanase, a glucoamylase, and a beta-glucanase.

In still other aspects, provided herein is a method for improving one or more metrics in an animal selected from the group consisting of increased bodyweight/carcass gain, increased feed intake, decreased feed conversion ratio (FCR), decreased medical costs, decreased transition period, decrease use of antibiotics, and reduced mortality, comprising administering an effective amount of any of the feed additive compositions disclosed herein, any of the premixes disclosed herein, or any of the feeds disclosed herein to the animal, thereby improving the one or more metrics in the animal. In some embodiments, the animal is a ruminant. In some embodiments, the animal is a cow, goat, sheep, buffalo, deer or other member of the Ruminantia suborder of mammals. In some embodiments, the animal is a dairy cow or a beef cow. In some embodiments of any of the embodiments described herein, the method further treats, prevents, or decreases incidence of rumen acidosis in the animal. In some embodiments, the animal is a member of the genus *Equus*. In some embodiments, the animal is a horse, mule, donkey, or zebra. In some embodiments of any of the embodiments described herein, the method decreases the incidence of stomach ulcers in animals of the genus *Equus* that are fed on a diet comprising one or more high energy grains. In some embodiments, said high energy grains are oats and/or corn.

In some aspects, provided herein is a method for treating, preventing, or decreasing incidence of rumen acidosis in a ruminant animal comprising administering an effective amount of any of the feed additive compositions disclosed herein, any of the premixes disclosed herein, or any of the feeds disclosed herein to the animal, thereby treating, preventing, or decreasing incidence of rumen acidosis in the animal. In some embodiments, said administration raises or maintains the pH of the rumen of the animal above pH 5.6. In some embodiments of any of the embodiments described herein, the ruminant animal is a cow, goat, sheep, buffalo, deer or other member of the Ruminantia suborder of mammals. In some embodiments, the ruminant animal is a dairy cow or a beef cow.

In another aspect, provided herein is a method for preparing a feed additive composition comprising combining (a) at least one biologically pure strain of an oxygen tolerant *Megasphaera elsdenii*; and (b) at least one yeast strain and/or yeast extract. In some embodiments, the oxygen tolerant *M. elsdenii* comprises at least one mutation (a) in a gene upstream of the gene encoding the transcriptional regulator PerR. In some embodiments of any of the embodiments described herein, the at least one mutation is (a) a nucleotide substitution resulting in an amino acid change in the PerR protein; and/or (b) an insertion of a nucleotide resulting in a frameshift mutation. In some embodiments, the nucleotide substitution is at a nucleotide position selected from the group consisting of 386, 155, 253, −99, and −125 relative to a gene encoded by the polynucleotide sequence of SEQ ID NO:4. In some embodiments, the nucleotide substitution comprises G386T, C155T, C253T, T-99C, or G-125A. In some embodiments of any of the embodiments described herein, the amino acid change comprises C129F, T52M, or H85Y relative to the polypeptide encoded by SEQ ID NO:5. In some embodiments, the PerR protein comprises the polypeptide encoded by SEQ ID NO:6. In some embodiments, the nucleotide insertion is at a nucleotide position selected from the group consisting of 30, 277, and 64 relative to SEQ ID NO:4. In some embodiments, the insertion is an A at position 30, an A at position 277, or a G at position 64. In some embodiments of any of the embodiments described herein, the oxygen tolerant *Megasphaera elsdenii* comprises (i) an *M. elsdenii* strain having a 16S ribosomal RNA sequence displaying at least 97.0% sequence similarity to a 16S ribosomal DNA sequence of an *M. elsdenii* strain ACD1265 deposited at Westerdijk Fungal Biodiversity Institute (WFDI) under number CBS 146328; (ii) an *M. elsdenii* strain having a 16S ribosomal RNA sequence displaying at least 97.0% sequence similarity to a 16S ribosomal DNA sequence of an *M. elsdenii* strain ACD1096-A01; (iii) an *M. elsdenii* strain having a 16S ribosomal RNA sequence displaying at least 97.0% sequence similarity to a 16S ribosomal DNA sequence of an *M. elsdenii* strain ACD1096-B01; (iv) an *M. elsdenii* strain having a 16S ribosomal RNA sequence displaying at least 97.0% sequence similarity to a 16S ribosomal DNA sequence of an *M. elsdenii* strain ACD1096-E01; (v) an *M. elsdenii* strain having a 16S ribosomal RNA sequence displaying at least 97.0% sequence similarity to a 16S ribosomal DNA sequence of an *M. elsdenii* strain ACD1096-C02; (vi) an *M. elsdenii* strain having a 16S ribosomal RNA sequence displaying at least 97.0% sequence similarity to a 16S ribosomal DNA sequence of an *M. elsdenii* strain ACD1096-C05; (vii) an *M. elsdenii* strain having a 16S ribosomal RNA sequence displaying at least 97.0% sequence similarity to a 16S ribosomal DNA sequence of an *M. elsdenii* strain ACD1096-H05; (viii) an *M. elsdenii* strain having a 16S ribosomal RNA sequence displaying at least 97.0% sequence similarity to a 16S ribosomal DNA sequence of an *M. elsdenii* strain ACD1096-B03; (ix) an *M. elsdenii* strain having a 16S ribosomal RNA sequence displaying at least 97.0% sequence similarity to a 16S ribosomal DNA sequence of an *M. elsdenii* strain ACD1141-C10; (x) an *M. elsdenii* strain having a 16S ribosomal RNA sequence displaying at least 97.0% sequence similarity to a 16S ribosomal DNA sequence of an *M. elsdenii* strain ACD1141-D10; (xi) an *M. elsdenii* strain having a 16S ribosomal RNA sequence displaying at least 97.0% sequence similarity to a 16S ribosomal DNA sequence of an *M. elsdenii* strain ACD1141 deposited at WFDI under number CBS 146325; (xii) an *M. elsdenii* strain having a 16S ribosomal RNA sequence displaying at least 97.0% sequence similarity to a 16S ribosomal DNA sequence of an *M. elsdenii* strain ACD1141E deposited at WFDI under number CBS 146326; (xiii) an *M. elsdenii* strain having a 16S ribosomal RNA sequence displaying at least 97.0% sequence similarity to a 16S ribosomal DNA sequence of an *M. elsdenii* strain ACD1141F deposited at WFDI under number CBS 146327; (xiv) an *M. elsdenii* strain having a 16S ribosomal RNA sequence displaying at least 97.0% sequence similarity to a 16S ribosomal DNA sequence of an *M. elsdenii* strain ACD1265E deposited at WFDI under number CBS 146329; and/or (xv) an *M. elsdenii* strain having a 16S ribosomal RNA sequence displaying at least 97.0% sequence similarity to a 16S ribosomal DNA sequence of an *M. elsdenii* strain ACD1265F deposited at WFDI under number CBS 146330. In some embodiments, the *M. elsdenii* strain is (i) *M. elsdenii* strain ACD1265 or a live strain having all of the identifying characteristics of *M. elsdenii* strain ACD1265; (ii) *M. elsdenii* strain ACD1096-A01 or a live strain having all of the identifying characteristics of *M. elsdenii* strain ACD1096-A01; (iii) *M. elsdenii* strain ACD1096-B01 or a live strain having all of the identifying characteristics of *M. elsdenii* strain ACD1096-B01; (iv) *M. elsdenii* strain ACD1096-E01 or a live strain having all of the identifying characteristics of *M. elsdenii* strain ACD1096-E01; (v) *M. elsdenii* strain ACD1096-C02 or a live strain having all of the identifying characteristics of *M. elsdenii* strain ACD1096-C02; (vi) *M. elsdenii* strain ACD1096-C05 or a live strain having all of the identifying characteristics of *M. elsdenii* strain ACD1096-C05; (vii) *M. elsdenii* strain ACD1096-H05 or a live strain having all of the identifying characteristics of *M. elsdenii* strain ACD1096-H05; (viii) *M. elsdenii* strain ACD1096-B03 or a live strain having all of the identifying characteristics of *M. elsdenii* strain ACD1096-B03; (ix) *M. elsdenii* strain ACD1141-C10 or a live strain having all of the identifying characteristics of *M. elsdenii* strain ACD1141-C10; (x) *M. elsdenii* strain ACD1141-D10 or a live strain having all of the identifying characteristics of *M. elsdenii* strain ACD1141-D10; (xi) *M. elsdenii* strain ACD1141 or a live strain having all of the identifying characteristics of *M. elsdenii* strain ACD1141; (xii) *M. elsdenii* strain ACD1141E or a live strain having all of the identifying characteristics of *M. elsdenii* strain ACD1141E; (xiii) *M. elsdenii* strain ACD1141F or a live strain having all of the identifying characteristics of *M. elsdenii* strain ACD1141F; (xiv) *M. elsdenii* strain ACD1265E or a live strain having all of the identifying characteristics of *M. elsdenii* strain ACD1265E; and/or (xv) *M. elsdenii* strain ACD1265F or a live strain having all of the identifying characteristics of *M. elsdenii* strain ACD1265F, either (A) cultured alone; or (B) in combination with a culture supernatant derived from one or more these strains. In some embodiments of any of the embodiments described herein, the yeast strain is from the genus *Saccharomyces* or *Pichia* or *Aspergillus*. In some embodiments, the yeast is *Saccharomyces cerevisiae* or *Pichia* kudriavzevii or *Saccharomyces boulardii* or *Aspergillus oryzae*. In some embodiments of any of the embodiments described herein, the method further comprises combining one or more excipients. In some embodiments, the excipient comprises one or more of a polysaccharide, a protein, an anti-oxidant, or an inorganic solid or oil. In some embodiments of any of the embodiments described herein, the method further comprises combining one or more enzyme(s) with the feed additive composition. In some embodiments, the one or more enzymes are selected from the group consisting of a phytase, a protease, an amylase, a xylanase, a glucoamylase, and a beta-glucanase. In some embodiments of any of the embodiments described herein, at least about $1\times10^3$ CFU/g to at least about $1\times10^9$ CFU/g *M. elsdenii* is combined with at least one yeast strain and/or yeast extract to form the feed additive composition. In some embodiments of any of the embodiments described herein, the method further comprises formulating the feed additive composition as a liquid or a solid. In some embodiments of any of the embodiments described herein, the method further comprises packaging the feed additive composition.

In yet another aspect, provided herein is a method for preparing a premix comprising combining any of the feed additive compositions disclosed herein with at least one mineral and/or at least one vitamin. In some embodiments, the method further comprises packaging the premix.

In other aspects, provided herein is a method for increasing the oxygen tolerance of a strain of *Megasphaera elsdenii* comprising introducing at least one mutation (a) in a gene upstream of the gene encoding the transcriptional regulator PerR. In some embodiments, the at least one mutation is (a) a nucleotide substitution resulting in an amino acid change in the PerR protein; and/or (b) an insertion of a nucleotide resulting in a frameshift mutation. In some embodiments, the nucleotide substitution is at a nucleotide position selected from the group consisting of 386, 155, 253, −99, and −125 relative to a gene comprising the polynucleotide sequence of SEQ ID NO:4. In some embodiments, the nucleotide substitution comprises G386T, C155T, C253T, T-99C, or G-125A. In some embodiments of any of the embodiments described herein, the amino acid change comprises C129F, T52M, or H85Y relative to the polypeptide encoded by SEQ ID NO:5. In some embodiments, the PerR protein comprises the polypeptide encoded by SEQ ID NO:6. In some embodiments, the nucleotide insertion is at a nucleotide position selected from the group consisting of 30, 277, and 64 relative to SEQ ID NO:4. In some embodiments, the insertion is an A at position 30, an A at position 277, or a G at position 64. In some embodiments of any of the embodiments described herein, the method further comprises combining the strain of *M. elsdenii* with at least one yeast strain and/or yeast extract. In some embodiments, the yeast strain is from the genus *Saccharomyces* or *Pichia* or *Aspergillus*. In some embodiments, the yeast is *Saccharomyces cerevisiae* or *Pichia* kudriavzevii or *Saccharomyces boulardii* or *Aspergillus oryzae*. In some embodiments of any of the embodiments described herein, the method further comprises combining the strain of *M. elsdenii* with one or more excipients. In some embodiments, the excipient comprises one or more of a polysaccharide, a protein, an anti-oxidant, or an inorganic solid or oil. In some embodiments of any of the embodiments described herein, the strain of *M. elsdenii* remains viable after at least about 7-12 days of exposure to oxygen. In some embodiments, at least about $5.73\times10^4$ to about $1.16\times10^8$ cfu/mL of the *M. elsdenii* remains viable after 7-12 days of exposure to oxygen. In some embodiments of any of the embodiments described herein, the strain of *M. elsdenii* remains viable after at least 30 days after exposure to oxygen. In some embodiments of any of the embodiments described herein, said mutation is introduced via random mutagenesis or site-directed mutagenesis.

In a further aspect, provided herein is a method for increasing the shelf life of a feed additive composition comprising *M. elsdenii* comprising formulating one or more of the oxygen-tolerant *M. elsdenii* strains of any of the feed additive compositions disclosed herein with at least one yeast strain and/or yeast extract. In some embodiments, the yeast strain is from the genus *Saccharomyces* or *Pichia* or *Aspergillus*. In some embodiments, the yeast is *Saccharomyces cerevisiae* or *Pichia* kudriavzevii or *Saccharomyces boulardii* or *Aspergillus oryzae*. In some embodiments of any of the embodiments described herein, the method further comprises combining the strain of *M. elsdenii* with one or more excipients. In some embodiments, the excipient comprises one or more of a polysaccharide, a protein, an anti-oxidant, or an inorganic solid or oil. In some embodiments of any of the embodiments described herein, the feed additive composition has a shelf life of at least about 7-12 days. In some embodiments, the feed additive composition has a shelf life of at least about 30 days. In some embodiments of any of the embodiments described herein, the feed additive compositions is formulated as a liquid or a solid.

In some aspects, provided herein is a biologically pure strain of *Megasphaera elsdenii* comprising (a) an *M. elsdenii* strain having a 16S ribosomal RNA sequence displaying at least 97.0% sequence similarity to a 16S ribosomal DNA sequence of an *M. elsdenii* strain ACD1265 deposited at Westerdijk Fungal Biodiversity Institute (WFDI) under number CBS 146328; (b) an *M. elsdenii* strain having a 16S ribosomal RNA sequence displaying at least 97.0% sequence similarity to a 16S ribosomal DNA sequence of an *M. elsdenii* strain ACD1096-A01; (c) an *M. elsdenii* strain having a 16S ribosomal RNA sequence displaying at least 97.0% sequence similarity to a 16S ribosomal DNA sequence of an *M. elsdenii* strain ACD1096-B01; (d) an *M. elsdenii* strain having a 16S ribosomal RNA sequence displaying at least 97.0% sequence similarity to a 16S ribosomal DNA sequence of an *M. elsdenii* strain ACD1096-E01; (c) an *M. elsdenii* strain having a 16S ribosomal RNA sequence displaying at least 97.0% sequence similarity to a 16S ribosomal DNA sequence of an *M. elsdenii* strain ACD1096-C02; (f) an *M. elsdenii* strain having a 16S ribosomal RNA sequence displaying at least 97.0% sequence similarity to a 16S ribosomal DNA sequence of an *M. elsdenii* strain ACD1096-C05; (g) an *M. elsdenii* strain having a 16S ribosomal RNA sequence displaying at least 97.0% sequence similarity to a 16S ribosomal DNA sequence of an *M. elsdenii* strain ACD1096-H05; (h) an *M. elsdenii* strain having a 16S ribosomal RNA sequence displaying at least 97.0% sequence similarity to a 16S ribosomal DNA sequence of an *M. elsdenii* strain ACD1096-B03; (i) an *M. elsdenii* strain having a 16S ribosomal RNA sequence displaying at least 97.0% sequence similarity to a 16S ribosomal DNA sequence of an *M. elsdenii* strain ACD1141-C10; (j) an *M. elsdenii* strain having a 16S ribosomal RNA sequence displaying at least 97.0% sequence similarity to a 16S ribosomal DNA sequence of an *M. elsdenii* strain ACD1141-D10; (k) an *M. elsdenii* strain having a 16S ribosomal RNA sequence displaying at least 97.0% sequence similarity to a 16S ribosomal DNA sequence of an *M. elsdenii* strain ACD1141 deposited at WFDI under number CBS 146325; (1) an *M. elsdenii* strain having a 16S ribosomal RNA sequence displaying at least 97.0% sequence similarity to a 16S ribosomal DNA sequence of an *M. elsdenii* strain ACD1141E deposited at WFDI under number CBS 146326; (m) an *M. elsdenii* strain having a 16S ribosomal RNA sequence displaying at least 97.0% sequence similarity to a 16S ribosomal DNA sequence of an *M. elsdenii* strain ACD1141F deposited at WFDI under number CBS 146327; (n) an *M. elsdenii* strain having a 16S ribosomal RNA sequence displaying at least 97.0% sequence similarity to a 16S ribosomal DNA sequence of an *M. elsdenii* strain ACD1265E deposited at WFDI under number CBS 146329; and/or (o) an *M. elsdenii* strain having a 16S ribosomal RNA sequence displaying at least 97.0% sequence similarity to a 16S ribosomal DNA sequence of an *M. elsdenii* strain ACD1265F deposited at WFDI under number CBS 146330. In some embodiments, the strain is a (a) *M. elsdenii* strain ACD1265 or a live strain having all of the identifying characteristics of *M. elsdenii* strain ACD1265; (b) *M. elsdenii* strain ACD1096-A01 or a live strain having all of the identifying characteristics of *M. elsdenii* strain ACD1096-A01; (c) *M. elsdenii* strain ACD1096-B01 or a live strain having all of the identifying characteristics of *M. elsdenii* strain ACD1096-B01; (d) *M. elsdenii* strain ACD1096-E01 or a live strain having all of the identifying characteristics of *M. elsdenii* strain ACD1096-E01; (c) *M. elsdenii* strain ACD1096-C02 or a live strain having all of the identifying characteristics of *M. elsdenii* strain ACD1096-C02; (f) *M. elsdenii* strain ACD1096-C05 or a live strain having all of the identifying characteristics of *M. elsdenii* strain ACD1096-C05; (g) *M. elsdenii* strain ACD1096-H05 or a live strain having all of the identifying characteristics of *M. elsdenii* strain ACD1096-H05; (h) *M. elsdenii* strain ACD1096-B03 or a live strain having all of the identifying characteristics of *M. elsdenii* strain ACD1096-B03; (i) *M. elsdenii* strain ACD1141-C10 or a live strain having all of the identifying characteristics of *M. elsdenii* strain ACD1141-C10; (j) *M. elsdenii* strain ACD1141-D10 or a live strain having all of the identifying characteristics of *M. elsdenii* strain ACD1141-D10; (k) *M. elsdenii* strain ACD1141 or a live strain having all of the identifying characteristics of *M. elsdenii* strain ACD1141; (1) *M. elsdenii* strain ACD1141E or a live strain having all of the identifying characteristics of *M. elsdenii* strain ACD1141E; (m) *M. elsdenii* strain ACD1141F or a live strain having all of the identifying characteristics of *M. elsdenii* strain ACD1141F; (n) *M. elsdenii* strain ACD1265E or a live strain having all of the identifying characteristics of *M. elsdenii* strain ACD1265E; and/or (o) *M. elsdenii* strain ACD1265F or a live strain having all of the identifying characteristics of *M. elsdenii* strain ACD1265F. In some embodiments of any of the embodiments described herein, the strain comprises (i) a bacterial strain having a 16S ribosomal RNA sequence displaying at least 97.0% sequence similarity to a 16S ribosomal RNA sequence of an *M. elsdenii* strain ACD1265 comprising SEQ ID NO:1; (ii) a bacterial strain having a 16S ribosomal RNA sequence displaying at least 97.0% sequence similarity to a 16S ribosomal RNA sequence of an *M. elsdenii* strain ACD1096-A01 comprising SEQ ID NO:2 or (iii) a bacterial strain having a 16S ribosomal RNA sequence displaying at least 97.0% sequence similarity to a 16S ribosomal RNA sequence of an *M. elsdenii* strain ACD1141 comprising SEQ ID NO:3.

A method for reducing the time required for transitioning a ruminant animal from a forage/grass/silage diet to a high concentrate diet without increasing the incidence of acidosis comprising administering an effective amount of any of the feed additive compositions disclosed herein, any of the premixes disclosed herein, or any of the feeds disclosed herein to the animal, thereby reducing the time required for transitioning the animal to a high concentrate diet without increasing the incidence of acidosis. In some embodiments, the ruminant animal is a cow, goat, sheep, buffalo, deer or other member of the Ruminantia suborder of mammals. In some embodiments, the ruminant animal is a dairy cow or a beef cow. In some embodiments of any of the embodiments described herein, the time required is on average greater than about 60% less compared with the time required to transition ruminant animals that are not administered an effective amount of any of the feed additive compositions disclosed herein, any of the premixes disclosed herein, or any of the feeds disclosed herein.

In still additional aspects, provided herein is a kit comprising one or more of any of the biologically pure strains of oxygen-tolerant *Megasphaera elsdenii* disclosed herein and written instructions for administration to an animal. In some embodiments, the kit further comprises one or more yeast strains and/or yeast extract. In some embodiments of any of the embodiments disclosed herein, the kit further comprises one or more enzymes. In some embodiments of any of the embodiments described herein, the kit further comprises one or more excipients. In some embodiments, the excipient comprises one or more of a polysaccharide, a protein, an anti-oxidant, or an inorganic solid or oil. In some embodiments of any of the embodiments disclosed herein, the biologically pure strains of *Megasphaera elsdenii* and/or the yeast strains are lyophilized or freeze dried.

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

DETAILED DESCRIPTION

Figure 1:
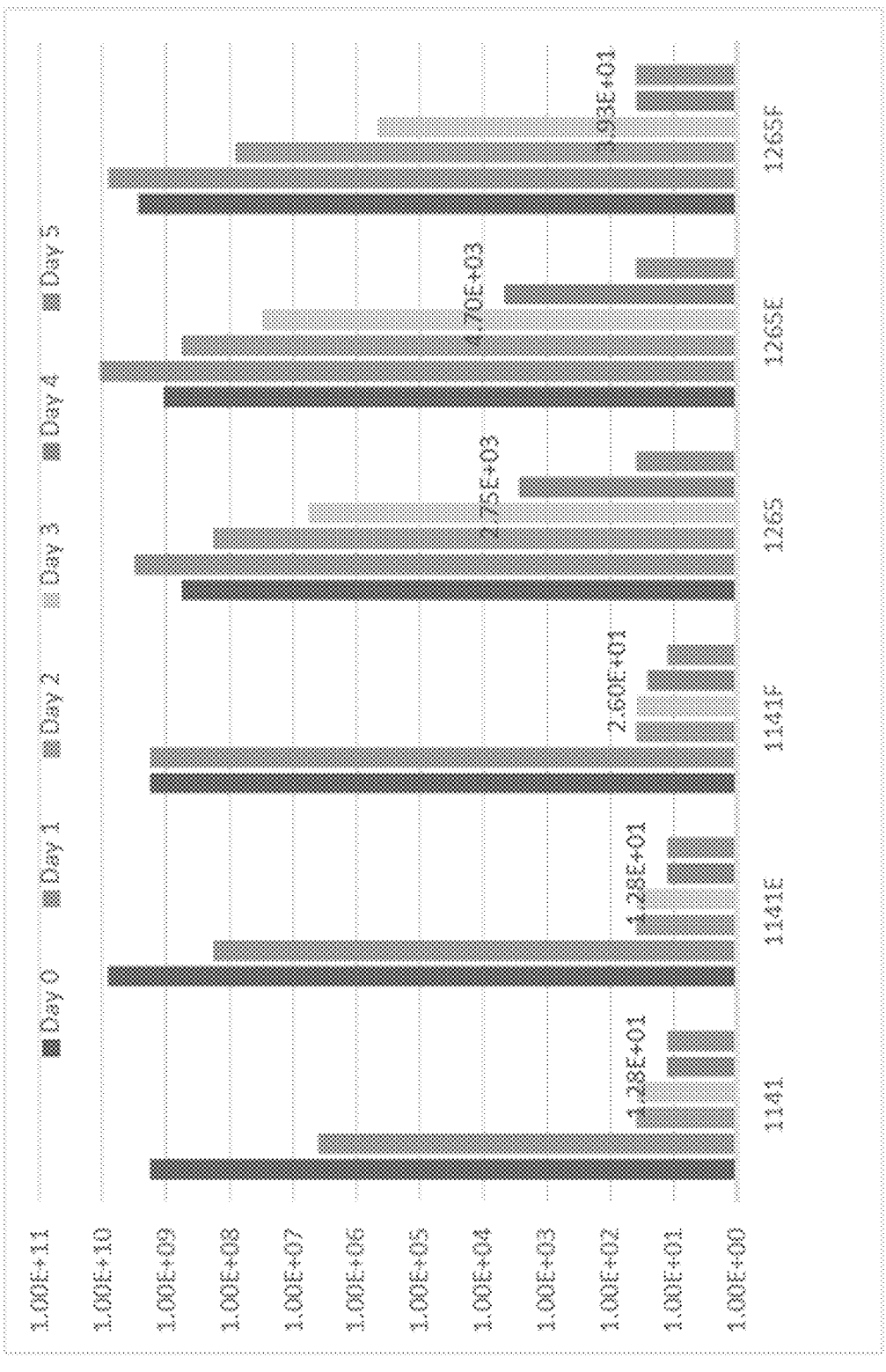
FIG. 1 depicts a bar graph showing MPN assessment of oxygen tolerance of *Megasphaera elsdenii* strain ACD1265 with its parent ACD1009. The overnight cultures of the three *Megasphaera elsdenii* strains were exposed to air for up to 12 days. Day 0 is the anaerobic control without oxygen exposure. Y axis is the cfu/ml calculated by the MPN method.

As described in more detail herein, the inventors have surprisingly discovered several strains of oxygen tolerant *Megasphaera elsdenii*. Compared to the parent strain, the variants showed much improved oxygen tolerance as well as increased viability after oxygen exposure. Without being bound to theory, whole genome sequence comparison of the strains identified nucleotide changes in or near the PerR gene that could have caused the enhanced oxygen-tolerant characteristics. PerR is a transcriptional regulator which has been associated with the oxidative stress response in certain species of bacteria. The oxygen tolerant variant strains *M. elsdenii* retained other desirable properties for use as a DFM, such as the ability to utilize lactate. Additionally, the inventors unexpectedly discovered that the oxygen-tolerant characteristics of the variant strains *M. elsdenii* disclosed herein could further be enhanced by culturing the strains in combination with one or more yeast strains and/or yeast extract.

I. Definitions

The term "gene" refers to a nucleic acid molecule that expresses a specific protein, including regulatory sequences preceding (5' non-coding sequences) and following (3' non-coding sequences) the coding sequence. "Native gene" refers to a gene as found in nature with its own regulatory sequences. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

The term "coding sequence" refers to a nucleotide sequence which codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, RNA processing site, effector binding sites, and stem-loop structures.

The term "operably linked" refers to the association of nucleic acid sequences on a single nucleic acid molecule so that the function of one is affected by the other. For example, a promoter is operably linked with a coding sequence when it is capable of affecting the expression of that coding sequence, i.e., the coding sequence is under the transcriptional control of the promoter. Coding sequences can be operably linked to regulatory sequences in sense or antisense orientation.

The terms "regulatory sequence" or "control sequence" are used interchangeably herein and refer to a segment of a nucleotide sequence which is capable of increasing or decreasing expression of specific genes within an organism. Examples of regulatory sequences include, but are not limited to, promoters, signal sequence, operators and the like. As noted above, regulatory sequences can be operably linked in sense or antisense orientation to the coding sequence/gene of interest.

"Promoter" or "promoter sequences" refer a regulatory sequence that is involved in binding RNA polymerase to initiate transcription of a gene. The promoter may be an inducible promoter or a constitutive promoter. A preferred promoter used in the invention is *Trichoderma reesei* cbh1, which is an inducible promoter.

The "3' non-coding sequences" refer to DNA sequences located downstream of a coding sequence and include sequences encoding regulatory signals capable of affecting mRNA processing or gene expression, such as termination of transcription.

As used herein, "microorganism" or "microbe" refers to a bacterium, a fungus, a virus, a protozoan, and other microbes or microscopic organisms.

The term "anaerobic microorganism" or "anaerobe" as used herein refers to microorganisms which are sensitive to oxygen and will not grow in the presence of oxygen. An anaerobic microorganism or anaerobe is any organism that does not require oxygen for growth. Anaerobic microorganisms include both obligate anaerobes and facultative anaerobes. "Obligate anaerobes" are those microorganisms which will die when exposed to atmospheric levels of oxygen. A "facultative anaerobe" is an organism that can carry out aerobic respiration if oxygen is present, but is capable of switching to fermentation or anaerobic respiration if oxygen is absent.

As used herein, the phrase "oxygen tolerant microorganism" (such as an oxygen tolerant *Megasphaera elsdenii*) refers to a variant of an otherwise anaerobic microorganism that exhibits increased or complete ability to survive (i.e., to remain viable) and/or grow under conditions that include exposure to oxygen (for example, exposure to atmospheric oxygen levels or less than atmospheric oxygen levels, such as any of about 5%, 10%, 15%, 20%, 25%, 30%, 35%, 40%, 45%, 50%, 55%, 60%, 65%, 70%, 75%, 80%, 85%, 90%, 95%, or 100% of atmospheric oxygen, inclusive of all percentages falling in between these values) in comparison to other strains of the same microorganism species which do not possess such oxygen tolerant characteristics and which are unable to survive and/or grow when exposed to oxygen. In one embodiment, an oxygen tolerant microorganism can survive and/or grow under conditions that include exposure to oxygen for about 1-30 days (such as any of about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days).

As used here in the term "direct fed microbial" (DFM) refers to a composition for consumption by animals (i.e. as an or as a component of animal feed) that contains viable microorganisms, i.e. microorganisms that are capable of living and reproducing. See, for example, U.S. Pat. No. 8,420,074. A direct fed microbial may comprise one or more (such as any of 1, 2, 3, 4, 5, or 6 or more) of any of the microbial strains described herein. The terms "probiotic," "probiotic culture," and "DFM" are used interchangeably herein and define live microorganisms (including bacteria or yeasts for example) which, when for example ingested or locally applied in sufficient numbers, beneficially affects the host organism, i.e. by conferring one or more demonstrable health benefits on the host organism such as a health, digestive, and/or performance benefit. Probiotics may improve the microbial balance in one or more mucosal surfaces. For example, the mucosal surface may be the intestine, the urinary tract, the respiratory tract or the skin. The term "probiotic" as used herein also encompasses live microorganisms that can stimulate the beneficial branches of the immune system and at the same time decrease the inflammatory reactions in a mucosal surface, for example the gut. Whilst there are no lower or upper limits for probiotic intake, it has been suggested that at least $10^6$-$10^{12}$, such as at least $10^6$-$10^{10}$, such as $10^8$-$10^9$, cfu as a daily dose will be effective to achieve the beneficial health effects in a subject.

A bacterial "strain" (such as an oxygen tolerant strain of *M. elsdenii*) as used herein refers to a bacterium which remains genetically unchanged when grown or multiplied. The multiplicity of identical bacteria is included.

The term "CFU" as used herein means "colony forming units" and is a measure of viable cells in which a colony represents an aggregate of cells derived from a single progenitor cell.

By "at least one strain," is meant a single strain but also mixtures of strains comprising at least two strains of microorganisms. By "a mixture of at least two strains," is meant a mixture of two, three, four, five, six or even more strains. In some embodiments of a mixture of strains, the proportions can vary from 1% to 99%. When a mixture comprises more than two strains, the strains can be present in substantially equal proportions in the mixture or in different proportions.

For purposes of this disclosure, a "biologically pure strain" means a strain containing no other bacterial strains in quantities sufficient to interfere with replication of the strain or to be detectable by normal bacteriological techniques. "Isolated" when used in connection with the organisms and cultures described herein includes not only a biologically pure strain, but also any culture of organisms which is grown or maintained other than as it is found in nature. In some embodiments, the strains are mutants, variants, or derivatives of strains ACD1265, ACD1096-A01, ACD1096-B01, ACD1096-E01, ACD1096-C02, ACD1096-C05, ACD1096-H05, ACD1096-B03, ACD1141-C10, ACD1141-D10, ACD1141, ACD1141E, ACD1141F, ACD1265E and ACD1265F that also provide benefits comparable to that provided by ACD1265, ACD1096-A01, ACD1096-B01, ACD1096-E01, ACD1096-C02, ACD1096-C05, ACD1096-H05, ACD1096-B03, ACD1141-C10, and ACD1141-D10, ACD1141, ACD1141E, ACD1141F, ACD1265E and ACD1265F. In some embodiments, the strains are strains having all of the identifying characteristics of strains ACD1265, ACD1096-A01, ACD1096-B01, ACD1096-E01, ACD1096-C02, ACD1096-C05, ACD1096-H05, ACD1096-B03, ACD1141-C10, and ACD1141-D10, ACD1141, ACD1141E, ACD1141F, ACD1265E and ACD1265F. Further, each individual strain (ACD1265, ACD1096-A01, ACD1096-B01, ACD1096-E01, ACD1096-C02, ACD1096-C05, ACD1096-H05, ACD1096-B03, ACD1141-C10, and ACD1141-D10, ACD1141, ACD1141E, ACD1141F, ACD1265E and ACD1265F) or any combination of these strains can also provide one or more of the benefits described herein. It will also be clear that addition of other microbial strains, carriers, additives, enzymes, yeast, or the like will also provide one or more benefits or improvement of one or more metrics in an animal and will not constitute a substantially different DFM.

The term "isolated" means a substance in a form or environment that does not occur in nature and does not reflect the extent to which an isolate has been purified, but indicates isolation or separation from a native form or native environment. Non-limiting examples of isolated substances include (1) any non-naturally occurring substance, (2) any substance including, but not limited to, any cell (such as a host cell), enzyme, engineered enzyme, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated.

The term "16S rRNA" or "16S ribosomal RNA" means the rRNA constituting the small subunit of prokaryotic ribosomes. In bacteria, this sequence can be used to identify and characterize operational taxonomic units.

The term "percent identity" is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the number of matching nucleotides or amino acids between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Methods to determine identity and similarity are codified in publicly available computer programs. Percent identity may be determined using standard techniques known in the art. Useful algorithms include the BLAST algorithms (See, Altschul et al., *J Mol Biol*, 215:403-410, 1990; and Karlin and Altschul, *Proc Natl Acad Sci USA*, 90:5873-5787, 1993). The BLAST program uses several search parameters, most of which are set to the default values. The NCBI BLAST algorithm finds the most relevant sequences in terms of biological similarity but is not recommended for query sequences of less than 20 residues (Altschul et al., *Nucleic Acids Res*, 25:3389-3402, 1997; and Schaffer et al., *Nucleic Acids Res*, 29:2994-3005, 2001). Exemplary default BLAST parameters for a nucleic acid sequence searches include: Neighboring words threshold=11; E-value cutoff=10; Scoring Matrix=NUC.3.1 (match=1, mismatch=−3); Gap Opening=5; and Gap Extension=2. Exemplary default BLAST parameters for amino acid sequence searches include: Word size=3; E-value cutoff=10; Scoring Matrix=BLOSUM62; Gap Opening=11; and Gap extension=1.

As used herein with regard to nucleotide or amino acid residue positions, "corresponding to" or "corresponds to" or "correspond to" or "corresponds" refers to (i) a nucleotide or an amino acid residue at an enumerated position in a nucleic acid or a protein or peptide; or (ii) a nucleic acid or an amino acid residue that is analogous, homologous, or equivalent to an enumerated residue in a nucleic acid or a protein or peptide. As used herein, "corresponding region" generally refers to an analogous position in a related protein or a reference protein.

As used herein, "prevent," "preventing," "prevention" and grammatical variations thereof refers to a method of partially or completely delaying or precluding the onset or recurrence of a disorder or condition (such as necrotic enteritis) and/or one or more of its attendant symptoms or barring an animal from acquiring or reacquiring a disorder or condition or reducing an animal's risk of acquiring or reacquiring a disorder or condition or one or more of its attendant symptoms.

As used herein, the term "reducing" in relation to a particular trait, characteristic, feature, biological process, or phenomena refers to a decrease in the particular trait, characteristic, feature, biological process, or phenomena. The trait, characteristic, feature, biological process, or phenomena can be decreased by 5%, 10%, 15%, 20%, 25%, 30%, 35%, 40%, 45%, 50%, 55%, 60%, 65%, 70%, 75%, 80%, 85%, 90%, 95%, 100% or greater than 100%.

The term "ruminant," as used herein, refers to a mammal having a stomach with four chambers. These include a forestomach, comprised of a rumen, a reticulum and an omasum, and a fourth chamber known as an abomasum. Non-limiting examples of ruminants include mammals belonging to the genus Capra, Bos, *Cervus*, and *Ovis*. Ruminants include, without limitation, deer, antelopes, buffalo, cattle (including beef and dairy cattle), sheep, camels, and goats.

"Rumen acidosis," or "acidosis" or "lactic acidosis" as used herein, refer to a metabolic disease of ruminants caused by over-consumption of readily fermentable carbohydrates. Acidosis is typically diagnosed when rumen pH falls below 5.6 for an extended period of time. Acidosis can occur as either acute or subacute. "Acute acidosis" results from rapid starch fermentation which causes the ruminal pH to drastically drop an extended period of time. Symptoms include, without limitation, decreased feed intake, decreased rumination, increased heart rate, increased breathing rate, diarrhea, general lethargy, and death. "Subacute acidosis" refers to the temporary imbalance between acid production and acid removal through absorption and buffering which manifests as multiple occurrences of rumen pH decreasing below 5.6 followed by recovery of pH to above 5.6. Symptoms of prolonged subacute acidosis include, without limitation, reduced feed intake, lower feed efficiency, weight loss or reduced gain, decreased carcass quality, lameness, dehydration, liver abscesses, fever, grain in manure, and diarrhea.

As used herein "administer" or "administering" is meant the action of introducing one or more microbial strain, an exogenous feed enzyme and/or a strain and an exogenous feed enzyme to an animal, such as by feeding or by gavage.

As used herein, "effective amount" means a quantity of DFM and/or exogenous enzymes to improve one or more metrics in an animal. Improvement in one or more metrics of an animal (such as, without limitation, any of increased bodyweight gain, decreased feed conversion ratio (FCR), and/or reduced mortality) can be measured as described herein or by other methods known in the art. An effective amount can be administered to the animal by providing ad libitum access to feed containing the DFM and exogenous enzymes. The DFM and exogenous enzymes can also be administered in one or more doses.

As used herein, the term "feed" is used synonymously herein with "feedstuff." Feed broadly refers to a material, liquid or solid, that is used for nourishing an animal, and for sustaining normal or accelerated growth of an animal including newborns or young and developing animals. The term includes a compound, preparation, mixture, or composition suitable for intake by an animal (such as, e.g., ruminants such as cattle). In some embodiments, a feed or feed composition comprises a basal food composition and one or more feed additives or feed additive compositions. The term "feed additive" as used herein refers to components included for purposes of fortifying basic feed with additional components to promote feed intake, treat or prevent disease, or alter metabolism. Feed additives include pre-mixes.

The term "antioxidant" as used herein refers to a substance that, when present in a mixture or structure containing an oxidizable substrate molecule (e.g., an oxidizable biological molecule), significantly delays or prevents oxidation of the oxidizable substrate molecule. Antioxidants can act by scavenging biologically important reactive free radicals or other reactive oxygen species, or by preventing their formation, or by catalytically converting the free radical or other reactive oxygen species to a less reactive species.

A "premix," as referred to herein, may be a composition composed of micro-ingredients such as, but not limited to, one or more of vitamins, minerals, chemical preservatives, antibiotics, fermentation products, and other essential ingredients. Premixes are usually compositions suitable for blending into commercial rations.

As used herein, "improving one or more metrics in an animal" refers to improvements on measurements relevant to the growth and/or health of an animal (such as a ruminant, for example, a beef or dairy cow), measured by one or more of the following parameters: bodyweight/carcass gain, feed intake, feed conversion (which includes both feed: gain and gain:feed), feed conversion ratio (FCR), decreased medical costs, reduced mortality, reduced transition time from a forage/grass/silage diet to a high concentrate diet, and/or reduced incidence of rumen acidosis. "An improvement in a metric" or "improved metric" as used herein, refers to an improvement in at least one of the parameters listed.

As used herein, a "high concentrate diet" is a diet containing a high level of starch compared to a forage/grass/silage diet.

As used herein, the term "feed conversion ratio" refers to the amount of feed fed to an animal to increase the weight of the animal by a specified amount. An improved feed conversion ratio means a lower feed conversion ratio. By "lower feed conversion ratio" or "improved feed conversion ratio" or "decreased feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number. For example, in connection with a numerical value, the term "about" refers to a range of −10% to +10% of the numerical value, unless the term is otherwise specifically defined in context.

As used herein, the singular terms "a," "an," and "the" include the plural reference unless the context clearly indicates otherwise.

As used herein, "optional" or "optionally" means that the subsequently circumstance or limitation on scope does or does not occur, and that the description includes instances where the circumstance or limitation on scope occurs and instances where it does not. For example, an a composition that optionally contains additional exogenous enzymes means that the enzymes can be present or not present in the composition.

It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is also noted that the term "consisting essentially of," as used herein refers to a composition wherein the component(s) after the term is in the presence of other known component(s) in a total amount that is less than 30% by weight of the total composition and do not contribute to or interferes with the actions or activities of the component(s).

It is further noted that the term "comprising," as used herein, means including, but not limited to, the component(s) after the term "comprising." The component(s) after the term "comprising" are required or mandatory, but the composition comprising the component(s) can further include other non-mandatory or optional component(s).

It is also noted that the term "consisting of," as used herein, means including, and limited to, the component(s) after the term "consisting of." The component(s) after the term "consisting of" are therefore required or mandatory, and no other component(s) are present in the composition.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless defined otherwise herein, all technical and scientific terms used herein have the same meaning as commonly understood by one of ordinary skill in the art to which this invention pertains.

Other definitions of terms may appear throughout the specification.

II. Compositions

A. Strains

Direct fed microbials (DFMs) refer to the feeding of beneficial microbes to animals, such as ruminants, when they are under periods of stress (disease, ration changes, environmental or production challenges) or as a part of a daily nutritional regimen to prevent disease (e.g., acidosis) and facilitate nutrient usage during digestion. "Probiotics" is another term for this category of feed additives. Probiotics or DFMs have been shown to improve animal performance in controlled studies. In some embodiments, DFMs include both direct fed bacteria and/or yeast-based products and, in particular embodiments, include viable microorganisms. The term "viable microorganism" means a microorganism which is metabolically active or able to differentiate and/or reproduce.

DFM-containing compositions (such as feed additive compositions, premix compositions, kits, feeds, feedstuffs, or biologically pure compositions) can include those that contain one or more strains (such as any of about 1, 2, 3, 4, 5, 6, 7, 8, 9, or 10 or more strains) of an oxygen tolerant *Megasphaera elsdenii. Megasphaera elsdenii* (i.e., *M. elsdenii*) is an anaerobic non-motile gram-negative diplococcus that utilizes lactate as a preferred carbon source and which is commonly found in the digestive tract of ruminant animals. *Megasphaera elsdenii* is the major lactate-utilizing organisms in the rumen of adapted cattle fed high grain diets. When cattle are shifted from high forage to high concentrate diet, the numbers of *M. elsdenii* are often insufficient to prevent a condition called lactic acidosis (see, e.g., U.S. Pat. App. Pub. No. 2009/0246177, incorporated by reference herein).

The oxygen-tolerant *M. elsdenii* strains provided herein for use in the described compositions, methods, and kits include *M. elsdenii* ACD1265, *M. elsdenii* ACD1096-A01, *M. elsdenii* ACD1096-B01, *M. elsdenii* ACD1096-E01, *M. elsdenii* ACD1096-C02, *M. elsdenii* ACD1096-C05, *M. elsdenii* ACD1096-H05, *M. elsdenii* ACD1096-B03, *M. elsdenii* ACD1141-C10, *M. elsdenii* ACD1141-D10, *M. elsdenii* ACD1141, *M. elsdenii* ACD1141E, *M. elsdenii* ACD1141F, *M. elsdenii* ACD1265E, and *M. elsdenii* ACD1265F which are also referred to herein as ACD1265, ACD1096-A01, ACD1096-B01, ACD1096-E01, ACD1096-C02, ACD1096-C05, ACD1096-H05, ACD1096-B03, ACD1141-C10, and ACD1141-D10, ACD1141, ACD1141E, ACD1141F, ACD1265E, and ACD1265F, respectively. *M. elsdenii* ACD1265, *M. elsdenii* ACD1141, *M. elsdenii* ACD1141E, *M. elsdenii* ACD1141F, *M. elsdenii* ACD1265E, and *M. elsdenii* ACD1265F were deposited on Dec. 18, 2019 at the Westerdijk Fungal Biodiversity Institute (WFDI), Uppsalalaan 8, 3584 CT, Utrecht, The Netherlands and given accession numbers CBS 146328, CBS 146325, CBS 146326, CBS 146327, CBS 146329, and CBS 146330, respectively. The deposits were made under the provisions of the Budapest Treaty on the International Recognition of the Deposit of Microorganisms for the Purposes of Patent Procedure. One or more strain provided herein can be used as a direct-fed microbial (DFM).

In some non-limiting embodiments, one or more of the oxygen tolerant *Megasphaera elsdenii* strains disclosed herein are non-naturally occurring (i.e. are not found in nature).

In some embodiments, additional *M. elsdenii* cells suitable for use in the compositions, methods, or kits disclosed herein are from a strain having a deposit number selected from the group consisting of: ATCC® 25940, ATCC® 17752, ATCC® 17753, NCIMB 702261, NCIMB 702262, NCIMB 702264, NCIMB 702331, NCIMB 702409, NCIMB 702410, NCIMB 41787, NCIMB 41788, NRRL 18624, NIAH 1 102, and a biologically pure bacterial culture of *M. elsdenii* having substantially the same 16S ribosomal RNA sequence as that of the *M. elsdenii* strain deposited on Mar. 18, 2002 at NCIMB, Aberdeen, Scotland, UK under number NCIMB 41125.

Any of the *M. elsdenii* (including both oxygen-tolerant *M. elsdenii* and/or oxygen intolerant *M. elsdenii*)-containing compositions (such as feed additive compositions) disclosed herein can further include one or more strains (such as any of about 1, 2, 3, 4, 5, 6, 7, or 8 or more strains) of yeast. When cultured together with one or more yeast strains and/or yeast extract, one or more *M. elsdenii* strains have one or more physiological or metabolic properties that individually cultured *M. elsdenii* strains lack. These properties can include, without limitation, changes in the amount and/or type of metabolite produced or metabolized, change in metabolic profile (such as, without limitation, lactate utilization), and/or a change in the ability of the one or more *M. elsdenii* strains to grow and remain viable in the presence of oxygen. Suitable yeast for use in the compositions and methods disclosed herein include, without limitation, those from the genus *Saccharomyces* (e.g., *S. cerevisiae*) or *Pichia* (e.g., *P. kudriavzevii*) or certain species of fungi (e.g., fungi from the genus *Aspergillus*, such as *A. oryzae*). Commercially available yeasts for use in any of the *M. elsdenii*-containing compositions (such as feed additive compositions), methods, or kits disclosed herein can further include, without limitation, Ethanol red (LESaffre), Zenith thermostable yeast or Zenith yeast concentrate (FLEISCHMANNS YEAST (AB Mauri)), Saf-instant or Saf-instant Gold (LeSaffre), Fleischmann's Instant Dry Yeast (FLEISCHMANNS YEAST (AB Mauri)), Red Star (LeSaffre), Instant Yeast HS 2141 or Instant Yeast 2174 ((FLEISCHMANNS YEAST (AB Mauri)), or Summit Ethanol dry yeast 6007 (AB Mauri).

In other embodiments, the yeast can be from the genus *Pichia*. Non-limiting examples include *Pichia* kudriavzevii, *Candida krusei, Saccharomyces krusei, Endomyces krusei, Monilia krusei, Candida krusei, Myceloblastanon krusei, Geotrichoides krusei, Trichosporon krusei, Mycotoruloides krusei, Enantiothamnus braulti, Blastodendrion braulti, Monilia parakrusei, Myceloblastanon parakrusei, Castellania parakrusei, Candida parakrusei, Mycoderma chevalieri, Candida chevalieri, Mycoderma monosa, Mycoderma bordetii, Monilia inexpectata, Mycocandida inexpectata, Pseudomonilia inexpectata, Trichosporon dendriticum, Candida dendritica, Castellania africana, Castellania balcanica, Monilia krusoides, Pseudomycoderma miso, Candida castellanii, Candida tamarindi, Procandida tamarindii, Issatchenkia orientalis, Candida lobate, Endoblastomyces thermophilus, Candida requinyii, Candida soosii, Pichia orientalis, Candida acidothermophilum, Candida brassicae, Candida ethanothermophilum, Candida melinii, Candida hinoensis,* or *Candida solicola.*

In some embodiments, one or more yeast strains is present in the composition at a concentration of about $10^7$ CFU/g to about $10^{10}$ CFU/g, such as any of about $10^7$ CFU/g, $10^8$ CFU/g, $10^9$ CFU/g, or $10^{10}$ CFU/g.

In other embodiments, the ratio of *M. elsdenii* (such as any of the oxygen-tolerant *M. elsdenii* strains disclosed herein) microbes to yeast microbes in the composition can include 1:1 to 1:10, such as any of 1:1, 1:2, 1:3, 1:4, 1:5, 1:6, 1:7, 1:8, 1:9, or 1:10 as determined by CFU.

In some embodiments, any of the oxygen-tolerant *M. elsdenii* strains disclosed herein can contain at least one mutation in a gene encoding the transcriptional regulator PerR (such as the PerR gene encoded by SEQ ID NO:4); or immediately upstream of the gene encoding the transcriptional regulator PerR. As used herein, the terms "mutation" or "substitution" are used interchangeably to denote a change in a nucleotide or amino acid sequence that does not naturally occur in a corresponding wildtype nucleotide or amino acid sequence. PerR, is a metalloregulator belonging to the Fur family of regulators which can function as a specific sensor of $H_2O_2$. Specifically, when bound to DNA, PerR represses the genes coding for peroxide defense enzymes (katA, ahpC), DNA-protecting protein (mrgA), metal homeostasis proteins (hemAXCDBL, fur, zosA) and its own synthesis (perR) (Duarte & Latour, Future Med. Chem, (2013) 5 (11), 1177-1179). It has also been shown that deletion of a peroxide repressor (PerR)-homologous protein in *C. acetobutylicum* resulted in prolonged acrotolerance, limited growth under aerobic conditions, higher resistance to $H_2O_2$, and rapid consumption of oxygen (Hillmann et al., 2008, *Molecular Microbiology* 68:848-60).

The PerR gene in any of the disclosed oxygen-tolerant *M. elsdenii* strains can have one or more mutations (such as any of 1, 2, 3, 4, 5, 6, 7, 8, 9, 10, 11, 12, 13, 14, 15, 16, 17, 18, 19, or 20 or more) that either prevent expression of the PerR polypeptide (such as the polypeptide of SEQ ID NO: 6) or which renders the PerR polypeptide non-functional or with decreased functionality (such as about 10%, 20%, 30%, 40%, 50%, 60%, 70%, 80%, or 90% decreased functionality, including all percentages between these values) relative to the functionality of a non-mutated (i.e. wildtype) PerR polypeptide. The mutation can be located within the gene itself (e.g., within an intron or an exon) or upstream of the gene in a transcriptional regulatory region (such as from about-1 to about-200 nucleotides upstream from the gene's start codon). Corresponding to the nucleic acid sequence in SEQ ID NO:4, the PerR gene in any of the disclosed oxygen-tolerant *M. elsdenii* strains can have mutations at one or more of position 386 (such as G386T), 155 (such as C155T), 253 (such as C253T), −99 (where "-" denotes nucleotides upstream from the start codon of the PerR gene; such as T-99C), and/or −125 (such as G-125A). In further embodiments, the mutation can be an insertion of a nucleotide into the gene and/or transcriptional regulatory sequences that results in a frameshift mutation (such as a nonsense or a missense mutation). In some embodiments, the nucleotide insertion can be at a nucleotide position such as 30 (such as an A inserted at position 30), 277 (such as an A inserted at position 277), and/or 64 (such as a G inserted at position 64) where the nucleotide positions correspond to SEQ ID NO:4.

B. Exogenous Enzymes

Supplemental enzymes can be used as additives to animal feed, particularly poultry and swine feeds, as a means to improve nutrient utilization and performance characteristics. In one embodiment, the disclosure relates to a composition comprising one or more oxygen-tolerant *M. elsdenii* strains (such as DFMs containing any of the oxygen-tolerant *M. elsdenii* strains disclosed herein) and one or more exogenous feed enzymes. In another embodiment, the disclosure relates to a composition comprising, consisting of, or consisting essentially of one or more oxygen-tolerant *M. elsdenii* strains disclosed herein, one or more yeast strains and/or yeast extract, and one or more exogenous feed enzymes. In one embodiment, the exogenous feed enzymes include, but are not limited to, xylanase, amylase, phytase, beta-glucanase, and protease. In still another embodiment, the composition comprises a feed additive.

1. Xylanases

Xylanase is the name given to a class of enzymes that degrade the linear polysaccharide β-1,4-xylan into xylose, thus breaking down hemicellulose, one of the major components of plant cell walls. Xylanases, e.g., endo-β-xylanases (EC 3.2.1.8) hydrolyze the xylan backbone chain. In one embodiment, provided herein are compositions comprising any of the oxygen-tolerant *M. elsdenii* strain compositions disclosed herein and one or more xylanase. In a further embodiment, the composition further comprises one or more yeast strains and/or yeast extract.

In one embodiment, the xylanase may be any commercially available xylanase. Suitably the xylanase may be an endo-1,4-P-d-xylanase (classified as EC 3.2.1.8) or a 1,4β-xylosidase (classified as EC 3.2.1.37). In one embodiment, the disclosure relates to a DFM in combination with an endoxylanase, e.g. an endo-1,4-P-d-xylanase, and another enzyme. All E.C. enzyme classifications referred to herein relate to the classifications provided in Enzyme Nomenclature—Recommendations (1992) of the nomenclature committee of the International Union of Biochemistry and Molecular Biology—ISBN 0-12-226164-3, which is incorporated herein In another embodiment, the xylanase may be a xylanase from *Bacillus, Trichodermna, Therinomyces, Aspergillus* and *Penicillium*. In still another embodiment, the xylanase may be the xylanase in Axtra XAP® or Avizyme 1502®, both commercially available products from Danisco A/S. In one embodiment, the xylanase may be a mixture of two or more xylanases. In still another embodiment, the xylanase is an endo-1,4-β-xylanase or a 1,4-β-xylosidase. In yet another embodiment, the xylanase is from an organism selected from the group consisting of: *Bacillus, Trichoderma, Thermomyces, Aspergillus, Penicillium*, and *Humicola*.

In one embodiment, the disclosure relates to a composition comprising an oxygen tolerant *M. elsdenii* strain (such as any of the oxygen tolerant *M. elsdenii* strains disclosed herein) and xylanase. In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 xylanase units/g of composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, and greater than 8000 xylanase units/g composition.

It will be understood that one xylanase unit (XU) is the amount of enzyme that releases 0.5 μmol of reducing sugar equivalents (as xylose by the Dinitrosalicylic acid (DNS) assay-reducing sugar method) from an oat-spelt-xylan substrate per min at pH 5.3 and 50° C. (Bailey, et al., *Journal of Biotechnology*, Volume 23, (3), May 1992, 257-270).

2. Amylases

Amylase is a class of enzymes capable of hydrolysing starch to shorter-chain oligosaccharides, such as maltose. The glucose moiety can then be more easily transferred from maltose to a monoglyceride or glycosylmonoglyceride than from the original starch molecule. The term amylase includes α-amylases (E.G. 3.2.1.1), G4-forming amylases (E.G. 3.2.1.60), β-amylases (E.G. 3.2.1.2) and γ-amylases (E.C. 3.2.1.3). Amylases may be of bacterial or fungal origin, or chemically modified or protein engineered mutants. In one embodiment, provided herein are compositions comprising any of the oxygen-tolerant *M. elsdenii* strain compositions disclosed herein and one or more amylase. In a further embodiment, the composition further comprises one or more yeast strains and/or yeast extract.

In one embodiment, the amylase may be a mixture of two or more amylases. In another embodiment, the amylase may be an amylase, e.g. an α-amylase, from *Bacillus licheniformis* and an amylase, e.g. an α-amylase, from *Bacillus amyloliquefaciens*. In one embodiment, the α-amylase may be the α-amylase in Axtra XAP® or Avizyme 1502®, both commercially available products from Danisco A/S. In yet another embodiment, the amylase may be a pepsin resistant α-amylase, such as a pepsin resistant *Trichoderma* (such as *Trichoderma reesei*) alpha amylase. A suitably pepsin resistant α-amylase is taught in UK application number 101 1513.7 (which is incorporated herein by reference) and PCT/IB2011/053018 (which is incorporated herein by reference).

It will be understood that one amylase unit (AU) is the amount of enzyme that releases 1 mmol of glucosidic linkages from a water insoluble cross-linked starch polymer substrate per min at pH 6.5 and 37° C. (this may be referred to herein as the assay for determining 1 AU).

In one embodiment, disclosure relates to a composition comprising an oxygen tolerant *M. elsdenii* strain (such as any of the oxygen tolerant *M. elsdenii* strains disclosed herein) and an amylase. In one embodiment, disclosure relates to a composition comprising a multi-strain DFM, xylanase and amylase. In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 amylase units/g composition.

In one embodiment, the composition comprises 500-1000, 1000-1500, 1500-2000, 2000-2500, 2500-3000, 3000-

3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000 and greater than 15000 amylase units/g composition.

3. Proteases

The term protease as used herein is synonymous with peptidase or proteinase. The protease may be a subtilisin (E.G. 3.4.21.62) or a bacillolysin (E.G. 3.4.24.28) or an alkaline serine protease (E.G. 3.4.21.x) or a keratinase (E.G. 3.4.X.X). In one embodiment, the protease is a subtilisin. Suitable proteases include those of animal, vegetable or microbial origin. Chemically modified or protein engineered mutants are also suitable. The protease may be a serine protease or a metalloprotease. e.g., an alkaline microbial protease or a trypsin-like protease. In one embodiment, provided herein are compositions comprising any of the oxygen-tolerant *M. elsdenii* strain compositions disclosed herein and one or more protease. In a further embodiment, the composition further comprises one or more yeast strains and/or yeast extract.

Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115.

In one embodiment, the protease is selected from the group consisting of subtilisin, a bacillolysin, an alkine serine protease, a keratinase, and a Nocardiopsis protease.

It will be understood that one protease unit (PU) is the amount of enzyme that liberates from the substrate (0.6% casein solution) one microgram of phenolic compound (expressed as tyrosine equivalents) in one minute at pH 7.5 (40 mM Na2PO4/lactic acid buffer) and 40° C. This may be referred to as the assay for determining 1 PU.

In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 protease units/g composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000 and greater than 15000 protease units/g composition.

4. Phytases

In one embodiment, provided herein are compositions comprising any of the oxygen-tolerant *M. elsdenii* strain compositions disclosed herein and one or more phytase. In a further embodiment, the composition further comprises one or more yeast strains and/or yeast extract. The phytase for use in the present invention may be classified a 6-phytase (classified as E.C. 3.1.3.26) or a 3-phytase (classified as E.C. 3.1.3.8).

In one embodiment the phytase is a *Citrobacter* phytase derived from e.g. *Citrobacter freundii*, preferably *C. freundii* NCIMB 41247 and variants thereof e.g. as disclosed in WO2006/038062 (incorporated herein by reference) and WO2006/038128 (incorporated herein by reference), *Citrobacter* braakii YH-15 as disclosed in WO 2004/085638, *Citrobacter* braakii ATCC 51113 as disclosed in WO2006/

037328 (incorporated herein by reference), as well as variants thereof e.g. as disclosed in WO2007/112739 (incorporated herein by reference) and WO2011/117396 (incorporated herein by reference), *Citrobacter amalonaticus*, preferably *Citrobacter amalonaticus* ATCC 25405 or *Citrobacter amalonaticus* ATCC 25407 as disclosed in WO2006037327 (incorporated herein by reference), *Citrobacter gillenii*, preferably *Citrobacter gillenii* DSM 13694 as disclosed in WO2006037327 (incorporated herein by reference), or *Citrobacter intermedius, Citrobacter koseri, Citrobacter murliniae, Citrobacter rodentium, Citrobacter sedlakii, Citrobacter werkmanii, Citrobacter youngae, Citrobacter* species polypeptides or variants thereof.

In some embodiments, the phytase is an *E. coli* phytase marketed under the name Phyzyme XP™ Danisco A/S. Alternatively, the phytase may be a *Buttiauxella* phytase, e.g. a *Buttiauxella agrestis* phytase, for example, the phytase enzymes taught in WO 2006/043178, WO 2008/097619, WO2009/129489, WO2008/092901, PCT/US2009/41011 or PCT/IB2010/051804, all of which are incorporated herein by reference.

In one embodiment, the phytase may be a phytase from *Hafnia*, e.g. from *Hafnia alvei*, such as the phytase enzyme(s) taught in US2008263688, which reference is incorporated herein by reference. In one embodiment, the phytase may be a phytase from *Aspergillus*, e.g. from *Apergillus orzyae*. In one embodiment, the phytase may be a phytase from *Penicillium*, e.g. from *Penicillium funiculosum*.

Preferably, the phytase is present in the feedstuff in range of about 200 FTU/kg to about 1000 FTU/kg feed, more preferably about 300 FTU/kg feed to about 750 FTU/kg feed, more preferably about 400 FTU/kg feed to about 500 FTU/kg feed. In one embodiment, the phytase is present in the feedstuff at more than about 200 FTU/kg feed, suitably more than about 300 FTU/kg feed, suitably more than about 400 FTU/kg feed. In one embodiment, the phytase is present in the feedstuff at less than about 1000 FTU/kg feed, suitably less than about 750 FTU/kg feed. Preferably, the phytase is present in the feed additive composition in range of about 40 FTU/g to about 40,000 FTU/g composition, more preferably about 80 FTU/g composition to about 20,000 FTU/g composition, and even more preferably about 100 FTU/g composition to about 10,000 FTU/g composition, and even more preferably about 200 FTU/g composition to about 10,000 FTU/g composition. In one embodiment, the phytase is present in the feed additive composition at more than about 40 FTU/g composition, suitably more than about 60 FTU/g composition, suitably more than about 100 FTU/g composition, suitably more than about 150 FTU/g composition, suitably more than about 200 FTU/g composition. In one embodiment, the phytase is present in the feed additive composition at less than about 40,000 FTU/g composition, suitably less than about 20,000 FTU/g composition, suitably less than about 15,000 FTU/g composition, suitably less than about 10,000 FTU/g composition.

It will be understood that as used herein 1 FTU (phytase unit) is defined as the amount of enzyme required to release 1 µmol of inorganic orthophosphate from a substrate in one minute under the reaction conditions defined in the ISO 2009 phytase assay—A standard assay for determining phytase activity and 1 FTU can be found at International Standard ISO/DIS 30024:1-17, 2009. In one embodiment, the enzyme is classified using the E.C. classification above, and the E.C. classification designates an enzyme having that activity when tested in the assay taught herein for determining 1 FTU.

In one embodiment, disclosure relates to a composition comprising an oxygen tolerant *M. elsdenii* strain (such as any of the oxygen tolerant *M. elsdenii* strains disclosed herein and optionally one or more yeast strains and/or yeast extract) and a protease. In another embodiment, disclosure relates to a composition comprising an oxygen tolerant *M. elsdenii* strain (such as any of the oxygen tolerant *M. elsdenii* strains disclosed herein and optionally one or more yeast strains and/or yeast extract) and a xylanase and a protease. In still another embodiment, the disclosure relates to a composition comprising an oxygen tolerant *M. elsdenii* strain (such as any of the oxygen tolerant *M. elsdenii* strains disclosed herein and optionally one or more yeast strains and/or yeast extract) and an amylase and a protease. In still another embodiment, the disclosure relates to a composition comprising an oxygen tolerant *M. elsdenii* strain (such as any of the oxygen tolerant *M. elsdenii* strains disclosed herein and optionally one or more yeast strains and/or yeast extract) and a protease and a phytase. In still another embodiment, the disclosure relates to a composition comprising an oxygen tolerant *M. elsdenii* strain (such as any of the oxygen tolerant *M. elsdenii* strains disclosed herein and optionally one or more yeast strains and/or yeast extract) and a xylanase and an amylase. In still another embodiment, the disclosure relates to a composition comprising an oxygen tolerant *M. elsdenii* strain (such as any of the oxygen tolerant *M. elsdenii* strains disclosed herein and optionally one or more yeast strains and/or yeast extract) and a xylanase and a phytase. In still another embodiment, the disclosure relates to a composition comprising an oxygen tolerant *M. elsdenii* strain (such as any of the oxygen tolerant *M. elsdenii* strains disclosed herein and optionally one or more yeast strains and/or yeast extract) and an amylase and a phytase. In yet another embodiment, the disclosure relates to a composition comprising an oxygen tolerant *M. elsdenii* strain (such as any of the oxygen tolerant *M. elsdenii* strains disclosed herein and optionally one or more yeast strains and/or yeast extract) and a xylanase, an amylase and a protease. In still another embodiment, the disclosure relates to a composition comprising an oxygen tolerant *M. elsdenii* strain (such as any of the oxygen tolerant *M. elsdenii* strains disclosed herein and optionally one or more yeast strains and/or yeast extract) and a protease, a xylanase, and a phytase. In still another embodiment, the disclosure relates to a composition comprising an oxygen tolerant *M. elsdenii* strain (such as any of the oxygen tolerant *M. elsdenii* strains disclosed herein and optionally one or more yeast strains and/or yeast extract) and an amylase, a xylanase, and a phytase. In still another embodiment, the disclosure relates to a composition comprising an oxygen tolerant *M. elsdenii* strain (such as any of the oxygen tolerant *M. elsdenii* strains disclosed herein and optionally one or more yeast strains and/or yeast extract) and an amylase, a protease, a xylanase, and a phytase.

C. DFM Formulations

In one embodiment, any of the oxygen tolerant *M. elsdenii* DFMs (or DFM-containing compositions disclosed herein) and, optionally, one or more yeast strains and/or yeast extract, and further optionally, one or more exogenous enzymes may be formulated as a liquid, a dry powder or a granule. In one embodiment, the oxygen tolerant *M. elsdenii* DFMs and exogenous enzymes can be formulated as a single mixture. In another embodiment, the oxygen tolerant *M. elsdenii* DFMs and the exogenous enzymes can be formulated as separate mixtures. In still another embodiment, separate mixtures of oxygen tolerant *M. elsdenii* DFMs and the exogenous enzymes can be administered at the same time or at different times. In still another embodiment, separate mixtures of oxygen tolerant *M. elsdenii* DFMs and the exogenous enzymes can be administered simultaneously or sequentially. In yet another embodiment, a first mixture comprising oxygen tolerant *M. elsdenii* DFMs can be administered followed by a second mixture comprising exogenous enzymes. In still another embodiment, a first mixture comprising exogenous enzymes can be administered followed by a second mixture comprising oxygen tolerant *M. elsdenii* DFMs.

The dry powder or granules may be prepared by means known to those skilled in the art, such as, in top-spray fluid bed coater, in a buttom spray Wurster or by drum granulation (e.g. High sheer granulation), extrusion, pan coating, oil dispersion, or in a microingredients mixer. In other embodiments, the granules can be prepared by water application or drench application.

In another embodiment, the oxygen tolerant *M. elsdenii* DFMs (and optionally one or more yeast strains and/or yeast extract) and/or the enzyme(s) may be coated, for example encapsulated. Suitably the oxygen tolerant *M. elsdenii* DFMs and enzymes may be formulated within the same coating or encapsulated within the same capsule. Alternatively, one or more of the enzymes may be formulated within the same coating or encapsulated within the same capsule while the DFM can be formulated in a separate coating from the enzymes.

In some embodiments, the oxygen tolerant *M. elsdenii* DFMs (and optionally one or more yeast strains and/or yeast extract) may be provided without any coating. In such circumstances, the DFMs may be simply admixed with one or more enzymes. In other embodiments, the DFMs or the enzymes may be coated, e.g. encapsulated, for instance one or more or all of the enzymes may be coated, e.g. encapsulated. The enzymes may be encapsulated as mixtures (i.e. comprising one or more, two or more, three or more or all) of enzymes or they may be encapsulated separately, e.g. as single enzymes. In one preferred embodiment, all enzymes may be coated, e.g. encapsulated, together. In one embodiment, the coating protects the enzymes from heat and may be considered a thermoprotectant.

In another embodiment, the oxygen tolerant *M. elsdenii* DFMs (and optionally one or more yeast strains and/or yeast extract) and exogenous feed enzymes may be mixed with feed or administered in the drinking water. In one embodiment, the dosage range for inclusion into water is about $1 \times 10^3$ CFU/animal/day to about $1 \times 10^{10}$ CFU/animal/day, for example, about $1 \times 10^7$ CFU/animal/day.

Additionally, any of the oxygen tolerant *M. elsdenii* DFMs (and optionally one or more yeast strains and/or yeast extract) can further be formulated in conjunction with one or more additional DFMs. A additional DFM as described herein may comprise microorganisms from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* and combinations thereof.

In one embodiment, the additional DFM comprises one or more bacterial strains selected from the following *Bacillus* spp: *Bacillus subtilis, Bacillus cereus, Bacillus licheniformis, Bacillus velezensis, Bacillus pumilis* and *Bacillus amyloliquefaciens*.

The genus "*Bacillus*", as used herein, includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megate-*

*rium, B. coagulans, B. circulans, B. gibsonii, B. pumilis, B. velezensis,* and *B. thuringiensis.* It is recognized that the genus *Bacillus* continues to undergo taxonomical reorganization. Thus, it is intended that the genus include species that have been reclassified, including but not limited to such organisms as *Bacillus stearothermophilus,* which is now named "*Geobacillus stearothermophilus*", or *Bacillus polymyxa,* which is now "*Paenibacillus polymyxa*" The production of resistant endospores under stressful environmental conditions is considered the defining feature of the genus *Bacillus,* although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus.*

In another aspect, the oxygen tolerant *M. elsdenii* DFMs (and optionally one or more yeast strains and/or yeast extract) may be further combined with the following *Lactococcus* spp: *Lactococcus cremoris* and *Lactococcus lactis* and combinations thereof.

The oxygen tolerant *M. elsdenii* DFMs (and optionally one or more yeast strains and/or yeast extract) may be further combined with the following *Lactobacillus* spp: *Lactobacillus buchneri, Lactobacillus acidophilus, Lactobacillus casei, Lactobacillus kefiri, Lactobacillus bifidus, Lactobacillus brevis, Lactobacillus helveticus, Lactobacillus paracasei, Lactobacillus rhamnosus, Lactobacillus salivarius, Lactobacillus curvatus, Lactobacillus bulgaricus, Lactobacillus sakei, Lactobacillus reuteri, Lactobacillus fermentum, Lactobacillus farciminis, Lactobacillus lactis, Lactobacillus delbrueckii, Lactobacillus plantarum, Lactobacillus paraplantarum, Lactobacillus farciminis, Lactobacillus rhamnosus, Lactobacillus crispatus, Lactobacillus gasseri, Lactobacillus johnsonii* and *Lactobacillus jensenii,* and combinations of any thereof.

Many of the DFM strains disclosed herein are found in the genus *Lactobacillus.* As of March 2020, Lactobacilli comprised 261 species that are extremely diverse phenotypically, ecologically, and genotypically. Given recent advances in whole genome sequencing and comparative genomics, the genus *Lactobacillus* was recently divided into 25 separate genera with strains belonging to previously designated Lactobacilli species being transferred to new species and/or genera (see Zheng et al., 2020, *Int. J. Syst. Evol. Microbiol.,* 70:2782-2858; Pot et al., *Trends in Food Science & Technology* 94 (2019) 105-113; and Koutsoumanis et al., 2020, *EFSA Journal,* 18 (7): 6174, the disclosures of each of which are incorporated by reference herein). For purposes of the instant disclosure, the previous classification of *Lactobacillus* species will continue to be employed. However, in some embodiments *Lactobacillus agilis* is also classified as as Ligilactobacillus *agilis.* In other embodiments, *Lactobacillus salivarius* is also classified as Ligilactobacillus *salivarius.* In further embodiments, *Lactobacillus reuteri* is also classified as Limosilactobacillus *reuteri.*

In still another aspect, the oxygen tolerant *M. elsdenii* DFMs (and optionally one or more yeast strains and/or yeast extract) may be further combined with the following Bifidobacteria spp: *Bifidobacterium lactis, Bifidobacterium bifidium, Bifidobacterium longum, Bifidobacterium animalis, Bifidobacterium breve, Bifidobacterium infantis, Bifidobacterium catenulatum, Bifidobacterium pseudocatenulatum, Bifidobacterium adolescentis,* and *Bifidobacterium angulatum,* and combinations of any thereof.

Alternatively, oxygen tolerant *M. elsdenii* DFMs (and optionally one or more yeast strains and/or yeast extract) may be combined with one or more of the products or the microorganisms contained in those products disclosed in WO2012110778, and summarized as follows: *Bacillus subtilis* (reclassified as *Bacillus velezensis*) strain 2084 Accession No. NRRLB-50013, *Bacillus subtilis* (reclassified as *Bacillus velezensis*) strain LSSAO1 Accession No. NRRL B-50104, and *Bacillus subtilis* (reclassified as *Bacillus velezensis*) strain 15A-P4 ATCC Accession No. PTA-6507 (from Enviva Pro®. (formerly known as Avicorr®); *Bacillus subtilis* Strain C3102 (from Calsporin®); *Bacillus subtilis* Strain PB6 (from Clostat®); *Bacillus pumilis* (8G-134); *Enterococcus* NCIMB 10415 (SF68) (from Cylactin®); *Bacillus subtilis* Strain C3102 (from Gallipro® & Gallipro-Max®); *Bacillus licheniformis* (from Gallipro®Tect®); *Enterococcus* and *Pediococcus* (from Poultry Star®); *Lactobacillus, Bifidobacterium* and/or *Enterococcus* from Protexin®); *Bacillus subtilis* strain QST 713 (from Proflora®); *Bacillus amyloliquefaciens* CECT-5940 (from Ecobiol® & Ecobiol® Plus); *Enterococcus faecium* SF68 (from Fortiflora®); *Bacillus subtilis* and *Bacillus licheniformis* (from BioPlus2B®); Lactic acid bacteria 7 *Enterococcus faecium* (from Lactiferm®); *Bacillus* strain (from CSI®); *Saccharomyces cerevisiae* (from Yea-Sacc®); *Enterococcus* (from Biomin IMB52®); *Pediococcus acidilactici, Enterococcus, Bifidobacterium animalis* ssp. *animalis, Lactobacillus reuteri, Lactobacillus salivarius* ssp. *salivarius* (from Biomin C5®); *Lactobacillus farciminis* (from Biacton®); *Enterococcus* (from Oralin E1707®); *Enterococcus* (2 strains), *Lactococcus lactis* DSM 1103 (from Probios-pioneer PDFM®); *Lactobacillus rhamnosus* and *Lactobacillus farciminis* (from Sorbiflore®); *Bacillus subtilis* (from Animavit®); *Enterococcus* (from Bonvital®); *Saccharomyces cerevisiae* (from Levucell SB 20®); *Saccharomyces cerevisiae* (from Levucell SC 0 & SC10® ME); *Pediococcus acidilacti* (from Bactocell); *Saccharomyces cerevisiae* (from ActiSaf® (formerly BioSaf®)); *Saccharomyces cerevisiae* NCYC Sc47 (from Actisaf® SC47); *Clostridium butyricum* (from Miya-Gold®); *Enterococcus* (from Fecinor and Fccinor Plus®); *Saccharomyces cerevisiae* NCYC R-625 (from InteSwine®); *Saccharomyces cerevisia* (from BioSprint®); *Enterococcus* and *Lactobacillus rhamnosus* (from Provita®); *Bacillus subtilis* and *Aspergillus oryzae* (from PepSoyGen-C®); *Bacillus cereus* (from Toyocerin®); *Bacillus cereus* var. *toyoi* NCIMB 40112/CNCM I-1012 (from TOYOCERIN®), or other DFMs such as *Bacillus licheniformis* and *Bacillus subtilis* (from BioPlus® YC), *Bacillus subtilis* (from GalliPro®), and *Megasphaera elsdenii* NCIMB41125 from LactiPro®.

The oxygen tolerant *M. elsdenii* DFMs (and optionally one or more yeast strains and/or yeast extract) may be combined with Enviva® PRO which is commercially available from Danisco A/S. Enviva Pro® is a combination of *Bacillus* strain 2084 Accession No. NRRL B-50013, *Bacillus* strain LSSAO1 Accession No. NRRL B-50104 and *Bacillus* strain 15A-P4 ATCC Accession No. PTA-6507 (as taught in U.S. Pat. No. 7,754,469 B—incorporated herein by reference).

Preferably, the additional DFM described herein comprises microorganisms which are generally recognized as safe (GRAS) and, preferably are GRAS-approved.

A person of ordinary skill in the art will readily be aware of specific species and/or strains of microorganisms from within the genera described herein which are used in the food and/or agricultural industries and which are generally considered suitable for animal consumption.

D. Feed Additive Compositions

In one embodiment, provided herein are feed additive compositions comprising one or more the oxygen tolerant

*M. elsdenii* DFMs (and optionally one or more yeast strains and/or yeast extract) and, optionally, one or more exogenous feed enzymes. In one embodiment, the feed additive composition can be formulated in any suitable way to ensure that the formulation comprises viable DFMs and, optionally, active enzymes.

In one embodiment, the feed additive composition may be used in the form of solid or liquid preparations or alternatives thereof. Examples of solid preparations include powders, pastes, boluses, capsules, ovules, pills, pellets, tablets, dusts, and granules which may be wettable, spray-dried or freeze-dried. Examples of liquid preparations include, but are not limited to, aqueous, organic or aqueous-organic solutions, suspensions and emulsions.

In another embodiment, the feed additive composition can be used in a solid form. In one embodiment, the solid form is a pelleted form. In solid form, the feed additive composition may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

In other embodiments, any of the feed additive compositions containing oxygen-tolerant *M. elsdenii* (and optionally one or more yeast strains and/or yeast extract) disclosed herein can additionally comprise one or more excipients that improve or increase on-feed stability (such as on-feed cattle stability) of the *M. elsdenii* in the feed composition. As used herein, the phrase "on-feed stability" means the residual activity of a microorganism (for example, *M. elsdenii*) that resides in an animal feed once it is thoroughly combined and/or mixed with the feed ingredients over time prior to (for example, from about 1 hour to about 24 hours prior to) consumption by the animal (for example, cattle). Mixing can, in some embodiments, occur in a large horizontal mixer at the farm or feed lot where minor ingredients can be combined with the feed (such as corn feed), silage and other large components of the feed (such as cattle feed). In some embodiments, on-feed stability (such as on-feed cattle stability) is assessed following exposure to the outside environment on a farm or feed lot (such as in temperatures from about −30° C. to about 45° C. and from low (such as from 0% to 100% humidity). Residual activity can be measured by any means known in the art, such as enumeration and/or other activity measurements, such as lactate utilization.

The excipients can include, without limitation, polysaccharides, proteins, anti-oxidants, and/or other inorganic solids and oils. In some embodiments, the one or more excipients can be added to the oxygen-tolerant *M. elsdenii*-containing feed additive composition prior to freeze drying or lyophilization. In other embodiments, the one or more excipients can be added together or separately to the oxygen-tolerant *M. elsdenii*-containing feed additive composition prior to use (such as less than any of about 24 hr, 23 hr, 22 hr, 21 hr, 20 hr, 19 hr, 18 hr, 17 hr, 16 hr, 15 hr, 14 hr, 13 hr, 12 hr, 11 hr, 10 hr, 9 hr, 8 hr, 7 hr, 6 hr, 5 hr, 4 hr, 3 hr, 2 hr, 1 hr, 30 min, or immediately prior to use). In other embodiments, the oxygen-tolerant *M. elsdenii*-containing feed additive composition is placed in solution with said one or more excipients and then added, mixed, or combined to/with a feed.

Exemplary polysaccharides suitable for use as excipients in any of the feed additive compositions disclosed herein to improve or increase on-feed stability (such as on-feed cattle stability) of *M. elsdenii* include, without limitation, inulin, xantham gum, chitosan, carrageenan, alginate, propylene glycol alginate, dextran, mutan, pullulan, starch, gelatinized starch, hemicellulose, arabinoxylan, cellulose, cellulose derivatives (such as, methyl, ethyl, carboxymethyl, and others), pectin (citrus, apple, and sugar beet pectin), cationic starch, cationic dextrans, cationic mutans, emulsan, liposan, gellan, welan, scleroglucan, levan, curdlan, succinoglycan, rhamsan gum or natural sources of complex polysaccharides (such as, without limitation, corn gluten meal, distillers dried grain solubles (DDGS), wheat bran, wheat middlings, wheat shorts, rice bran, rice hulls, oat hulls, palm kernel, and citrus pulp; starches-corn, potato, wheat, rice) Gum arabic, gum karaya, gum ghatti, gum tragacanth, agar, seed gums (galactomannans), guar gum, tara gum, locust bean gum, or cassia gum.

Exemplary proteins suitable for use as excipients in any of the feed additive compositions disclosed herein to improve or increase on-feed cattle stability of *M. elsdenii* include, without limitation, catalase, milk protein (such as milk protein from cow, goat, sheep, camel, or whales) or protein obtained from such non-limiting sources such as soya, sunflower, peanut, lupin, peas, fava beans, cotton, corn (such as zein), wheat, canola, fish meal, dried plasma protein, meat and bone meal (including meat and dairy proteins produced through fermentation), or potato.

Anti-oxidants can be separated into two classes, lipid antioxidants, and aqueous antioxidants. Examples of lipid antioxidants include, but are not limited to, carotenoids (e.g. lutein, zeaxanthin, β-cryptoxanthin, lycopene, α-carotene, and β-carotene) and tocopherols (e.g. vitamin E, tocol, α-tocopherol, γ-tocopherol, and δ-tocopherol) and retinoids (e.g. vitamin A, retinol, and retinyl palmitate) and fat-soluble polyphenols such as quercetin. Examples of aqueous antioxidants include, but are not limited to, ascorbic acid and its oxidized form, "dehydroascorbic acid", uric acid and its oxidized form, "allantoin", bilirubin, albumin and vitamin C and water-soluble polyphenols such as catechins, which have high affinity to the phospholipid membranes, isoflavones, and procyanidins. Other exemplary anti-oxidants suitable for use as excipients in any of the feed additive compositions disclosed herein to improve or increase on-feed cattle stability of *M. elsdenii* include, without limitation, citric acid, cysteine, riboflavin, glutathione, ubiquinol, lipoic acid, sodium hydrosulphide ($Na_2S$), vitamin B derivatives, thiamine, cyanocobalamin, ergocalciferol, cholecalciferol, vitamin K derivatives, phytonadione, menaquinone, quercetin, vitamin A derivatives, retinal, 3,4-didehydroretinol, α-carotene, β-carotene, δ-carotene, γ-carotene, cryptoxanthin, butylated hydroxyanisole, butylated hydroxytoluene, alpha-lipoic acid, carotenoids, allylic sulfides, selegiline, N-actylcysteine, lecithin, tartaric acid, caffeic acid, diaryl amines, thioethers, quinones, tannins, xanthenes, procyanidins, porphrins, phenolphthalein, indophenol, coumarins, flavones, flavanones, and isomers, derivatives, and combinations thereof.

Additional excipients suitable for use include, without limitation, acetate, lysine, or histidine as well as inorganic solids and/or oils.

In some embodiments, one or more of the excipients discussed herein improve or increase on-feed cattle stability of the *M. elsdenii* in the feed composition (which optionally can include one or more strains of yeast and/or yeast extract) by any of about 25%-75%, 35%-85%, 40%-90%, 45%-95%, 75%-95%, 80%-95%, 90%-95%, 85%-95%, or 90%-100%, 100%-500%, 250%-750%, 500%-1000%, 750%-1250%, 1000%-1500%, 1250%-1750%, 1500%-2000%, 2000%-3000%, 3000%-4000%, 4000%-5000%, 5000%-6000%, 6000%-7000%, 7000%-8000%, 8000%-9000%, 9000%-10,000%, 10,000%-11,000%, or 11,000%-12,000%, such as any of about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100% 200%, 300%, 400%, 500%, 600%, 700%, 800%, 900%, 1000%, 1500%, 2000%, 2500%, 3000%, 3500%, 4000%, 4500%, 5000%, 5500%, 6000%, 6500%, 7000%, 7500%, 8000%, 8500%, 9000%, 9500%, 10,000%, 10,500%, 11,000%, 11,500%, or 12,000% or more compared to an identical feed composition that lacks said one or more excipient.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

In one embodiment, the feed additive composition is formulated to a dry powder or granules as described in WO2007/044968 (referred to as TPT granules) or WO 1997/016076 or WO 1992/012645 (each of which is incorporated herein by reference).

In one embodiment, the feed additive composition may be formulated to a granule feed composition comprising: an active agent comprising one or more oxygen tolerant *M. elsdenii* DFMs disclosed herein (and optionally one or more yeast strains and/or yeast extract) and, optionally, one or more exogenous feed enzyme and at least one coating. In one embodiment, the active agent of the granule retains activity after processing. In one embodiment, the active agent of the granule retains an activity level after processing selected from the group consisting of: 50-60% activity, 60-70% activity, 70-80% activity, 80-85% activity, 85-90% activity, and 90-95% activity.

In another embodiment, the granule may contain one coating. The coating may comprise a moisture hydrating material that constitutes at least 55% w/w of the granule. In another embodiment, the granule may contain two coatings. The two coatings may be a moisture hydrating coating and a moisture barrier coating. In some embodiments, the moisture hydrating coating may be from 25% to 60% w/w of the granule and the moisture barrier coating may be from 2% to 15% w/w of the granule. The moisture hydrating coating may be selected from inorganic salts, sucrose, starch, and maltodextrin and the moisture barrier coating may be selected from polymers, gums, whey and starch.

In yet another embodiment, the granule may be produced using a feed pelleting process and the feed pretreatment process may be conducted between 70° C. and 95° C. for up to several minutes, such as between 85° C. and 95° C. In another embodiment, the granule may be produced using a steam-heated pelleting process that may be conducted between 85° C. and 95° C. for up to several minutes.

In one embodiment, the granule may have a moisture barrier coating selected from polymers and gums and the moisture hydrating material may be an inorganic salt. The moisture hydrating coating may be between 25% and 45% w/w of the granule and the moisture barrier coating may be between 2% and 20% w/w of the granule.

In one embodiment, the active agent retains activity after conditions selected from one or more of: (a) a feed pelleting process; (b) a steam-heated feed pretreatment process; (c) storage; (d) storage as an ingredient in an unpelleted mixture; and (e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

In some embodiments, the oxygen tolerant *M. elsdenii* DFMs (and optionally one or more yeast strains and/or yeast extract) may be diluted using a diluent, such as starch powder, lime stone or the like. In one embodiment, the DFM(s) and the enzymes may be in a liquid formulation suitable for consumption preferably such liquid consumption contains one or more of the following: a buffer, salt, sorbitol and/or glycerol. In another embodiment, the feed additive composition may be formulated by applying, e.g. spraying, the enzyme(s) onto a carrier substrate, such as ground wheat for example.

In one embodiment, the feed additive composition may be formulated as a premix. By way of example only, the premix may comprise one or more feed components, such as one or more minerals and/or one or more vitamins.

In one embodiment, the DFM and exogenous feed enzymes may be formulated with at least one physiologically acceptable carrier selected from at least one of maltodextrin, limestone (calcium carbonate), cyclodextrin, wheat or a wheat component, sucrose, starch, Na2SO$_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

In another embodiment, the feed additive composition can be delivered as an aqueous suspension and/or an elixir. The feed additive composition may be combined with various sweetening or flavoring agents, coloring matter or dyes, with emulsifying and/or suspending agents and with diluents such as water, propylene glycol and glycerin, and combinations thereof.

E. Feedstuffs

In another embodiment, provided herein are feed additive compositions containing any of the oxygen tolerant *M. elsdenii* DFMs (and optionally one or more yeast strains and/or yeast extract) disclosed herein that may be used as a feed or in the preparation of a feed. The feed may be in the form of a solution or as a solid depending on the use and/or the mode of application and/or the mode of administration. When used as a feed or in the preparation of a feed, such as functional feed, the feed additive composition may be used in conjunction with one or more of the following: a nutritionally acceptable carrier, a nutritionally acceptable diluent, a nutritionally acceptable excipient, a nutritionally acceptable adjuvant, a nutritionally active ingredient.

In one embodiment, the feed additive composition disclosed herein is admixed with a feed component to form a feedstuff. In one embodiment, the feed may be a fodder, or a premix thereof, a compound feed, or a premix thereof. In one embodiment, the feed additive composition disclosed herein may be admixed with a compound feed, a compound feed component or a premix of a compound feed or to a fodder, a fodder component, or a premix of a fodder.

In one embodiment, fodder may be obtained from one or more of the plants selected from: alfalfa (lucerne), barley, birdsfoot trefoil, brassicas, Chau moellier, kale, rapeseed (canola), rutabaga (swede), turnip, clover, alsike clover, red clover, subterranean clover, white clover, grass, false oat grass, fescue, Bermuda grass, brome, heath grass, meadow grasses (from naturally mixed grassland swards, orchard grass, rye grass, Timothy-grass, corn (maize), millet, oats, sorghum, soybeans, trees (pollard tree shoots for tree-hay), wheat, and legumes.

Compound feeds can be complete feeds that provide all the daily required nutrients, concentrates that provide a part of the ration (protein, energy) or supplements that only provide additional micronutrients, such as minerals and vitamins. The main ingredients used in compound feed are the feed grains, which include corn, soybeans, sorghum, oats, and barley.

A "premix," as referred to herein, may be a composition composed of micro-ingredients such as vitamins, minerals, chemical preservatives, antibiotics, fermentation products, and other essential ingredients. Premixes are usually compositions suitable for blending into commercial rations.

In one embodiment, a feedstuff as disclosed herein may comprise one or more feed materials selected from the group comprising cereals, such as small grains (e.g., wheat, barley, rye, oats and combinations thereof) and/or large grains such as maize or sorghum; by products from cereals, such as corn gluten meal, Distillers Dried Grain Solubles (DDGS), wheat bran, wheat middlings, wheat shorts, rice bran, rice hulls, oat hulls, palm kernel, and citrus pulp; protein obtained from sources such as soya, sunflower, peanut, lupin, peas, fava beans, cotton, canola, fish meal, dried plasma protein, meat and bone meal, potato protein, whey, copra, sesame; oils and fats obtained from vegetable and animal sources; and minerals and vitamins.

In yet another embodiment, a feedstuff may comprise at least one high fiber feed material and/or at least one by-product of the at least one high fiber feed material to provide a high fiber feedstuff. Examples of high fiber feed materials include: wheat, barley, rye, oats, by products from cereals, such as corn gluten meal, Distillers Dried Grain Solubles (DDGS), wheat bran, wheat middlings, wheat shorts, rice bran, rice hulls, oat hulls, palm kernel, and citrus pulp. Some protein sources may also be regarded as high fiber:protein obtained from sources such as sunflower, lupin, fava beans and cotton In still another embodiment, the feed may be one or more of the following: a compound feed and premix, including pellets, nuts or (cattle) cake; a crop or crop residue: corn, soybeans, sorghum, oats, barley, corn stover, copra, straw, chaff, sugar beet waste; fish meal; freshly cut grass and other forage plants; meat and bone meal; molasses; oil cake and press cake; oligosaccharides; conserved forage plants: hay and silage; seaweed; seeds and grains, either whole or prepared by crushing, milling etc.; sprouted grains and legumes; yeast extract.

In one embodiment, the feed additive composition of disclosed herein is admixed with the product (e.g. feedstuff). Alternatively, the feed additive composition may be included in the emulsion or raw ingredients of a feedstuff. In another embodiment, the feed additive composition is made available on or to the surface of a product to be affected/treated. In still another embodiment, the feed additive compositions disclosed herein may be applied, interspersed, coated and/or impregnated to a product (e.g. feedstuff or raw ingredients of a feedstuff) with a controlled amount of oxygen tolerant *M. elsdenii* DFMs (and optionally one or more yeast strains and/or yeast extract and, further optionally, exogenous enzymes.

In yet another embodiment, the oxygen tolerant *M. elsdenii* DFMs (and optionally one or more yeast strains and/or yeast extract) and optional enzymes may be used simultaneously (e.g. when they are in admixture together or even when they are delivered by different routes) or sequentially (e.g. they may be delivered by different routes).

In one embodiment, the oxygen tolerant *M. elsdenii* DFMs (and optionally one or more yeast strains and/or yeast extract) and optional enzymes are applied to the feedstuff simultaneously. In yet another embodiment, the oxygen tolerant *M. elsdenii* DFMs (and optionally one or more yeast strains and/or yeast extract) and optional enzymes are admixed prior to being delivered to a feedstuff or to a raw ingredient of a feedstuff.

In one embodiment, the oxygen tolerant *M. elsdenii* DFMs (and optionally one or more yeast strains and/or yeast extract) in the feed additive compositions disclosed herein can be added in suitable concentrations including but not limited to concentrations in the final feed product that offer a daily dose of from about $2 \times 10^3$ CFU to about $2 \times 10^{11}$ CFU, from about $2 \times 10^6$ to about $1 \times 10^{10}$, and from about $3.75 \times 10^7$ CFU to about $1 \times 10^{10}$ CFU.

III. Methods

A. Methods for Improving Performance Metrics in an Animal

Further provided herein are methods for increasing performance metrics of an animal. In another embodiment, the disclosure relates to methods of increasing performance metrics of a ruminant. In still another embodiment, the disclosure relates to methods of increasing performance metrics of ruminants, including, but not limited to, dairy and beef cattle.

Provided herein are methods comprising administering to an animal a composition comprising one or more oxygen tolerant *M. elsdenii* DFMs (and optionally one or more yeast strains and/or yeast extract). In still another embodiment, the disclosure relates to a method comprising administering to an animal an effective amount of a composition comprising one or more oxygen tolerant *M. elsdenii* DFMs (and optionally one or more yeast strains and/or yeast extract) to increase performance of the animal. This effective amount can be administered to the animal in one or more doses. In one embodiment, the animal is a ruminant. In still another embodiment, the animal is a beef or dairy cow.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to increase average daily feed intake. In some embodiments, the average daily feed intake increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more oxygen tolerant *M. elsdenii* DFMs (and optionally one or more yeast strains and/or yeast extract) disclosed herein. In some embodiments, the composition is a feed additive composition. In other embodiments, the composition is a feed or feedstuff. In another embodiment, the composition further includes one or more exogenous enzymes, such as a protease, amylase, phytase, xylanase, and/or glucoamylase.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to increase average daily weight gain. In some embodiments, the average daily weight gain increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more oxygen tolerant *M. elsdenii* DFMs (and optionally one or more yeast strains and/or yeast extract) disclosed herein. In some embodiments, the composition is a feed additive composition. In other embodiments, the composition is a feed or feedstuff. In another embodiment, the composition further includes one or more exogenous enzymes, such as a protease, amylase, phytase, xylanase, and/or glucoamylase.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to increase total weight gain. In some embodiments, total weight gain increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more oxygen tolerant *M. elsdenii* DFMs (and optionally one or more yeast strains and/or yeast extract). In some embodiments, the composition is a feed additive composition. In other embodiments, the composition is a feed or feedstuff. In another embodiment, the composition further includes one or more exogenous enzymes, such as a protease, amylase, phytase, xylanase, and/or glucoamylase.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to increase feed conversion, which can be measured by either feed: gain or gain:feed. In some embodiments, feed conversion increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more oxygen tolerant *M. elsdenii* DFMs (and optionally one or more yeast strains and/or yeast extract). In some embodiments, the composition is a feed additive composition. In other embodiments, the composition is a feed or feedstuff. In another embodiment, the composition further includes one or more exogenous enzymes, such as a protease, amylase, phytase, xylanase, and/or glucoamylase.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs (such as any of the oxygen tolerant *M.

*elsdenii* DFMs disclosed herein) and optionally one or more yeast strains and/or yeast extract to increase feed efficiency. In some embodiments, feed efficiency increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more oxygen tolerant *M. elsdenii* DFMs (and optionally one or more yeast strains and/or yeast extract). In some embodiments, the composition is a feed additive composition. In other embodiments, the composition is a feed or feedstuff. In another embodiment, the composition further includes one or more exogenous enzymes, such as a protease, amylase, phytase, xylanase, and/or glucoamylase.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to decrease mortality. In some embodiments, mortality decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to animals who are not administered one or more oxygen tolerant *M. elsdenii* DFMs (and optionally one or more yeast strains and/or yeast extract). In some embodiments, the composition is a feed additive composition. In other embodiments, the composition is a feed or feedstuff. In another embodiment, the composition further includes one or more exogenous enzymes, such as a protease, amylase, phytase, xylanase, and/or glucoamylase.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to decrease feed conversion ratio (FCR). In some embodiments, FCR decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to animals who are not administered one or more oxygen tolerant *M. elsdenii* DFMs (and optionally one or more yeast strains and/or yeast extract). In some embodiments, the composition is a feed additive composition. In other embodiments, the composition is a feed or feedstuff. In another embodiment, the composition further includes one or more exogenous enzymes, such as a protease, amylase, phytase, xylanase, and/or glucoamylase.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to decrease or prevent pathogen infection (such as, without limitation, infection by a *Salmonela* sp., and/or *Escherichia coli* and/or *Streptococcus bovis*). In some embodiments, pathogen infection decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to animals who are not administered one or more oxygen tolerant *M. elsdenii* DFMs (and optionally one or more yeast strains and/or yeast extract). In some embodiments, the composition is a feed additive composition. In other embodiments, the composition is a feed or feedstuff. In another embodiment, the composition further includes one or more exogenous enzymes, such as a protease, amylase, phytase, xylanase, and/or glucoamylase.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to decrease or prevent rumen acidosis or subacute acidosis. In some embodiments, rumen acidosis or subacute acidosis decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to the prevalence of rumen acidosis or subacute acidosis in animals who are not administered one or more oxygen tolerant *M. elsdenii* DFMs (and optionally one or more yeast strains and/or yeast extract). In some embodiments, the composition is a feed additive composition. In other embodiments, the composition is a feed or feedstuff. In another embodiment, the composition further includes one or more exogenous enzymes, such as a protease, amylase, phytase, xylanase, and/or glucoamylase.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to decrease or prevent laminitis. In some embodiments, laminitis decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to the prevalence of laminitis in animals who are not administered one or more oxygen tolerant *M. elsdenii* DFMs (and optionally one or more yeast strains and/or yeast extract). In some embodiments, the composition is a feed additive composition. In other embodiments, the composition is a feed or feedstuff. In another embodiment, the composition further includes one or more exogenous enzymes, such as a protease, amylase, phytase, xylanase, and/or glucoamylase.

In still a further embodiment, the disclosure relates to a method comprising administering to an animal (such as a member of the genus *Equus*, for example, a horse, mule, donkey, or zebra) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to decrease or prevent the incidence of stomach ulcers. In some embodiments, stomach ulcers decrease by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to the prevalence of stomach ulcers in animals who are not administered one or more oxygen tolerant *M. elsdenii* DFMs (and optionally one or more yeast strains and/or yeast extract). In some embodiments, the composition is a feed additive composition. In other embodiments, the composition is a feed or feedstuff. In particular embodiments, the feed or feedstuff includes one or more high energy grains (such as, but not limited to, oats and corn). In another embodiment, the composition further includes one or more exogenous enzymes, such as a protease, amylase, phytase, xylanase, and/or glucoamylase.

The oxygen tolerant *M. elsdenii* DFM compositions disclosed herein (optionally including one or more yeast strains and/or yeast extract) provided herein can be administered, for example, as a strain-containing culture solution, a strain-containing supernatant, or a bacterial product of a culture solution. Administration of a composition comprising an oxygen tolerant *M. elsdenii* DFM provided herein and optional exogenous feed enzymes provided herein to an animal can increase the performance of the animal. In one embodiment, administration of an oxygen tolerant *M. elsdenii* and optional yeast strain(s) and/or yeast extract provided herein to an animal can increase the average daily feed intake (ADFI), average daily gain (ADG), or feed efficiency (gain:feed; G: F) (collectively, "performance metrics"). One or more than one of these performance metrics may be improved.

The composition comprising an oxygen tolerant *M. elsdenii* and optional yeast strain(s) and/or yeast extract and further optional exogenous feed enzymes may be administered to the animal in one of many ways. For example, the composition can be administered in a solid form as a veterinary pharmaceutical, may be distributed in an excipient, preferably water, and directly fed to the animal, may be physically mixed with feed material in a dry form, or the composition may be formed into a solution and thereafter sprayed onto feed material. The method of administration of the compositions disclosed herein to the animal is considered to be within the skill of the artisan. When used in combination with a feed material, the feed material can include corn, soybean meal, byproducts like distillers dried grains with solubles (DDGS), and vitamin/mineral supplement. Other feed materials can also be used.

Thus, in at least some embodiments, the effective amount of the composition comprising an oxygen tolerant *M. elsdenii* and optional yeast strain(s) and/or yeast extract and further optional exogenous feed enzymes is administered to an animal by supplementing a feed intended for the animal. As used herein, "supplementing," refers to the action of incorporating the effective amount of bacteria provided herein directly into the feed intended for the animal. Thus, the animal, when feeding, ingests the bacteria provided herein.

B. Methods for Raising Animals

Additionally provided herein are methods for raising (i.e. farming or growing) an animal. In still another embodiment, the disclosure relates to methods for raising ruminants, including, but not limited to, dairy and beef cattle.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to decrease or reduce the transition period. As used herein, "transition period" refers to the period of time to transit the foraged/grass/silage based diet (e.g., <60% concentrate) of an animal to high concentrate (e.g., >60% concentrate) feedlot diet. In some embodiments, the transition period decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to the transition period in animals who are not administered one or more oxygen tolerant *M. elsdenii* DFMs (and optionally one or more yeast strains and/or yeast extract). In some embodiments, the composition is a feed additive composition. In other embodiments, the composition is a feed or feedstuff.

In another embodiment, the disclosure relates to a method comprising administering to an animal (such as a ruminant, for example, a beef or dairy cow) an effective amount of a composition comprising one or more oxygen tolerant *M. elsdenii* DFMs (such as any of the oxygen tolerant *M. elsdenii* DFMs disclosed herein) and optionally one or more yeast strains and/or yeast extract to decrease or reduce the amount of medication provided to the animal during production. In some embodiments, the amount of medication decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to the amount of medication given to animals who are not administered one or more oxygen tolerant *M. elsdenii* DFMs (and optionally one or more yeast strains and/or yeast extract). In some embodiments, the composition is a feed additive composition. In other embodiments, the composition is a feed or feedstuff. The medication can be any commonly administered medication and includes, without limitation, antibiotics (such as tylosin) or ionaphores (such as monensin).

Additionally provided herein are methods for reducing the time required for transitioning a ruminant animal from a forage/grass/silage diet to a high concentrate diet without increasing the incidence of acidosis. As discussed supra, when ruminants are transitioned from high forage to high concentrate diet (such as corn-containing), the numbers of *M. elsdenii* present in the ruminal component of the digestive system are often insufficient to prevent a condition called lactic acidosis. The method includes administering to the ruminant currently consuming a forage/grass/silage diet an effective amount of any of the oxygen-tolerant *M. elsdenii* and optionally yeast-containing compositions (e.g. feed additive compositions, feeds, feedstuffs, and/or premix compositions).

In some embodiments, the ruminant animal is able to transition from a forage/grass/silage diet to a high concentrate diet faster (such as greater than about 60%, for example, 60%, 65%, 70%, 75%, 80%, 85%, 90%, 95%, or 100% faster, including all values falling in between these percentages) compared to ruminant animals transitioning from a forage/grass/silage diet to a high concentrate diet in the absence of administration of an oxygen-tolerant *M. elsdenii*-containing composition. Also (or in addition to), ruminant animals administered an effective amount of any of the oxygen-tolerant *M. elsdenii*-containing compositions (e.g. feed additive compositions, feeds, feedstuffs, and/or premix compositions) disclosed herein when transitioning from a forage/grass/silage diet to a high concentrate diet exhibit decreased incidence of lactic acidosis (such as greater than about 60%, for example, 60%, 65%, 70%, 75%, 80%, 85%, 90%, 95%, or 100% decreased incidence of lactic acidosis, including all values falling in between these percentages) compared to ruminant animals transitioning from a forage/grass/silage diet to a high concentrate diet in the absence of administration of an oxygen-tolerant *M. elsdenii*-containing composition.

C. Methods for Preparing a Feed Additive Composition

Also provided herein are methods for preparing a feed additive composition comprising combining one or more (such as any of 1, 2, 3, 4, 5, 6, 7, 8, 9, 10, 11, 12, 13, 14, or 15) of the oxygen tolerant *M. elsdenii* DFMs disclosed herein and one or more (such as any of 1, 2, 3, 4, 5, 6, 7, 8, 9, or 10) yeast strains and/or yeast extract. In some embodiments, the method further includes combining one or more essential oils (such as, but not limited to, cinnamaldehyde and/or thymol) and/or one or more exogenous enzymes (such as, but not limited to, one or more of a phytase, a protease, an amylase, a xylanase, a glucoamylase, and a beta-glucanase). At least about $1\times10^3$ CFU/g to at least about $1\times10^9$ CFU/g *M. elsdenii* (such as any of about $1\times10^3$ CFU/g, $1\times10^4$ CFU/g, $1\times10^5$ CFU/g, $1\times10^6$ CFU/g, $1\times10^7$ CFU/g, $1\times10^8$ CFU/g or $1\times10^9$ CFU/g, inclusive of all concentrations falling in between these values) is combined with at least one yeast strain and/or yeast extract to form the feed additive composition. Further, at least about $10^7$ CFU/g to about $10^{10}$ CFU/g, such as any of about $10^7$ CFU/g, $10^8$ CFU/g, $10^9$ CFU/g, or $10^{10}$ CFU/g, yeast can be combined with an oxygen tolerant *M. elsdenii* DFM(s) to form a feed additive composition. In further embodiments, the method can include the optional step of packaging the feed additive composition.

Further provided herein are methods for preparing a premix comprising combining one or more (such as any of 1, 2, 3, 4, 5, 6, 7, 8, 9, 10, 11, 12, 13, 14, or 15) of the oxygen tolerant *M. elsdenii* DFMs disclosed herein, at least one mineral and/or at least one vitamin, and optionally one or more (such as any of 1, 2, 3, 4, 5, 6, 7, 8, 9, or 10) yeast strains and/or yeast extract. At least about $1\times10^3$ CFU/g to at least about $1\times10^9$ CFU/g *M. elsdenii* (such as any of about $1\times10^3$ CFU/g, $1\times10^4$ CFU/g, $1\times10^5$ CFU/g, $1\times10^6$ CFU/g, $1\times10^7$ CFU/g, $1\times10^8$ CFU/g or $1\times10^9$ CFU/g, inclusive of all concentrations falling in between these values) is combined with at least one yeast strain and/or yeast extract to form the premix. Further, at least about $10^7$ CFU/g to about $10^{10}$ CFU/g, such as any of about $10^7$ CFU/g, $10^8$ CFU/g, $10^9$ CFU/g, or $10^{10}$ CFU/g, yeast can be combined with an oxygen tolerant *M. elsdenii* DFM(s) to form a premix. In further embodiments, the method can include the optional step of packaging the premix.

D. Methods for Increasing the Oxygen Tolerance of an *M. elsdenii* Strain

Also provided herein are methods for increasing the oxygen tolerance of a strain of otherwise oxygen-intolerant (i.e. anaerobic) *Megasphaera elsdenii*. The method includes the steps of introducing at least one mutation in a gene encoding the transcriptional regulator PerR (such as the gene encoded by the nucleotide sequence of SEQ ID NO:4) or immediately upstream of the gene encoding the transcriptional regulator PerR.

The PerR gene in any of the disclosed oxygen-tolerant *M. elsdenii* strains can have one or more mutations (such as any of 1, 2, 3, 4, 5, 6, 7, 8, 9, 10, 11, 12, 13, 14, 15, 16, 17, 18, 19, or 20 or more) that either prevent expression of the PerR polypeptide (such as the polypeptide of SEQ ID NO:6) or which renders the PerR polypeptide non-functional or with decreased functionality (such as about 10%, 20%, 30%, 40%, 50%, 60%, 70%, 80%, or 90% decreased functionality, including all percentages between these values) relative to the functionality of a non-mutated (i.e. wildtype) PerR polypeptide. The mutation can be located within the gene itself (e.g., within an intron or an exon) or upstream of the gene in a transcriptional regulatory region (such as from about −1 to about −200 nucleotides upstream from the gene's start codon). Corresponding to the nucleic acid sequence in SEQ ID NO:4, the PerR gene in any of the disclosed oxygen-tolerant *M. elsdenii* strains can have mutations at one or more of position 386 (such as G386T), 155 (such as C155T), 253 (such as C253T), −99 (where "-"

denotes nucleotides upstream from the start codon of the PerR gene; such as T-99C), and/or −125 (such as G-125A). In further embodiments, the mutation can be an insertion of a nucleotide into the gene and/or transcriptional regulatory sequences that results in a frameshift mutation (such as a nonsense or a missense mutation). In some embodiments, the nucleotide insertion can be at a nucleotide position such as 30 (such as an A inserted at position 30), 277 (such as an A inserted at position 277), and/or 64 (such as a G inserted at position 64) where the nucleotide positions correspond to SEQ ID NO:4. The mutation can be introduced into the *M. elsdenii* genome by random or site-directed mutagenesis.

In additional embodiments, the method for increasing the oxygen tolerance of a strain of *Megasphaera elsdenii* can further include combining the strain of *M. elsdenii* with at least one (such as any of 1, 2, 3, 4, 5, 6, 7, 8, 9, or 10) yeast strain(s) and/or yeast extract. As shown in the examples, culturing and/or combining the oxygen-tolerant *M. elsdenii* strains disclosed herein with one or more yeast strains and/or yeast extract results in increased resistance to oxygen toxicity and improvements in *M. elsdenii* viability and growth.

*M. elsdenii* strains that have increased oxygen tolerance as a consequence of generation by the methods disclosed herein can remain viable after at least about 2-45 days, about 7-12 days, or at least 30 days (such as any of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more days) of exposure to oxygen (such as, but not limited to, atmospheric levels of oxygen).

E. Methods for Increasing the Shelf-Life of *M. elsdenii*-Containing Compositions The term "shelf life" as used herein may be expressed in terms of viability, such as the time *M. elsdenii*-containing compositions can be stored wherein the *M. elsdenii* microorganisms remain viable (i.e. the period that an *M. elsdenii*-containing composition can be stored without the viability falling below a minimum acceptable level for effectiveness for use in the methods disclosed herein). Viability of *M. elsdenii* can be assessed as described in the Examples section or in any number of well-known ways disclosed in the art. The method includes formulating one or more of the oxygen-tolerant *M. elsdenii* strains (such as any of 1, 2, 3, 4, 5, 6, 7, 8, 9, 10, 11, 12, 13, 14, or 15 *M. elsdenii* strains) disclosed herein with at least one (such as any of 1, 2, 3, 4, 5, 6, 7, 8, 9, or 10) yeast strain(s) and/or yeast extract. As shown in the examples, storing one or more of the oxygen-tolerant *M. elsdenii* strains disclosed herein with one or more yeast strains and/or yeast extract results in improved shelf life of *M. elsdenii*-containing compositions (such as feed, feedstuff, or feed additive compositions).

*M. elsdenii* strains that have increased shelf life as a consequence of generation by the methods disclosed herein can maintain shelf life after at least about 2-45 days, about 7-12 days, or at least 30 days (such as any of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more days).

IV. Kits

Further provided herein are kits containing one or more of the oxygen tolerant *M. elsdenii* DFMs and, optionally, one or more yeast strains and/or yeast extract disclosed herein.

The kits can include one or more of (such as any of 1, 2, 3, 4, 5, 6, 7, 8, 9, 10, 11, 12, 13, 14, or 15) the oxygen tolerant *M. elsdenii* strains provided herein including *M.*

*elsdenii* strain ACD1265 (CBS 146328); *M. elsdenii* strain ACD1096-A01; *M. elsdenii* strain ACD1096-B01; *M. elsdenii* strain ACD1096-E01; *M. elsdenii* strain ACD1096-C02; *M. elsdenii* strain ACD1096-C05; *M. elsdenii* strain ACD1096-H05; *M. elsdenii* strain ACD1096-B03; *M. elsdenii* strain ACD1141-C10; *M. elsdenii* strain ACD1141-D10; *M. elsdenii* strain ACD1141 (CBS 146325); *M. elsdenii* strain ACD1141E (CBS 146326); *M. elsdenii* strain ACD1141F (CBS 146327); *M. elsdenii* strain ACD1265E (CBS 146329); and/or *M. elsdenii* strain ACD1265F deposited at WFDI under number CBS 146330. The kits can optionally include one or more strains of yeast (such as any of 1, 2, 3, 4, 5, 6, 7, 8, 9, or 10 strains of yeast).

The kits can further include with instructions for proper storage, maintenance, and use for administering to an animal (such as a ruminant animal) to improve one or more performance metrics. The kits can additionally include one or more of the exogenous enzymes disclosed herein (for example, one or more of a phytase, a protease, an amylase, a xylanase or a beta-glucanase) and/or one or more essential oils.

The invention can be further understood by reference to the following examples, which are provided by way of illustration and are not meant to be limiting.

EXAMPLES

Example 1: Isolation of *Megasphaera elsdenii* Strains

This example describes isolation of *Megasphaera elsdenii* strains. Fresh or frozen rumen fluid from beef cattle fed with regular or high concentrate diet was used as the source for strain isolation. The taxonomy of *Megasphaera elsdenii* strains was confirmed by 16S rDNA sequencing.

Rumen fluid from donor animals was collected and feedstuff was removed. Collected rumen fluid was used either as fresh inoculum or frozen in 15% glycerol for later inoculation. When rumen fluid was used as media supplement, it was autoclaved for 20 min and clarified by centrifuge at ~3700 g for 30 min. The clarified rumen fluid (20%) was added to the isolation medium containing 10 g/L lactate as carbon source. The medium also contained 2 g/L peptone and mineral solution (40 g/L $KH_2PO_4$. 120 g/L $(NH_4)_2SO_4$, 8 g/L $MgSO_4 \cdot 7$ $H_2O$, 2.4 g/L $CaCl_2) \cdot 2H_2O$). Bromocresol purple (100 ml of 0.04% in 1 L) was added in the medium as pH indicator. pH of the medium was adjusted to 5.5 using 90% lactic acid. Cysteine (0.25 g/L) was added as the reducing agent. Serial dilutions of rumen fluid were plated on the isolation plates. The plates were incubated anacrobically at 39° C. for 1 to 2 days. Purple colonies grown on the isolation plates were streaked twice on the same plates. The purified colonies were subject to 16S rDNA typing. Colony PCR was performed using primers 8F: 5'-AGA GTT TGA TYM TGG CTC-3' (Y=C or T; M=A or C) and 1492R: 5'-CGG TTA CCT TGT TAC GAC TT-3', and the ~1.5 kb PCR product was sequenced using the Sanger method. The sequence was used to blast the NCBI nr database. Most of the purple colonies were typed to be *Megasphaera elsdenii* with the top hits showing >99% identities to the *Megasphaera elsdenii* strains in the public databases including DSM20460 and the type strain ATCC25940.

Example 2: Characterization of *Megasphaera elsdenii* Strains

This example describes screening and characterization of isolated *Megasphaera elsdenii* strains for oxygen tolerance and lactate utilization.

Forty-six *Megasphaera elsdenii* strains were cultured in 96 well plates in duplicates. They were grown in Reinforced Clostridial Medium (RCM) from Becton Dickinson (Franklin Lakes, NJ). *Megasphaera elsdenii* ATCC25940 was used as control. The strains were cultured overnight in RCM medium at 39° C. anaerobically. The seed cultures were normalized by adjusting OD600 to 1.0 in RCM medium. These normalized cultures were inoculated at 1:10 ratio for subsequent assays with the starting OD as ~0.1. For oxygen tolerance test, the normalized cultures (1 OD600 in RCM pH 6.8) in 96-deep well plate covered with breathable film were exposed to air on bench top for up to 6 days. On each day, were cultured overnight in pre-reduced RCM medium at 39° C. overnight anaerobically. The final OD600 of each strain was adjusted to 1.0 in pre-reduced RCM media. 0.5 ml of each OD600-adjusted culture was transferred into 96-deep well plate and sealed with breathable film. The plate containing cultures was left on benchtop exposed to air for up to 6 days. At each day, two replicates of each sample were taken to measure viability by diluting 1:10 dilution (250 ul/well) in 96-well culture plate in RCM media and grow at 39 C overnight anaerobically. Growth was monitored and results (Yes or No) are summarized in the table below.

TABLE 1

Growth of *Megasphaera elsdenii* strains after air exposure

| | | Growth after oxygen exposure | | | | | | |
|---|---|---|---|---|---|---|---|---|
| Strain | Isolation | Day 0 | Day 1 | Day 2 | Day 3 | Day 4 | Day 5 | Day 6 |
| ACD1009 | natural isolate | Y | Y | N | N | N | N | N |
| ACD1265 | variant of ACD1009 | Y | Y | Y | Y | Y | Y | Y |
| ACD1096 | natural isolate | Y | N | N | N | N | N | N |
| ACD1141 | natural isolate | Y | Y | Y | N | N | N | N |
| ATCC25940 | ATCC type strain | Y | Y | N | N | N | N | N | aliquots of 20 ul were taken to culture in RCM (pH 6.8) at 1:10 ratio in 96-well plate at 39 C overnight anaerobically. Recovery of the surviving cells were indicated by overnight growth of the cultures. For lactate utilization assay, the normalized cultures were inoculated into the rumen fluid based lactate-containing isolation medium, and incubated anaerobically for ~6 hour or overnight. Culture supernatants were obtained by centrifuge at ~3700 g for 10 min and filtration via 0.2 μm filter. Lactate concentrations were measured by HPLC.

The lactic acid was determined by using a Waters 2695 HPLC system with Bio-Rad Aminex HPX-87 column and column temperature at 40 C. The mobile phase was 0.01N sulfuric acid in water and the HPLC system was run at isocratic condition with flowrate of 0.6 ml/min. The injection volume was 10 ul and run time was 45 minutes. Lactic acid was detected by a Waters 2124 refractive index detector at 40 C and a Waters 2996 photodiode array detector at 210 nm. Concentration of lactic acid were quantitated by external calibration standards.

Example 3: Comparison of Oxygen Tolerant
*Megasphaera elsdenii* Strain with its Parent This example describes isolation of an oxygen tolerant variant of *Megasphaera elsdenii* strain ACD1265. The properties of this oxygen tolerant *Megasphaera elsdenii* strain was compared with its parent ACD1009.

The parent strain of *Megasphaera elsdenii* ACD1009 was isolated from fresh rumen fluid collected from a Delaware farm. Oxygen tolerant *Megasphaera elsdenii* strain, ACD1265 was isolated by streaking its parent strain (ACD1009) on the isolation plates in aerobic condition. The streaked plates were incubated anaerobically at 39° C. for 2~3 days until purple colonies appeared. Purple colonies grown on the isolation plates were purified by streaking twice on the same type of isolation plates. The purified colonies were characterized for oxygen tolerance as well as growth and lactate utilization.

Oxygen tolerance of ACD1265 was compared with its parent ACD1009 and several other strains. These strains The ACD1265 variant was able to tolerate exposure in the air for 6 days, whereas its parent ACD1009 was only able to grow after air exposure for 1 day. The oxygen tolerance of the ACD1265 was significantly improved. The ATCC25940 type strain showed similar tolerance as ACD1009. Other natural isolates have varied degree of oxygen tolerance. ACD1141 showed more oxygen tolerance than ATCC by growing up after two days of oxygen exposure, whereas ACD1096 was more sensitive and only tolerant for several hours of oxygen exposure. ACD1141 was a more oxygen tolerant natural isolate.

The oxygen tolerant variant ACD1265 and its parent ACD1009 were compared for growth and lactate utilization. After cultured overnight in RCM medium at 39° C. anaerobically, the final OD600 for ACD1009 was about 6~7 and ACD1265 was about 4.5~5. The cell density of overnight culture ACD1265 was about 20~25% lower than that of ACD1009. The cultures were normalized by adjusting OD600 to 1.0 in RCM medium. These normalized cultures were inoculated at 1:10 ratio (starting OD 0.1) for lactate utilization assay as described in Example 2. The percentage of lactate remaining in the cultures (residual lactate concentration divide by the starting lactate concentration in the medium control) was analyzed by HPLC. There was 30% residue lactate for ACD1009 and 39.5% residue lactate for ACD1265 after 6 hour incubation. The slight decrease of lactate utilization in ACD1265 likely reflected its 20~25% decreased growth. The lactate in the medium was depleted for both strains after prolonged incubation.

Example 4: Quantitative Determination of Viability
After Oxygen Exposure

This example describes quantitative assessment of viability of the oxygen tolerant strain ACD1265 with its parent ACD1009 and the type strain ATCC25940 after oxygen exposure.

The Most Probable Number (MPN) method was used for quantitative assessment of oxygen tolerance of ACD1009, ACD1265 and ATCC25940. This MPN study used microtiter plates for serial dilutions, each sample with 4 replicates of 10× serial dilutions up to 12 wells. For more information on the MPN method see the following references: Cochran, W. G., (1950), Estimation of Bacterial Densities by Means of the "Most Probably Number", *Biometrics*, p. 105-116. Rowe, R., Todd, R., and Waide, J., (1977), Microtechnique for Most-Probable-Number Analysis, Applied and Enviromental Microbiology, Vol. 33, No. 3, p. 675-680. Woodward. R. L., (1957), How Probable Is the Most Probable Number?, *Journal of the American Water Works Association*, 49, p. 1060-1068.

ACD1265, ACD1009 and ATCC25940 were cultured overnight in RCM medium at 39° C. anaerobically. The final OD600 for ACD1009 was about 5.5 and ACD1265 was about 4.5, ATCC25940 was about 6.7. For oxygen exposure, 1.4 ml of each of the overnight cultures were transferred into a 96-deep well plate sealed with breathable film and were exposed to air on bench top for up to 12 days. At intervals, aliquots of samples were taken to measure viability in pre-reduced RCM medium (pH 6.8) by MPN and the microtiter plates were incubated at 39° C. anaerobically for 1-2 days. The growth of bacteria was recorded by visual examination and MPN was calculated. Data in the FIG. 1 showed that all three strains were tolerant after exposure to air for 2 days. After prolonged air exposure, the ACD1009 parent strain and the ATCC type strain totally lost viability (1.28E+01 is the detection limit of the method). However, the variant ACD1265 retained $1.16 \times 10^8$ cfu/ml after 7 to 9 days of exposure, and still retained $5.73 \times 10^4$ cfu/ml after 12 days of exposure. This showed that variant ACD1265 was more oxygen tolerant than its parent ACD1009 or the ATCC25940 type strain.

Example 5: Genomic Sequencing of *Megasphaera elsdenii* Strains

This example describes genomic sequencing of the isolated *Megasphaera elsdenii* strains and the oxygen tolerant variant ACD1265. Whole genome sequence analysis showed that ACD1265 contains a SNP at the PerR gene that most likely contributed to its improved oxygen tolerance.

Overnight cultures of *Megasphaera elsdenii* strain were centrifuged at room temperature 4500×g for 10 minutes. The resulting supernatant was discarded and cell pellets were processed according to QIAGEN's MO BIO's PowerMag Microbial DNA Kit (Catalog number: 27200-4). Briefly, the cell pellets were resuspended in 350 µL of PowerMag MicroBead Lysis solution plus RNase A solution. Resuspensions were transferred to a PowerMag Bead Plate. Plates were shaken on bead beater at 20 Hz for 10 minutes, rotating plates every 5 minutes. Plates were centrifuged at room temperature 4500×g for 6 minutes. Supernatant was transferred to a clean PowerMag 1 mL Collection plate and 100 µL of PowerMag IRT Solution was added to each well then mixed with brief vortexing. Plates were then incubated at 4° C. for 10 minutes. Plates were again centrifuged at room temperature 4500×g for 9 minutes and 450 µL of supernatant was transferred to a KingFisher Deep Well plate 96 plate and combined with 500 µL of SwiftMag Beads. After processing through the KingFisher with 3-100% ethanol washes, DNA was eluted with Solution EB. Resulting gDNA was submitted for Whole Genome Sequencing library construction.

The Illumina NEXTERA Flex system (Illumina 20018705) and index plate (Illumina 20018708) were used to process genomic DNA for sequencing. Briefly, isolated DNA was assessed for quality and concentration. DNA was then processed with NEXTERA Flex kit. Libraries produced were checked for quality and concentration using Quantus dsONE, Advanced Analytics Fragment Analyzer, and Bioanalyzer TapeStation. Libraries were pooled, normalized to 2 nM and run on Illumina NextSeq. The run generated 25 GB (gigabases) of data. The Genome sequencing data of these strains were assembled using an in-house pipeline. In brief, reads were filtered and trimmed based on quality then corrected using BFC. The corrected reads were assembled using the Spades assembler. After assembly, the Opening Reading Frames (ORFs) were predicted by Prodigal and annotated by Prokka. 16S rRNA genes were predicted by Barrnap and the closest species identification by RDP pairwise alignment tool against a vetted 16S reference database containing mostly 16S genes from type strains and public genomes. The SNPs between the genome assemblies of these strains were identified by bowtie2 and samtools. The SNPs were then mapped to corresponding genes based on gene annotation.

There are only 2 SNPs identified between the oxygen tolerant strain ACD1265 (sequence ID AG8660041) and the parent ACD1009 (sequence ID AG8660040). One SNP is on a gene encoding a protein named transcriptional regulator PerR, the other SNP is on a distant non-coding region. The parent strain ACD1009 had a base G at position 386 of perR gene while ACD1265 had a base T. This mutation changes a codon UGC for cysteine (C) into another codon UUG for phenylalanine (F). All the other 46 strains being sequenced had identical nucleotide perR gene to the perR gene from ACD1009. The nucleotide and protein sequences of the two perR genes are listed below. The different bases and amino acids are highlighted in red.

PerR protein belongs to KEGG ortholoy family K09825 that is known to regulate oxidative stress response in bacteria (Shetty et al., 2013. Comparative genome analysis of *Megasphaera* sp. reveals niche specialization and its potential role in the human gut. PLOS One. 2013; 8: e79353). Amino acid cysteine at position 129 seems to be highly conserved in PerR protein. Out of 1,213 protein sequences from K09825 family of KEGG database version 82, 1,170 (96.5%) proteins have cysteine at that position, and only 5 had phenylalanine. It was also reported that deletion of PerR protein in obligate anaerobe *Clostridium acetobutylicum* resulted in prolonged aerotolerance and limited growth under aerobic conditions (Hillmann et al., 2008. PerR acts as a switch for oxygen tolerance in the strict anaerobe *Clostridium acetobutylicum*. Mol Microbiol. 2008; 68 (4): 848-860. doi: 10.1111/j.1365-2958.2008.06192.x).

Example 6: Isolation and Characterization of Other Oxygen Tolerant Variants of *Megasphaera elsdenii* Strains This example describes more oxygen tolerant variants of *Megasphaera elsdenii* isolated from other parent strains. The oxygen tolerant variants contained mutations mapped in the perR gene or upstream of the perR gene.

Figure 2:
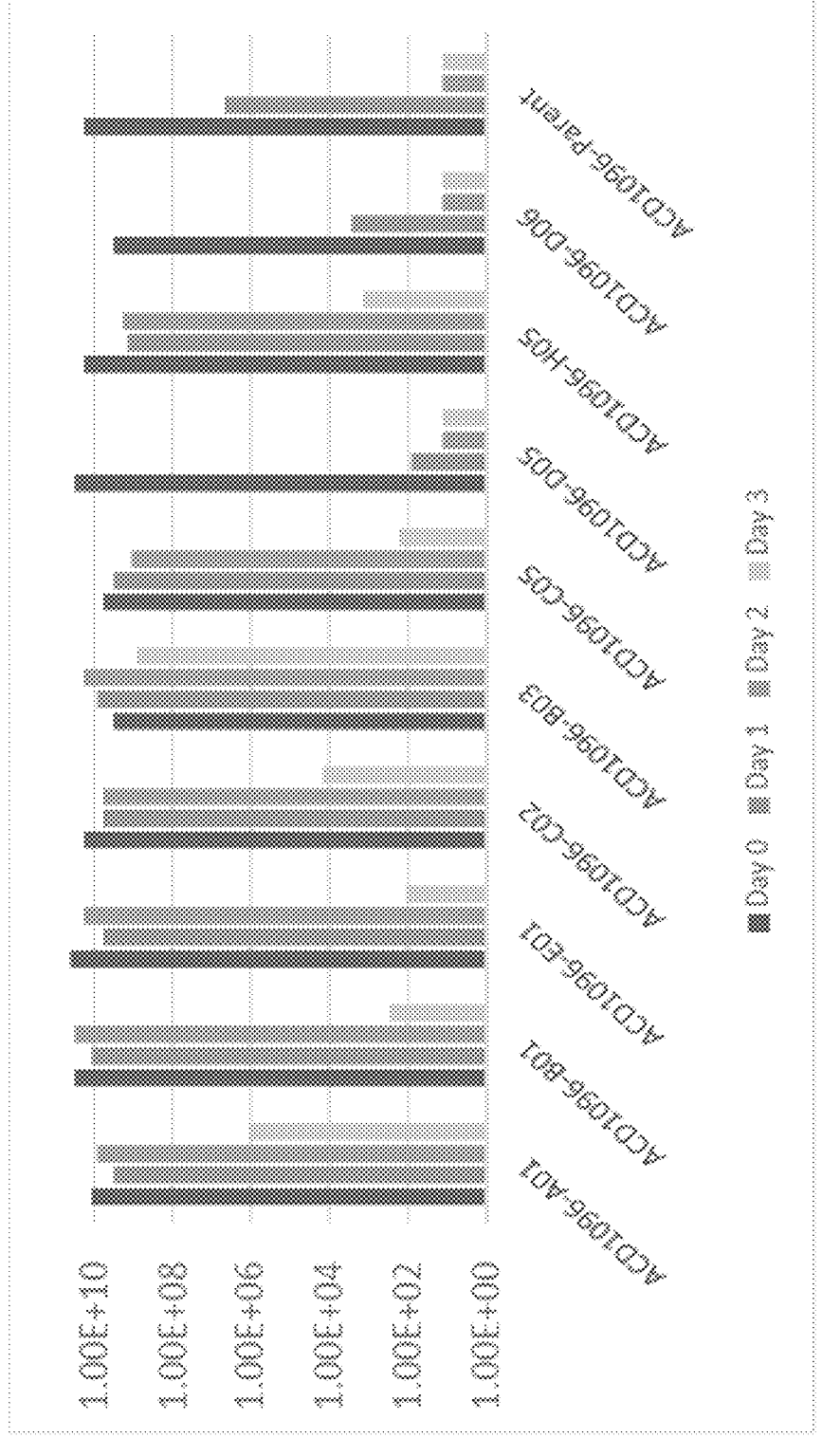
FIG. 2 depicts a bar graph showing MPN assessment of oxygen tolerance of *Megasphaera elsdenii* variant strains derived from parent ACD1096. The overnight cultures of the *Megasphaera elsdenii* strains were exposed to air for up to 3 days. Day 0 is the anaerobic control without oxygen exposure. Y axis is the cfu/ml calculated by the MPN method.
Figure 3:
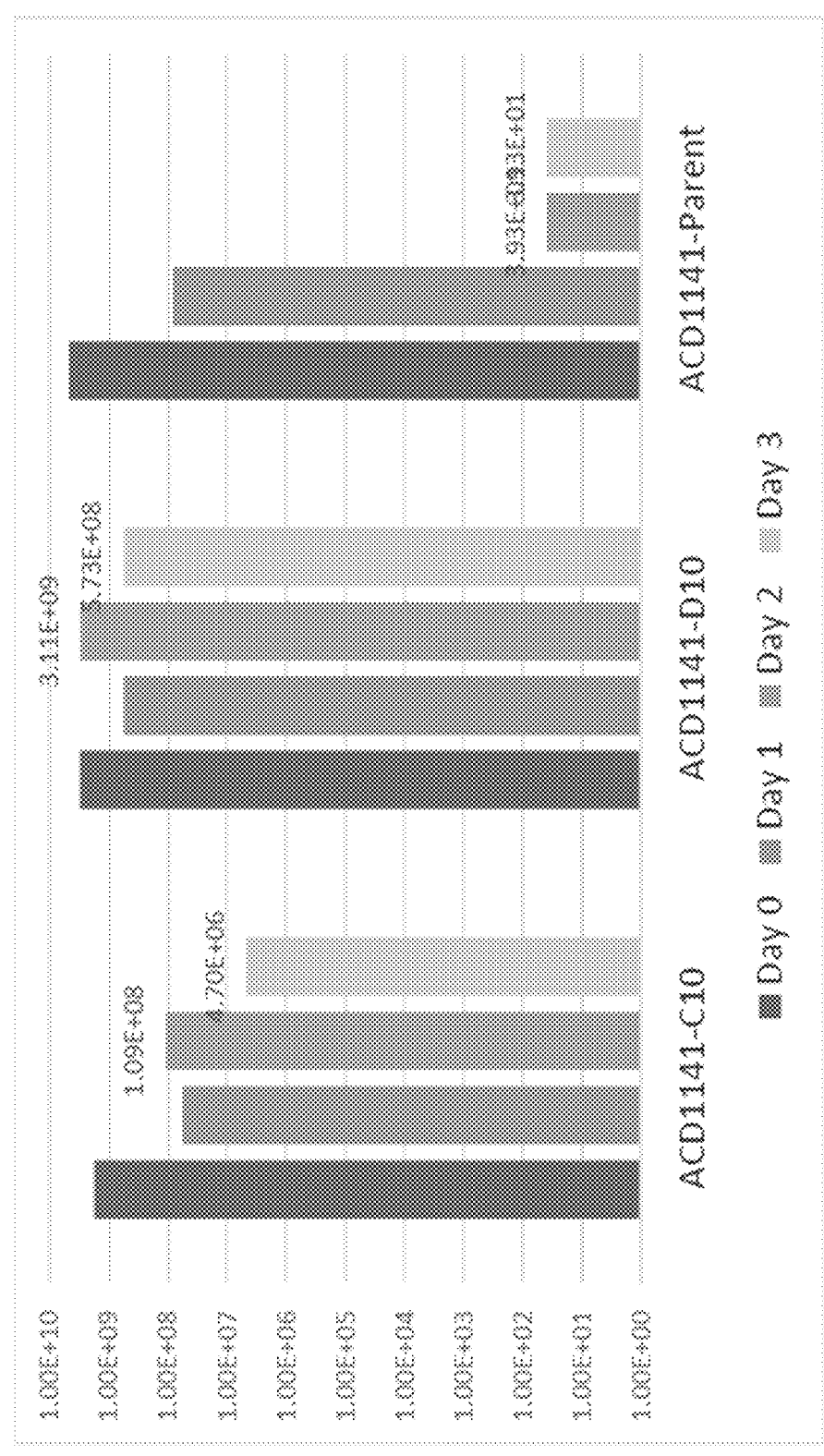
FIG. 3 depicts a bar graph showing MPN assessment of oxygen tolerance of *Megasphaera elsdenii* variant strains derived from parent ACD1141. The overnight cultures of the *Megasphaera elsdenii* strains were exposed to air for up to 3 days. Day 0 is the anaerobic control without oxygen exposure. Y axis is the cfu/ml calculated by the MPN method.

The *Megasphaera elsdenii* parent strains ACD1096 and ACD1141 were isolated from frozen rumen fluid collected from two different cattles on an Oklahoma farm. Although both strains were natural isolates, ACD1141 showed more oxygen tolerance than ACD1096. Increased oxygen tolerant variants of ACD1096 and ACD1141 were isolated similarly as described previously for ACD1265. MPN assessment of viability of ACD1096 derived *Megasphaera elsdenii* variant strains after oxygen exposure is shown in FIG. 2. MPN assessment of viability of ACD1141 derived *Megasphaera elsdenii* variant strains after oxygen exposure is shown in FIG. 3. Whole genome sequence of these variants was also determined and the PerR related mutations were summarized in Table 2.

TABLE 2

Mapping of mutations in oxygen tolerant variants of *Megasphaera elsdenii*.

| Strain ID | Mutation type | Position at nucleotide | Nucleotide change | PerR Amino acid change | Notes |
|---|---|---|---|---|---|
| 1265 (1009v1) | substitution | 386 | G386T | C129F | |
| 1096-A01 | substitution | 155 | C155T | T52M | |
| 1096-B01 | insertion | 30 | Insertion of A | N10 frameshift | |
| 1096-B03 | insertion | 277 | Insertion of A | C93 frameshift | |
| 1096-C05 | insertion | 30 | Insertion of A | N10 frameshift | |
| 1096-E01 | insertion | 30 | Insertion of A | N10 frameshift | |
| 1096-H05 | insertion | 64 | Insertion of G | Y22 frameshift | |
| 1096-C02 | substitution | −99 | T-99C | NA | upstream |
| 1141-C10 | substitution | 253 | C253T | H85Y | |
| 1141-D10 | substitution | −125 | G-125A | NA | upstream |

Among the 9 variants of the ACD1096-derived strains, 7 of them showed improved oxygen tolerance than the ACD1096 parent and had mutation in perR gene or upstream of perR gene. Two of them (D05 and D06) showed similar oxygen tolerance as the parent and did not have mutation in the perR region. The two variants of ACD1141 (C10 and D10) showed increased oxygen tolerance also had mutation in perR gene or upstream of perR.

Example 7: Comparison of Oxygen Tolerance of Evolved *Megasphaera elsdenii* Strains This example describes isolation of *Megasphaera elsdenii* variants by directed evolution and comparison of oxygen tolerance of evolved *Megasphaera elsdenii* strains.

Figure 4:
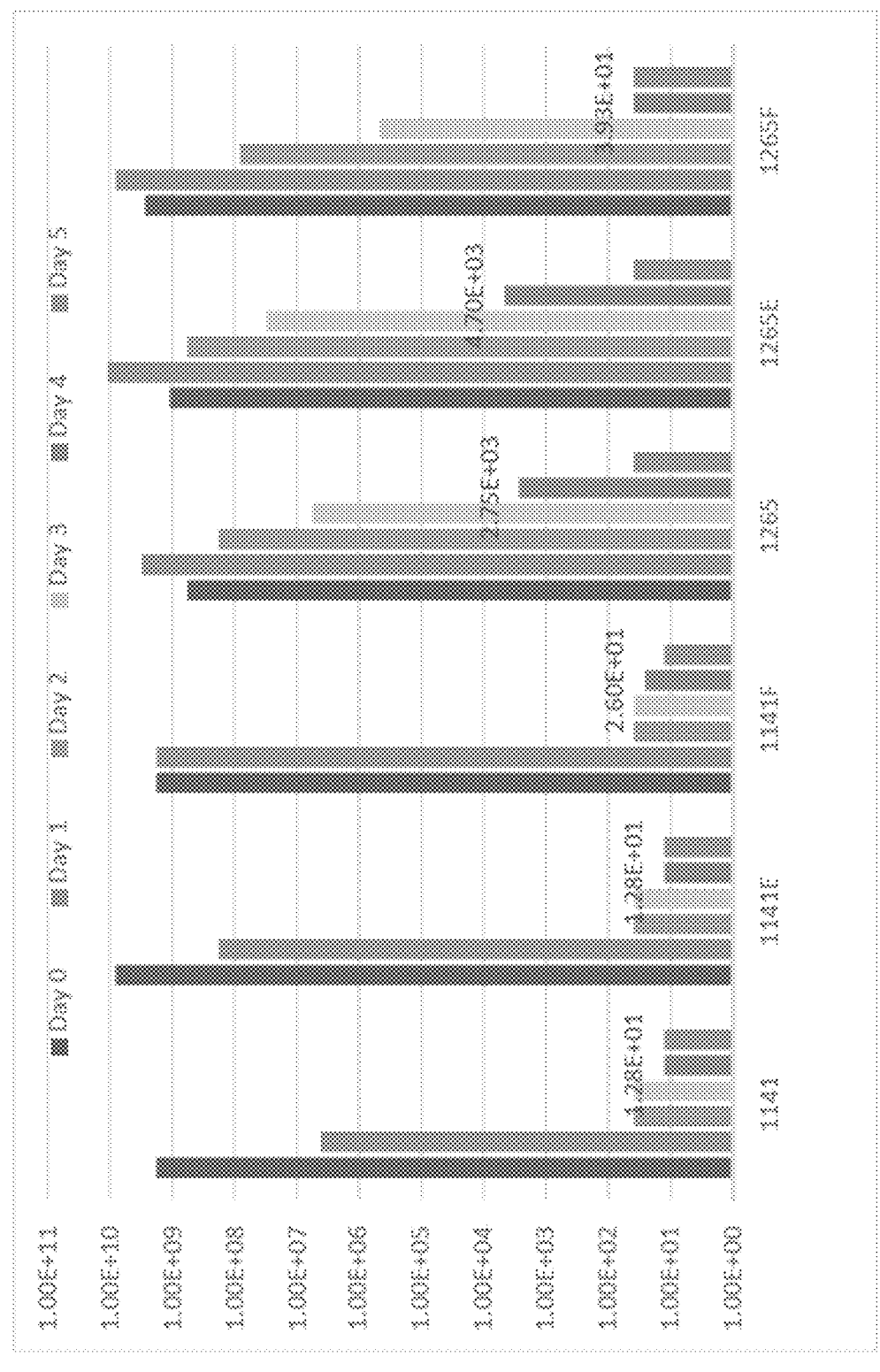
FIG. 4 depicts a bar graph showing oxygen tolerance of evolved *Megasphaera elsdenii* strains ACD1141 E/F and ACD1265E/F by MPN. Day 0 is the anaerobic control without oxygen exposure. Y axis is the cfu/ml calculated by the MPN method.

Directed evolution was conducted with 1141 and 1265 as starting strains by serial transfer in RCM medium. After 75 to 100 generations, cells were plated for isolation. 1141E and 1141F strains were isolated from 1141 evolution, while 1265E and 1265F were isolated from 1265 evolution. The oxygen tolerance of 1141E/F and 1265E/F were compared with the starting strains. All strains were cultured in pre-reduced RCM medium at 39° C. overnight anaerobically. OD600 were adjusted to 1.0 with pre-reduced RCM media. 0.25 ml of each of these cultures were transferred into a 96-Deep-Well plate sealed with breathable film and left at benchtop to exposure to air for up to 5 days. At each day, four replicates of each sample were taken to measure the viability (cfu/ml) of these samples by MPN. FIG. 4 showed that the order of air tolerance of these strains as following: 1141F>1141E>1141; 1265E>1265>1265F. The evolved 1141E and 1141F had improved oxygen tolerance comparing to the 1141 starting strain as shown by the increased survival after 1 day air exposure. The 1265E had slight increased oxygen tolerance and 1265F had slight decreased oxygen tolerance comparing to the 1265 starting strain. Nevertheless, 1265E and 1265F still showed very high oxygen tolerance comparable to 1265, and much more tolerant than 1141 or the evolved 1141E/1141F strains.

Example 8: Yeast Improved Viability of *Megasphaera elsdenii* Upon Oxygen Exposure Under "Rumen" Condition This example demonstrates a *Saccharomyces cerevisiae* strain YSC35 for improving viability of *Megasphaera els-*

*denii* ACD1096 upon oxygen exposure under so-called "rumen" condition (in rumen fluid lactate containing medium, pH 5.5, 39° C., air exposure for short periods of time such as 3 hours).

The yeast strain YSC35 was obtained from an internal silage yeast collection. It was typed to be *Saccharomyces cerevisiae* based on ITS sequencing. Using a sterile pipette tip, pick a little of yeast cells and re-suspend in 25 µl of 0.02M NaOH. Boil the re-suspended samples on a PCR machine at 99° C. for 10 minutes. Add 2 µl boiled sample to 25 µl PCR reaction mixture with primers ITS1 (5'-TCCGTAGGTGAACCTGCGG-3') and ITS4 (5'-TCCTCCGCTTATTGATATGC-3'), and 1× Q5 hot start PCR enzyme mixture (Invitrogen). Clean the PCR products with ExoSAP-IT (ThermoFisher) at 37° C. for 4 min and send the cleaned PCR products for DNA sequencing. Blast the sequencing results in NCBI website and identified the top hit of YSC35 as *Saccharomyces cerevisiae*.

*Megasphaera elsdenii* ACD1096 and the *Saccharomyces cerevisiae* YSC35 were cultured individually in RCM media (BD, Franklin Lakes, NJ) at different growth conditions (anaerobic 39° C. for *Megasphaera elsdenii*: aerobic 33° C. shaking at 250 rpm for yeast). OD600 of each strain was measured in spectrophotometer Ultraspec 3000 (Pharmacia Biotech, Piscataway, NJ). *Megasphaera elsdenii* was normalized to OD=2 in rumen fluid based media with 10 g/L DL-lactate as described in previous examples. Yeast cells were centrifuged at 16,000 g for 1 min, supernatant removed and pellet resuspended in the same lactate containing media. In the co-culture consortia, *Megasphaera elsdenii* and *Saccharomyces cerevisiae* cells were combined at OD ratio of 1:5 in deep well plate (Corning 96-well assay block, COSTAR 3960). Single strain controls were included. In the oxygen exposure treatment, plates with cell culture were covered with sterile breathable membrane (Thermo Scientific Nunc sealing tape 241205), and were exposed to air. An anaerobic control *M. elsdenni* was prepared similarly without oxygen exposure and incubated anaerobically. After 3 hours of incubation at 39° C. with air exposure, ten-fold serial dilutions were made in pre-reduced phosphate buffered saline (1×PBS). 100 ul of 1:20000 fold diluted cells were plated on rumen fluid lactate containing agar plates. The agar plates were incubated anaerobically at 39° C. for about 2 days. *Megasphaera elsdenii* grew well on this isolation agar medium anaerobically, whereas *Saccharomyces cerevisiae* cannot grow on this agar medium anaerobically. The selective growth of *Megasphaera elsdenii* on these plates allowed us to determine the viable counts of *Megasphaera elsdenii* in the Me+yeast consortia. As shown in Table 3, viability of *Megasphaera elsdenii* ACD1096 strain decreased about 1 log after exposure to air for 3 hours. The *Megasphaera elsdenii* in the consortia with yeast YSC35 maintained the viability to almost the level as the anaerobic *Megasphaera elsdenii* control without air exposure.

TABLE 3

Viable counts of *Megasphaera elsdenii* 1096 on
rumen fluid based lactate containing agar plates
after plated 100 μl of 1:20000 fold diluted cells.

| Strains | Plate1 | Plate2 | Average | cfu/ml |
|---|---|---|---|---|
| Me (1096) | 104 | 115 | 110 | 2.19E+07 |
| Me + YSC35 | 868 | 565 | 717 | 1.43E+08 |
| Me anaerobic | 728 | 996 | 862 | 1.72E+08 |

Example 9: Yeast Improved Lactate Utilization of *Megasphaera elsdenii* Upon Oxygen Exposure Under "Rumen" Condition This example demonstrates a *Saccharomyces cerevisiae* strain YSC35 for improving lactate utilization of *Megasphaera elsdenii* ACD1096 upon oxygen exposure under so called "rumen" condition (in rumen fluid lactate containing medium, pH 5.5, 39° C., air exposure for short periods of time such as 3 hours).

*Megasphaera elsdenii* ACD1096 and the *Saccharomyces cerevisiae* YSC35 were grown and treated as described in Example 8. After 3 hours of incubation at 39° C. with air exposure, in addition to viability plating, supernatants were also analyzed for lactate utilization. Cells were centrifuged at 3220 g for 10 minutes. Supernatant was filtered through 0.2 um 96-well filter plate (PALL 8119) and loaded on HPLC for lactate measurement. The lactic acid was determined by using a Waters 2695 HPLC system with Bio-Rad Aminex HPX-87H column and column temperature at 40° C. The mobile phase was 0.01N sulfuric acid in water and the HPLC system was run at isocratic condition with flow-rate of 0.6 ml/min. The injection volume was 10 ul and run time was 45 minutes. Lactic acid was detected by a Waters 2124 refractive index detector at 40° C. and a Waters PDA 2996 photodiode array detector at 210 nm. Concentration of lactic acid were quantitated by external calibration standards. The residual lactate concentration in the culture supernatants was summarized in Table 4 below. The medium blank without any cells contained about 93.5 mM lactate. The medium with YSC35 yeast alone contained about 90.4 mM, suggesting that yeast cells did not use lactate under the assay condition. The anaerobically incubated *Megasphaera elsdenii* ACD1096 clone used most of lactate and had only about 27.0 mM residual lactate. The *Megasphaera elsdenii* ACD1096 exposed to air for 3 hours did not use as much of lactate as the anaerobic *Megasphaera* cells and had 75.5 mM remaining lactate. The *Megasphaera elsdenii* ACD1096 with YSC35 consortia exposure to air for 3 hours used much more lactate than the *Megasphaera* only cells without yeast and had only 37.3 mM remaining lactate. The yeast YSC35 in the consortia with *Megapshaera elsdenii* improved lactate utilization of *Megapshaera elsdenii*.

TABLE 4

Residual lactate concentration in culture
supernatants (mM) of Example 9

| Strains | Set1 | Set2 | Average |
|---|---|---|---|
| Me (1096) | 76.51 | 74.55 | 75.53 |
| Me + YSC35 | 36.45 | 38.15 | 37.30 |
| Me anaerobic | 25.88 | 28.03 | 26.96 |
| YSC35 | 90.76 | 90.06 | 90.41 |
| Blank | 93.39 | 93.63 | 93.51 |

Example 10: Yeast Improved Viability of *Megasphaera elsdenii* Upon Oxygen Exposure Under "Shelf Life" Condition This example demonstrates a *Saccharomyces cerevisiae* strain YSC35 for improving viability of *Megasphaera elsdenii* ACD1096 upon oxygen exposure under so called "shelf life" condition (RCM medium, pH 6.8, room temperature, air exposure for long periods of time such as 21 hours).

*Megasphaera elsdenii* ACD1096 and the *Saccharomyces cerevisiae* YSC35 were cultured individually in RCM media at different growth conditions (anaerobic 39° C. for *Megasphaera elsdenii*: aerobic 33° C. shaking at 250 rpm for yeast). OD600 of each strain was measured in spectrophotometer. *Megasphaera elsdenii* was normalized to OD=2 in RCM media. In the co-culture consortia, *Megasphaera elsdenii* and *Saccharomyces cerevisiae* cells were combined at OD ratio ~1:5 in deep well plate (Corning 96 well assay block, COSTAR 3960). Single strain controls were included. In the oxygen exposure treatment, plates with cell culture were covered with sterile breathable membrane (Thermo Scientific Nunc sealing tape 241205), and were exposed to air. An anaerobic control *M. elsdenii* was prepared similarly without oxygen exposure and incubated anaerobically. After 21 hours of incubation at room temperature with air exposure, ten-fold serial dilutions were made in 1×PBS. 100 μl of 1:1000 fold diluted cells were plated on the selective rumen fluid based lactate agar plates for enumeration of *Megasphaera elsdenii* cells. The agar plates were incubated anaerobically at 39° C. for about 2 days. The data in Table 5 showed that *Megasphaera* in the consortia with YSC35 yeast had at least 100 fold more viable counts than the *Megasphaera* alone cells after air exposure for 21 hours.

TABLE 5

Viable counts of *Megasphaera elsdenii* ACD1096
on rumen fluid based lactate containing agar plates
after plated 100 μl of 1:1000x diluted cells

| Strains | plate1 | plate2 | average | Cfu/ml |
|---|---|---|---|---|
| Me (1096) | 0 | 0 | 0 | <10E+4 |
| Me + YSC35 | 820 | 199 | 510 | 5.10E+06 |
| Me anaerobic | 852 | 652 | 752 | 7.52E+06 |

Example 11: Yeast Improved Lactate Utilization of *Megasphaera elsdenii* Upon Oxygen Exposure Under "Shelf Life" Condition This example demonstrates a *Saccharomyces cerevisiae* strain YSC35 for improving lactate utilization of *Megasphaera elsdenii* ACD1096 upon oxygen exposure under so called "shelf life" condition (RCM medium, pH 6.8, room temperature, air exposure for long periods of time such as 21 hours).

*Megasphaera elsdenii* ACD1096 and the *Saccharomyces cerevisiae* YSC35 were grown and treated as described in Example 10. After 21 hours of incubation at room temperature with air exposure, cells were inoculated into rumen fluid based media with 10 g/L DL-lactate at 1:3× fold dilution ratio. The cells were recovered in the lactate containing medium anaerobically at 39° C. for 6 hours, then centrifuged at 3220 g for 10 minutes. Supernatant were filtered through 0.2 μm 96-well filter plate (PALL 8119) and loaded on HPLC for lactate measurement, as described in Example 8. Data in Table 6 below showed that *Megasphaera elsdenii* ACD1096 lost the ability to utilize lactate after 21 hours of air exposure. The residual lactate from the air exposed *Megasphaera elsdenii* ACD1096 was the same as the blank medium control or the yeast only culture. The *Megasphaera elsdenii* ACD1096 in the consortia with yeast was able to utilize most of lactate during recovery and only 15.1 mM lactate remained.

TABLE 6

| Residual lactate concentration in culture supernatants (mM) of Example 11 | | | |
| --- | --- | --- | --- |
| Strains | set1 | set2 | average |
| Me (1096) | 66.69 | 67.43 | 67.06 |
| Me + YSC35 | 13.80 | 16.49 | 15.14 |
| YSC35 | 67.45 | 66.68 | 67.06 |
| Blank | 67.91 | 66.57 | 67.24 |

Example 12: Yeast Improved Viability of *Megasphaera elsdenii* Upon Oxygen Exposure Under "Shelf Life" Condition This example demonstrates a *Pichia* kudriavzevii strain YSC13 for improving viability of *Megasphaera elsdenii* ACD1096 upon oxygen exposure under so called "shelf life" condition (RCM medium, pH 6.8, room temperature, air exposure for long periods of time such as 22 hours).

The yeast strain YSC13 was obtained from an internal silage yeast collection. It was typed to be *Pichia* kudriavzevii based on ITS sequencing. Using a sterile pipette tip, pick a little of yeast cells and re-suspend in 25 μl of 0.02M NaOH. Boil the re-suspended samples on a PCR machine at 99° C. for 10 minutes. Add 2 μl boiled sample to 25 μl PCR reaction mixture with primers ITS1 (5'-TCCGTAGGT-GAACCTGCGG-3') and ITS4 (5'-TCCTCCGCTTATTGA-TATGC-3'), and 1× Q5 hot start PCR enzyme mixture (Invitrogen). Clean the PCR products with ExoSAP-IT (ThermoFisher) at 37° C. for 4 min and send the cleaned PCR products for DNA sequencing. Blast the sequencing results in NCBI website and identified the top hit of YSC13 as *Pichia* kudriavzevii.

*Megasphaera elsdenii* ACD1096 and *Pichia* kudriavzevii YSC13 cells were cultured individually in RCM media (anaerobic 39° C. for *Megasphaera elsdenii*: aerobic 33° C. shaking at 250 rpm for yeast). OD600 of each strain was measured in spectrophotometer. *Megasphaera elsdenii* was normalized to OD=2 in RCM media. In the co-culture consortia, *Megasphaera elsdenii* and *Pichia* kudriavzevii cells were combined at OD ratio ~1:5 in deep well plate (Corning 96 well assay block, COSTAR 3960). Single strain controls were included. In the oxygen exposure treatment, plates with cell culture covered with sterile breathable membrane (Thermo Scientific Nunc sealing tape 241205) and were exposed to air. An anaerobic control *M. elsdenii* was prepared similarly without oxygen exposure and incubated anaerobically. After 22 hours of incubation at room temperature with air exposure, ten-fold serial dilutions were made in 1×PBS. 100 μl of 1:100 fold diluted cells were plated on the selective rumen fluid based lactate agar plates for enumeration of *Megasphaera elsdenii* cells. The agar plates were incubated anaerobically at 39° C. for about 2 days. As shown in Table 7, after air exposure for 22 hours at room temperature, no viable cells of *Megasphaera elsdenii* ACD1096 were recovered at the 1:100 dilutions plated, whereas the anaerobic control *Megasphaera elsdenii* cells had too many colonies to count. The *Megasphaera elsdenii* cells in the yeast consortia with YSC13 had hundreds to thousands of colonies at this dilution. The *Pichia* kudriavzevii YSC13 improved viability of *Megasphaera elsdenii* ACD1096 for at least 1000-fold after air exposure for 22 hours.

TABLE 7

| Viable counts of *Megasphaera elsdenii* ACD1096 on rumen fluid based lactate containing agar plates after plated 100 μl of 1:100x diluted cells | | | | |
| --- | --- | --- | --- | --- |
| Strain | plate1 | plate2 | average | cfu/ml |
| Me (1096) | 0 | 0 | 0 | <10E+03 |
| Me + YSC13 | 2176 | 748 | 1462 | 1.46E+06 |
| Me Anaerobic | Too many | Too many | Too many | >2*10E+6 |

Example 13: Yeast Improved Lactate Utilization of *Megasphaera elsdenii* Upon Oxygen Exposure Under "Shelf Life" Condition This example demonstrates a *Pichia* kudriavzevii strain YSC13 for improving lactate utilization of *Megasphaera elsdenii* ACD1096 upon oxygen exposure under so called "shelf life" condition (RCM medium, pH 6.8, room temperature, air exposure for long periods of time such as 22 hours).

*Megasphaera elsdenii* ACD1096 and the *Pichia* kudriavzevii strain YSC13 were grown and treated as described in Example 12. After 22 hours of incubation at room temperature with air exposure, cells were inoculated into rumen fluid based media with 10 g/L DL-lactate at 1:10× fold dilution. The cells were recovered in the lactate containing medium anaerobically at 39° C. for 7 hours, then centrifuged at 3220 g for 10 minutes. Supernatant were filtered through 0.2 um 96-well filter plate (PALL 8119) and loaded on HPLC for lactate measurement. Data in Table 8 below showed that *Megasphaera elsdenii* ACD1096 lost the ability to utilize lactate after 22 hours of air exposure. The residual lactate from the air exposed *Megasphaera elsdenii* ACD1096 was the same as the blank medium control or the yeast only culture. The *Megasphaera elsdenii* ACD1096 in the consortia with yeast retained the ability to utilize lactate.

TABLE 8

| Residual lactate concentration in culture supernatants (mM) of Example 13 | | | |
| --- | --- | --- | --- |
| Strains | Set1 | Set2 | Average |
| Me (1096) | 92.91 | 92.69 | 92.80 |
| Me + YSC13 | 83.49 | 82.22 | 82.86 |

TABLE 8-continued

| Residual lactate concentration in culture supernatants (mM) of Example 13 | | | |
|---|---|---|---|
| Strains | Set1 | Set2 | Average |
| YSC13 | 93.55 | 92.88 | 93.21 |
| Me anaerobic | 71.04 | | 71.04 |
| Blank | 93.32 | 92.80 | 93.06 |

Example 14: Yeast Improved Lactate Utilization of Another *Megasphaera elsdenii* Strain Upon Oxygen Exposure Under "Rumen" Condition This example demonstrates a *Saccharomyces cerevisiae* strain YSC35 for improving lactate utilization of another *Megasphaera elsdenii* ACD1141 upon oxygen exposure under so called "rumen" condition (in rumen fluid lactate containing medium, pH 5.5, 39° C., air exposure for short periods of time such as 5.5 hours).

*Megasphaera elsdenii* ACD1141 is another *Megasphaera elsdenii* strain isolated from rumen as described in earlier examples. It exhibited more oxygen tolerance than ACD1096 strain. *Megasphaera elsdenii* ACD1141 and the *Saccharomyces cerevisiae* YSC35 were cultured and treated as described before in Example 9 except longer air exposure for 5.5 hours was carried out in this experiment. Lactate utilization data in Table 9 below showed that anaerobic *Megasphaera elsdenii* ACD1141 control used up all lactate under this assay condition. The *Megasphaera elsdenii* ACD1141 exposed to air for 5.5 hours utilized majority of lactate and had 18.4 mM lactate left. The *Megasphaera elsdenii* ACD1141 in the consortia with yeast YSC35 utilized more lactate than *Megasphaera elsdenii* ACD1141 alone culture and had only 7.3 mM residual lactate. This example showed that yeast can improve lactate utilization of a more oxygen tolerant *Megasphaera elsdenii* ACD1141 strain in the consortia upon oxygen exposure.

TABLE 9

| Residual lactate concentration in culture supernatants (mM) of Example 14 | | | |
|---|---|---|---|
| Strains | Set1 | Set2 | Average |
| Me (1141) | 17.57 | 19.26 | 18.42 |
| Me + YSC35 | 6.90 | 7.60 | 7.25 |
| YSC35 | 91.30 | 90.02 | 90.66 |
| Me anaerobic | 0.00 | 0.00 | 0.00 |
| Blank | 95.94 | 96.55 | 96.24 |

Example 15: Yeast Improved Lactate Utilization of Another *Megasphaera elsdenii* Strain Upon Oxygen Exposure Under "Shelf Life" Condition This example demonstrates a *Saccharomyces cerevisiae* strain YSC35 for improving lactate utilization of another *Megasphaera elsdenii* ACD1141 upon oxygen exposure under so called "shelf life" condition (RCM medium, pH 6.8, room temperature, air exposure for long periods of time such as 48 hours).

*Megasphaera elsdenii* ACD1141 is a more oxygen tolerant *Megasphaera elsdenii* strain. *Megasphaera elsdenii* ACD1141 and the *Saccharomyces cerevisiae* strain YSC35 were grown and treated as described in Example 11. After 48 hours of incubation at room temperature with air exposure, cells were inoculated into rumen fluid based media with 10 g/L DL-lactate at 1:3× fold dilution. The cells were recovered in the lactate containing medium anaerobically at 39° C. for 6 hours, then centrifuged at 3220 g for 10 minutes. Supernatants were filtered through 0.2 µm 96-well filter plate (PALL 8119) and loaded on HPLC for lactate measurement. Data in Table 10 below showed that *Megasphaera elsdenii* ACD1141 retained the ability to utilize only a small fraction of lactate under this assay condition, whereas *Megasphaera elsdenii* ACD1141 in the consortia with *Saccharomyces cerevisiae* strain YSC35 had significantly improved lactate utilization (17.6 mM residual lactate comparing to 64.1 mM residual lactate for *Megasphaera* alone).

TABLE 10

| Residual lactate concentration in culture supernatants (mM) of Example 14 | | | |
|---|---|---|---|
| Strains | Set1 | Set2 | Average |
| Me (1141) | 64.56 | 63.54 | 64.05 |
| Me + YSC35 | 18.24 | 16.89 | 17.56 |
| YSC35 | 75.08 | 75.07 | 75.08 |
| Blank | 73.76 | 74.11 | 73.93 |

Example 16: Use of Commercial *Saccharomyces cerevisiae* to Improve Lactate Utilization of *Megasphaera elsdenii* Upon Oxygen Exposure This example describes the use of several commercial *Saccharomyces cerevisiae* strains for improving lactate utilization of *Megasphaera elsdenii* ACD1141F upon oxygen exposure in the air for 18 hours.

*Megasphaera elsdenii* ACD1141F was an evolved strain of ACD1141 and was cultured in RCM media at 39° C. anaerobically. Then cells were normalized to OD2 and centrifuged @11,000×g for 1.5 min, removed supernatant and resuspended pellet in water. Commercial yeasts were rehydrated in water (100 mg per 10 ml) at 33° C. shaking at 200 rpm for 15 minutes. *Megasphaera elsdenii* and *Saccharomyces cerevisiae* cells were co-cultured in volume 1:1 in deep well plate (Corning 96 well assay block, COSTAR 3960). Single strain controls were included. In the oxygen exposure treatment, plates with cell culture were covered with sterile breathable membrane (Thermo Scientific Nunc sealing tape 241205), exposed to air. After 18 hours incubation at room temperature, cells were inoculated into IRFL media with 10 g/L DL-lactate at 1:3× fold dilution ratio. The cells were recovered in IRFL anaerobically at 39° C. for 6 hours, then centrifuged at 3220 g for 10 minutes. Supernatant were filtered through 0.2 um (PALL 8119) and loaded on HPLC for lactate measurement.

As shown in the Table 11 below, lactate utilization of *Megasphaera elsdenii* 1141F was significantly improved in consortia with any one of the commercial *Saccharomyces cerevisiae* strains after oxygen exposure at room temperature for 18 hours. The two Zenith yeasts (SC2 and SC3) showed the most improvement, and the two Ethanol yeasts (SC1 and SC10) showed the least improvement. All yeast only cultures did not utilize lactate significantly under the assay condition.

TABLE 11

Residual lactate concentration in culture supernatants (mM) of Example 16

| Strains | *Saccharomyces cerevisiae* | Producer | Residual Lactate, mM |
|---|---|---|---|
| Me(1141F) | None | | 76.49 |
| Me + SC1 | Ethanol Red | LeSaffre | 51.487 |
| Me + SC2 | Zenith thermostable yeast | AB Mauri | 41.977 |
| Me + SC3 | Zenith yeast concentrate | AB Mauri | 43.896 |
| Me + SC8 | Instant Yeast HS 2141 | AB Mauri | 48.382 |
| Me + SC9 | Instant Yeast 2174 | AB Mauri | 45.408 |
| Me + SC10 | Summit Ethanol dry yeast | AB Mauri | 56.828 |
| SC1 | Ethanol Red | LeSaffre | 75.995 |
| SC2 | Zenith thermostable yeast | AB Mauri | 72.792 |
| SC3 | Zenith yeast concentrate | AB Mauri | 73.525 |
| SC8 | Instant Yeast HS 2141 | AB Mauri | 73.559 |
| SC9 | Instant Yeast 2174 | AB Mauri | 73.605 |
| SC10 | Summit Ethanol dry yeast | AB Mauri | 72.969 |
| Me – Anaerobic | None | | 32.916 |
| Blank | None | | 75.143 |

Example 17: Beneficial Effect of Yeast on Improving Viability of *Megasphaera elsdenii* when Top Dressed on Feed This Example describes the use of the commercial *Saccharomyces cerevisiae* SC3 (Zenith yeast concentrate, AB Mauri) for improving viability of freeze dried *Megasphaera elsdenii* ACD1265F when top dressed on feed.

*Megasphaera elsdenii* ACD1265F was an evolved strain of ACD1265 and was cultured in RCM media at 39° C. anaerobically. Freeze dried ACD1265F was prepared and used in the feed study with the DFM top dressed on cattle feed, which consists of 70% corn, 15% silage, 10% hay and 5% supplement. The DFM (1 g *Megasphaera elsdenii* ACD1265F with or without 500 mg yeast *Saccharomyces cerevisiae* SC3) was rehydrated in a 10 ml RCM2 solution containing 2.4% yeast extract for about 15 min. 1 ml of rehydrated DFM was added directly on top of 10 g autoclaved feed mixture in a 250 ml flask. The open flask was put in an incubator at 30° C., 60% humidity for 0, 1, or 2 hours. After feed exposure, the DFM was extracted and dilutions were plated on RCM plates with 12.5 μg/ml Tebuconazole in duplicates in anaerobic chamber. Plates were incubated for 2 days at 39° C. anaerobically and colonies were counted. The viable counts of *Megasphaera elsdenii* ACD1265F after top dressed on cattle feed with or without *Saccharomyces cerevisiae* SC3 was shown in Table 12. At TO, the extracted *Megasphaera elsdenii* 1265F counts were similar with or without yeast.

TABLE 12

Viable counts (cfu/g) of *Megasphaera elsdenii* ACD1265F after top dressed on cattle feed with or without *Saccharomyces cerevisiae* SC3

| DFM | 0 hr | 1 hr | 2 hr |
|---|---|---|---|
| 1265F | 2.5E+9 | 1.4E+8 | 6.5E+7 |
| 1265F + SC3 | 3.5E+9 | 8.4E+8 | 3.2E+8 |

After 1 or 2 hours top dressed on feed, the extracted *Megasphaera elsdenii* 1265F counts were 5 or 6 times higher in the DFM containing yeast than the DFM without yeast. This showed the beneficial effect of yeast on improving viability of *Megasphaera elsdenii* when top dressed on cattle feed.

Example 18: Beneficial Effect of Yeast on Improving Viability of *Megasphaera elsdenii* when Mixed in Feed This Example describes the use of the commercial *Saccharomyces cerevisiae* SC3 (Zenith yeast concentrate, AB Mauri) for improving viability of freeze dried *Megasphaera elsdenii* ACD1141F or ACD1265F when mixed in feed.

Freeze dried ACD1141F and 1265F were prepared and rehydrated with or without *Saccharomyces cerevisiae* SC3 as described in Example 17. 1 ml rehydrated DFM was added into 10 g autoclaved feed mixture in a 250 ml flask, mix by shaking for 30 sec. The flask was stored with cap open in an incubator at 30° C., 60% humidity for 0 or 2 hours. No feed controls were done in the same way except no feed mixture was added in the flask. After feed exposure, the DFM was extracted and dilutions were plated on RCM plates with 12.5 ug/ml Tebuconazole in duplicates in anaerobic chamber. Plates were incubated for 2 days at 39° C. anaerobically and colonies were counted. The viable counts of 1141F and 1265F were similar at TO with or without feed exposure. This showed that the efficiency for extracting *Megasphaera* from the feed was more than 50%. After the 2 hr mixed in feed, the counts of *Megasphaera* without yeast were barely detectable (1~3E+4 cfu/g). The counts of *Megasphaera* in the presence of yeast were 1-2 logs higher as shown in Table 13.

TABLE 13

Viable counts (cfu/g) of *Megasphaera elsdenii* ACD 1141F and ACD 1265F after mixed in cattle feed with or without *Saccharomyces cerevisiae* SC3

| | Feed exposure | 1141F | 1265F |
|---|---|---|---|
| T0 | No | 4.2E+9 | 4.7E+9 |
| T0 | Yes | 2.8E+9 | 2.3E+9 |
| T2 without yeast | Yes | ~3E+4 | ~1E+4 |
| T2 with yeast | Yes | 2.4E+5 | 2.5E+6 |

In summary, this Example demonstrated the beneficial effect of yeast for improving viability of *Megasphaera elsdenii* when mixed in feed.

Example 19: Beneficial Effect of Yeast on Improving Function of *Megasphaera elsdenii* when Mixed in Feed This Example describes the use of the commercial *Saccharomyces cerevisiae* SC3 (Zenith yeast concentrate, AB Mauri) for improving lactate utilization function of freeze dried *Megasphaera elsdenii* ACD1141F or ACD1265F when mixed in feed.

In the above feed test described in Example 18, feed exposed cells were extracted inside anaerobic chamber with 100 ml RCM media and further diluted in rumen fluid-based media (as described in Example 1) containing 10 g/L lactate with final *Megasphaera* concentration 0.1 g/L. Cells were sealed by aluminum foil cover and incubated at 39° C. anaerobically overnight. After ~20 hr incubation, the residual lactate was quantified by HPLC and data shown in Table 14. The medium blank without DFM had the initial amount of lactate.

TABLE 14

Residual lactate (mM) after overnight recovering of feed
exposed *Megasphaera elsdenii* ACD 1141F and ACD 1265F
with or without *Saccharomyces cerevisiae* SC3

| | Feed exposure | 1141F | 1265F | Medium blank |
|---|---|---|---|---|
| T0 | No | 1.29 | 1.01 | 90.01 |
| T0 | Yes | 0.90 | 1.08 | |
| T2 without yeast | Yes | 93.77 | 96.96 | |
| T2 with yeast | Yes | 0.78 | 0.75 | |

The T0 samples with or without feed extraction consumed all the lactate in the medium. The 2-hour feed exposed samples also consumed all the lactate in the presence of yeast. However, in the absence of yeast, the 2-hour feed exposed samples did not consume any lactate. This suggested that yeast improved the lactate utilization function of *Megasphaera* after the feed exposure. This Example showed benefit of adding yeast to *Megasphaera* in the DFM when mixed in feed with air exposure.

Example 20: Soluble Polysaccharides as Excipients
to Improve Viability of *Megasphaera elsdenii* when
Mixed in Feed This example describes the use of soluble polysaccharides to further improve viability of freeze dried blend of *Megasphaera elsdenii* ACD1141F and ACD1265F when mixed in feed together with *Saccharomyces cerevisiae* SC3 for longer period of time (4 hours).

The freeze dried *Megasphaera elsdenii* ACD1141F and ACD1265F were blended as mixture and the *Megasphaera elsdenii* blend was used in this feed stability test. DFM containing 1 g of *Megasphaera elsdenii* blend and 500 mg of *Saccharomyces cerevisiae* SC3 was rehydrated in 10 ml RCM2 solution with additional 20 mg of soluble polysaccharides (0.2%) except no polysaccharide was added in the control. 1 ml rehydrated DFM was added into 10 g autoclaved feed mixture in a 250 ml flask, mix by shaking for 30 sec. The flask was stored with cap open in an incubator at 30° C., 60% humidity for 0, 2 or 4 hours. After feed exposure, the DFM was extracted and dilutions were plated on RCM plates with 12.5 ug/ml Tebuconazole in duplicates in anaerobic chamber. Plates were incubated for 2 days at 39° C. anaerobically and colonies were counted.

Figure 5:
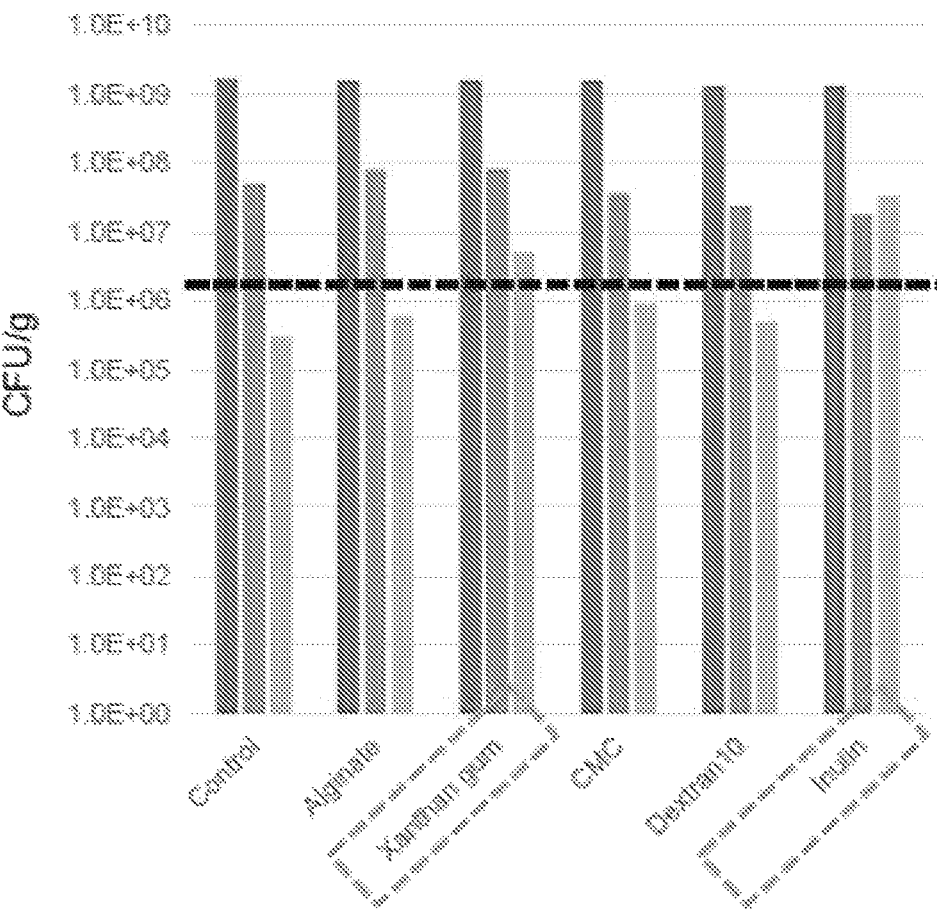
FIG. 5 depicts a bar graph showing *Megasphaera elsdenii* viability counts (CFU/g) after four hours when mixed with feed together with *Saccharomyces cerevisiae* SC3 and soluble polysaccharides.

The *Megasphaera* viability counts of the feed extraction was shown in FIG. 5. The initial *Megasphaera* counts were ~1E+9 cfu/g. After 4 hours mixed in feed, the no polysaccharide excipient control had ~5E+5 cfu/g. The excipients xanthan gum or inulin showed increased *Megasphaera* viability about 1-2 logs. The other excipients tested (alginate, carboxyl methyl cellulose CMC, dextran) did not show significant improvement of *Megasphaera* viability.

Example 21: Soluble Polysaccharides as Excipients
to Improve Lactate Utilization of *Megasphaera
elsdenii* when Mixed in Feed This example describes the use of soluble polysaccharides to further improve lactate utilization of freeze dried blend of *Megasphaera elsdenii* ACD1141F and ACD1265F when mixed in feed together with *Saccharomyces cerevisiae* SC3 for longer period of time (4 hours).

Figure 6:
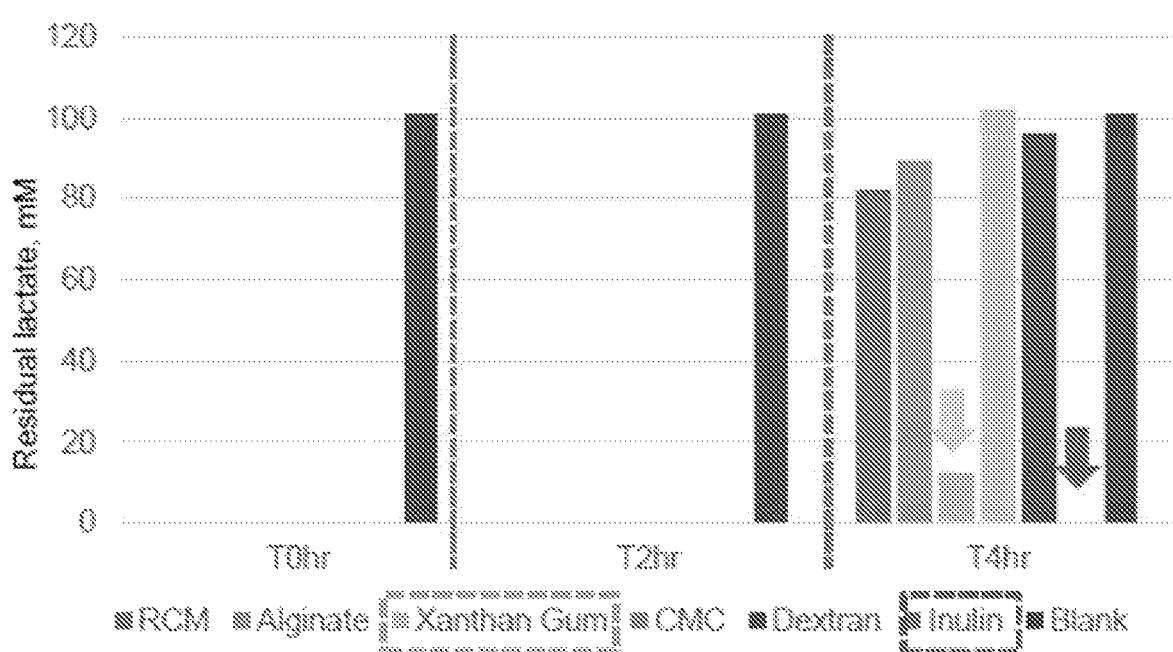
FIG. 6 depicts a bar graph showing lactate utilization of *Megasphaera elsdenii* after 4 hours mixed in feed with soluble polysaccharides.

In the above feed test with soluble excipients as described in Example 20, feed exposed cells were extracted inside anaerobic chamber with 100 ml RCM media and further diluted in rumen fluid based media (described in Example 1) containing 10 g/L lactate with final *Megasphaera* concentration 0.1 g/L. Cells were sealed by aluminum foil cover and incubated at 39° C. anaerobically overnight. After ~20 hr incubation, the residual lactate was quantified by HPLC and data shown in FIG. 6. The medium blank without DFM had the initial amount of lactate.

The T0 and T2 hour DFM samples with or without excipient consumed all the lactate in the medium. The T4 hour feed exposed samples consumed most or all the lactate in the presence of xanthan gum or inulin. The samples with no excipient or with other excipients (alginate, carboxyl methyl cellulose CMC, dextran) did not consume significant amount of lactate. This is consistent with the viability data in Example 20. The excipients xanthan gum or inulin improved lactate utilization of *Megasphaera* after 4 hours mixed in feed. The other excipients tested (alginate, carboxyl methyl cellulose CMC, dextran) did not show significant improvement of *Megasphaera* lactate utilization function.

Example 22: Insoluble Polysaccharides as
Excipients to Improve Viability of *Megasphaera
elsdenii* when Mixed in Feed This example describes the use of insoluble polysaccharides to further improve viability of freeze dried blend of *Megasphaera elsdenii* ACD1141F and ACD1265F when mixed in feed together with *Saccharomyces cerevisiae* SC3 for longer period of time (4 hours).

The *Megasphaera elsdenii* blend containing freeze dried ACD1141F and ACD1265F mixture was used in this feed stability test. DFM containing 1 g of *Megasphaera elsdenii* blend and 500 mg of *Saccharomyces cerevisiae* SC3 was rehydrated in 10 ml RCM2 solution with additional 50 mg of insoluble polysaccharides (0.5%) Argo corn starch or microcrystalline cellulose. 0.5% Benco inulin was used as the positive control. 1 ml rehydrated DFM was added into 10 g autoclaved feed mixture in a 250 ml flask, mix by shaking for 30 sec. The flask was stored with cap open in an incubator at 30° C., 60% humidity for 0, 2 or 4 hours. After feed exposure, the DFM was extracted and dilutions were plated on RCM plates with 12.5 ug/ml Tebuconazole in duplicates in anaerobic chamber. Plates were incubated for 2 days at 39° C. anaerobically and colonies were counted. The *Megasphaera* viability counts of the feed extraction was shown in Table 15.

TABLE 15

Viable counts (cfu/g) of *Megasphaera elsdenii* after mixed
in cattle feed with 0.5% soluble or insoluble excipients.

|  | inulin | starch | cellulose |
|---|---|---|---|
| T0 | 2.0E+9 | 1.6E+9 | 1.6E+9 |
| T2 h | 5.7E+7 | 8.9E+7 | 6.4E+7 |
| T4 h | 1.0E+7 | 3.8E+7 | 1.3E+7 |

The initial *Megasphaera* counts were ~1E+9 cfu/g. After 4 hours mixed in feed, the samples with insoluble excipients (starch or cellulose) showed similar *Megasphaera* viability as that of the positive control sample with inulin. This suggested that insoluble polysaccharides starch or cellulose could also improve viability of *Megasphaera* when mixed in feed as inulin did.

Example 23: Insoluble Polysaccharides as Excipients to Improve Lactate Utilization of *Megasphaera elsdenii* when Mixed in Feed This Example describes the use of insoluble polysaccharides to further improve lactate utilization of freeze dried blend of *Megasphaera elsdenii* ACD1141F and ACD1265F when mixed in feed together with *Saccharomyces cerevisiae* SC3 for longer period of time (4 hours).

In the above feed test with insoluble excipients described in Example 22, feed exposed cells were extracted inside anaerobic chamber with 100 ml RCM media and further diluted in rumen fluid based media (described in example 1) containing 10 g/L lactate with final *Megasphaera* concentration 0.1 g/L. Cells were sealed by aluminum foil cover and incubated at 39° C. anaerobically overnight. After ~20 hr incubation, the residual lactate was quantified by HPLC. The medium blank had the initial amount of lactate. All the samples with 0.5% insoluble polysaccharides (starch or cellulose) as excipients consumed all lactate as the positive control containing 0.5% soluble inulin. No residual lactate was present in the 4 hour feed exposed samples as well as the 2 hour or T0 feed exposed samples. Consistent with the viability data in Example 22, insoluble polysaccharides starch or cellulose improved lactate utilization of *Megasphaera* as inulin did.

```
SEQUENCES
>ACD1265 16S rRNA
                                    (SEQ ID NO: 1)
CATGGAGAGTTTGATCCTGGCTCAGGACGAACGCT

GGCGGCGTGCTTAACACATGCAAGTCGAACGAGAA

GAGATGAGAAGCTTGCTTCTTATTGATTCGAGTGG

CAAACGGGTGAGTAACGCGTAAGCAACCTGCCCTT

CAGATGGGGACAACAGCTGGAAACGGCTGCTAATA

CCGAATACGTTCTTTTTGTCGCATGGCAGAGAGAA

GAAAGGGAGGCTCTTCGGAGCTTTCGCTGAAGGAG

GGGCTTGCGTCTGATTAGCTAGTTGGAGGGGTAAC

GGCCCACCAAGGCGACGATCAGTAGCCGGTCTGAG

AGGATGAACGGCCACATTGGGACTGAGACACGGCC

CAGACTCCTACGGGAGGCAGCAGTGGGGAATCTTC
```

```
-continued
CGCAATGGACGAAAGTCTGACGGAGCAACGCCGCG

TGAACGATGACGGCCTTCGGGTTGTAAAGTTCTGT

TATACGGGACGAATGGCGTAGCGGTCAATACCCGT

TACGAGTGACGGTACCGTAAGAGAAAGCCACGGCT

AACTACGTGCCAGCAGCCGCGGTAATACGTAGGTG

GCAAGCGTTGTCCGGAATTATTGGGCGTAAAGGGC

GCGCAGGCGGCGTCGTAAGTCGGTCTTAAAAGTGC

GGGGCTTAACCCCGTGAGGGGACCGAAACTGCGAT

GCTAGAGTATCGGAGAGGAAAGCGGAATTCCTAGT

GTAGCGGTGAAATGCGTAGATATTAGGAGGAACAC

CAGTGGCGAAAGCGGCTTTCTGGACGACAACTGAC

GCTGAGGCGCGAAAGCCAGGGGAGCAAACGGGATT

AGATACCCCGGTAGTCCTGGCCGTAAACGATGGAT

ACTAGGTGTAGGAGGTATCGACCCCTTCTGTGCCG

GAGTTAACGCAATAAGTATCCCGCCTGGGGAGTAC

GGCCGCAAGGCTGAAACTCAAAGGAATTGACGGGG

GCCCGCACAAGCGGTGGAGTATGTGGTTTAATTCG

ACGCAACGCGAAGAACCTTACCAAGCCTTGACATT

GATTGCTATGGGTAGA

>ACD1096 16S rRNA
                                    (SEQ ID NO: 2)
CGAGTGGCAAACGGGTGAGTAACGCGTAAGCAACC

TGCCCTTCAGATGGGGACAACAGCTGGAAACGGCT

GCTAATACCGAATACGTTCTTTTTGTCGCATGGCA

GAGGGAAGAAAGGGAGGCTCTTCGGAGCTTTCGCT

GAAGGAGGGGCTTGCGTCTGATTAGCTAGTTGGAG

GGGTAACGGCCCACCAAGGCGACGATCAGTAGCCG

GTCTGAGAGGATGAACGGCCACATTGGGACTGAGA

CACGGCCCAGACTCCTACGGGAGGCAGCAGTGGGG

AATCTTCCGCAATGGACGAAAGTCTGACGGAGCAA

CGCCGCGTGAACGATGACGGCCTTCGGGTTGTAAA

GTTCTGTTATACGGGACGAATGGCGTAGCGGTCAA

TACCCGTTACGAGTGACGGTACCGTAAGAGAAAGC

CACGGCTAACTACGTGCCAGCAGCCGCGGTAATAC

GTAGGTGGCAAGCGTTGTCCGGAATTATTGGGCGT

AAAGGGCGCGCAGGCGGCGTCGTAAGTCGGTCTTA

AAAGTGCGGGGCTTAACCCCGTGAGGGGACCGAAA

CTGCGATGCTAGAGTATCGGAGAGGAAAGCGGAAT

TCCTAGTGTAGCGGTGAAATGCGTAGATATTAGGA

GGAACACCAGTGGCGAAAGCGGCTTTCTGGACGAC

AACTGACGCTGAGGCGCGAAAGCCAGGGGAGCAAA

CGGGATTAGATACCCCGGTAGTCCTGGCCGTAAAC
```

-continued

```
GATGGATACTAGGTGTAGGAGGTATCGACCCCTTC

TGTGCCGGAGTTAACGCAATAAGTATCCCGCCTGG

GGAGTACGGCCGCAAGGCTGAAACTCAAAGGAATT

GACGGGGGCCCGCACAAGCGGTGGAGTATGTGGTT

TAATTCGACGCAACGCGAAGAACCTTACCAAGCCT

TGACATTGATTGCTATGGATAGAGATATCCAGTTC

CTCTTCGGAGGACAAGAAAACAGGTGGTGCACGGC

TGTCGTCAGCTCGTGTCGTGAGATGTTGGGTTAAG

TCCCGCAACGAGCGCAACCCCTATCTTCTGTTACC

AGCGGTTCGGCCGGGACTCAGGAGAGACTGCCGC

AGACAATGCGGAGGAAGGCGGGGATGACGTCAAGT

CATCATGCCCCTTATGGCTTGGGCTACACACGTAC

TACAATGGCTCTTAATAGAGGGAAGCGAAGGAGCG

ATCCGGAGCAAACCCCAAAAACAGAGTCCCAGTTC

GGATTGCAGGCTGCAACTCGCCTGCATGAAGCAGG

AATCGCTAGTAATCGCAGGTCAGCATACTGCGGTG

AATACGTTCCCGGGCCTTGTACACACCGCCCGTCA

CACCACGAAAGTCATTCACACCCGAAGCCGGTGAG

GTAACCTTTTGGAGCCAGCCGTCGAAGGTGGGGGC

GATGATTGGGGTGAAGTCGTAACAAGGTAGCCGTA

TCGGAAGGTGCGGCTGGATCACCTCCTTT
```

>ACD1141 16S rRNA
                              (SEQ ID NO: 3)
```
CATGGAGAGTTTGATCCTGGCTCAGGACGAACGCT

GGCGGCGTGCTTAACACATGCAAGTCGAACGAGAA

GAGATGAGAAGCTTGCTTCTTATTGATTCGAGTGG

CAAACGGGTGAGTAACGCGTAAGCAACCTGCCCTT

CAGATGGGGACAACAGCTGGAAACGGCTGCTAATA

CCGAATACGTTCTTTTTGTCGCATGGCAGAGGGAA

GAAAGGGAGGCTCTTCGGAGCTTTCGCTGAAGGAG

GGGCTTGCGTCTGATTAGCTAGTTGGAGGGGTAAC

GGCCCACCAAGGCGACGATCAGTAGCCGGTCTGAG

AGGATGAACGGCCACATTGGGACTGAGACACGGCC

CAGACTCCTACGGGAGGCAGCAGTGGGGAATCTTC

CGCAATGGACGAAAGTCTGACGGAGCAACGCCGCG

TGAACGATGACGGCCTTCGGGTTGTAAAGTTCTGT

TATACGGGACGAATGGCGTAGCGGTCAATACCCGT

TACGAGTGACGGTACCGTAAGAGAAAGCCACGGCT

AACTACGTGCCAGCAGCCGCGGTAATACGTAGGTG

GCAAGCGTTGTCCGGAATTATTGGGCGTAAAGGGC

GCGCAGGCGGCGTCGTAAGTCGGTCTTAAAAGTGC
```

```
GGGGCTTAACCCCGTGAGGGGACCGAAACTGCGAT

GCTAGAGTATCGGAGAGGAAAGCGGAATTCCTAGT

GTAGCGGTGAAATGCGTAGATATTAGGAGGAACAC

CAGTGGCGAAAGCGGCTTTCTGGACGACAACTGAC

GCTGAGGCGCGAAAGCCAGGGGAGCAAACGGGATT

AGATACCCCGGTAGTCCTGGCCGTAAACGATGGAT

ACTAGGTGTAGGAGGTATCGACCCCTTCTGTGCCG

GAGTTAACGCAATAAGTATCCCGCCTGGGGAGTAC

GGCCGCAAGGCTGAAACTCAAAGGAATTGACGGGG

GCCCGCACAAGCGGTGGAGTATGTGGTTTAATTCG

ACGCAACGCGAAGAACCTTACCAAGCCTTGACATT

GAT
```

>AG8660040_00732 Transcriptional
regulator PerR (ACD1009)
                              (SEQ ID NO: 4)
```
ATGGAAATTGCTGAAGTTTTGCGAAAAAACGGCTA

TAAAGTAACTCCGCAGCGCCTGGCTGTGTACGAAG

CCATCAATCACAATCCGACGCATCCCAATGCCGAG

GCGATTTACAAGATATTACAGCCCAATTATCCGTC

TATGAGTCTGGCTACGGTCTACAAGACGATGGAAA

TCTTTGCCAAAATTGGCGTTGTCCAGGTCTTGCAG

TGTGCAGAAGATGCCCATCGCTATGATTATAATAC

AACTCCCCATGCCCATATTCGTTGCGAAAAATGCA

ACCGCGTCATCGATATCGACATGGACCAGGAGGGA

TTGCGTCAGCAGGCGGCTGAACAGAGCGGCTTCGT

CGTCAACGGCGTCAGTATTTCGTTTGTCGGGATTT

GCCCGGAATGTCGGGAAAAATCGTAA
```

>AG8660040_00732 Transcriptional
regulator PerR (ACD1009)
                              (SEQ ID NO: 5)
```
MEIAEVLRKNGYKVTPQRLAVYEAINHNPTHPNAE

AIYKILQPNYPSMSLATVYKTMEIFAKIGVVQVLQ

CAEDAHRYDYNTTPHAHIRCEKCNRVIDIDMDQEG

LRQQAAEQSGFVVNGVSISFVGICPECREKS
```

>AG8660041_00415 Transcriptional
regulator PerR (ACD1265)
                              (SEQ ID NO: 6)
```
MEIAEVLRKNGYKVTPQRLAVYEAINHNPTHPNAE

AIYKILQPNYPSMSLATVYKTMEIFAKIGVVQVLQ

CAEDAHRYDYNTTPHAHIRCEKCNRVIDIDMDQEG

LRQQAAEQSGFVVNGVSISFVGIFPECREKS
```

-continued

>AG8660041_00415 Transcriptional regulator PerR (ACD1265)

(SEQ ID NO: 7)

ATGGAAATTGCTGAAGTTTTGCGAAAAAACGGCTA

TAAAGTAACTCCGCAGCGCCTGGCTGTGTACGAAG

CCATCAATCACAATCCGACGCATCCCAATGCCGAG

GCGATTTACAAGATATTACAGCCCAATTATCCGTC

TATGAGTCTGGCTACGGTCTACAAGACGATGGAAA

-continued

TCTTTGCCAAAATTGGCGTTGTCCAGGTCTTGCAG

TGTGCAGAAGATGCCCATCGCTATGATTATAATAC

AACTCCCCATGCCCATATTCGTTGCGAAAAATGCA

ACCGCGTCATCGATATCGACATGGACCAGGAGGGA

TTGCGTCAGCAGGCGGCTGAACAGAGCGGCTTCGT

CGTCAACGGCGTCAGTATTTCGTTTGTCGGGATTT

TCCCGGAATGTCGGGAAAAATCGTAA

---

We claim:

1. A feed additive composition comprising a direct fed microbial (DFM) comprising at least one biologically pure strain of an oxygen tolerant *Megasphaera elsdenii* (*M. elsdenii*), wherein the oxygen tolerant *M. elsdenii* comprises at least one mutation (a) in a gene encoding a transcriptional regulator PerR comprising SEQ ID NO: 4; or (b) immediately upstream of a gene encoding the transcriptional regulator PerR.

2. The feed additive composition of claim 1, wherein the at least one mutation is (a) a nucleotide substitution resulting in an amino acid change in a transcriptional regulator PerR protein; and/or (b) an insertion of a nucleotide resulting in a frameshift mutation.

3. The feed additive composition of claim 2, wherein the nucleotide substitution is at a nucleotide position selected from the group consisting of 386, 155, 253, −99, and −125 corresponding to a gene encoded by the polynucleotide sequence of SEQ ID NO: 4.

4. The feed additive composition of claim 3, wherein the nucleotide substitution comprises G386T, C155T, C253T, T-99C, or G-125A.

5. The feed additive composition of claim 4, wherein the amino acid change comprises C129F, T52M, or H85Y relative to the polypeptide encoded by SEQ ID NO: 5.

6. The feed additive composition of claim 5, wherein the PerR protein comprises the polypeptide encoded by SEQ ID NO: 6.

7. The feed additive composition of claim 2, wherein the nucleotide insertion is at a nucleotide position selected from the group consisting of 30, 277, and 64 corresponding to SEQ ID NO: 4.

8. The feed additive composition of claim 7, wherein the insertion is an A at position 30, an A at position 277, or a G at position 64.

9. The feed additive composition of claim 1, comprising one or more of (a) an *M. elsdenii* strain having a 16S ribosomal RNA sequence displaying at least 97.0% sequence similarity to a 16S ribosomal DNA sequence of an *M. elsdenii* strain ACD1265 deposited at Westerdijk Fungal Biodiversity Institute (WFDI) under number CBS 146328; (b) an *M. elsdenii* strain having a 16S ribosomal RNA sequence displaying at least 97.0% sequence similarity to a 16S ribosomal DNA sequence of an *M. elsdenii* strain ACD1141 deposited at WFDI under number CBS 146325; (c) an *M. elsdenii* strain having a 16S ribosomal RNA sequence displaying at least 97.0% sequence similarity to a 16S ribosomal DNA sequence of an *M. elsdenii* strain ACD1141E deposited at WFDI under number CBS 146326;

(d) an *M. elsdenii* strain having a 16S ribosomal RNA sequence displaying at least 97.0% sequence similarity to a 16S ribosomal DNA sequence of an *M. elsdenii* strain ACD1141F deposited at WFDI under number CBS 146327;

(e) an *M. elsdenii* strain having a 16S ribosomal RNA sequence displaying at least 97.0% sequence similarity to a 16S ribosomal DNA sequence of an *M. elsdenii* strain ACD1265E deposited at WFDI under number CBS 146329;

and/or (f) an *M. elsdenii* strain having a 16S ribosomal RNA sequence displaying at least 97.0% sequence similarity to a 16S ribosomal DNA sequence of an *M. elsdenii* strain ACD1265F deposited at WFDI under number CBS 146330.

10. The feed additive composition of claim 1, wherein the oxygen tolerant *M. elsdenii* remains viable after at least about 7-12 days of exposure to oxygen.

11. The feed additive composition of claim 10, wherein at least about $5.73 \times 10^2$ to about $1.16 \times 10^8$ cfu/mL of the *M. elsdenii* remains viable after 7-12 days of exposure to oxygen.

12. The feed additive composition of claim 1, wherein the oxygen tolerant *M. elsdenii* remains viable after at least 10 days after exposure to oxygen.

13. The feed additive composition of claim 1, further comprising at least one yeast strain and/or yeast extract.

14. A method for treating, preventing, or decreasing incidence of rumen acidosis in a ruminant animal comprising administering an effective amount of the feed additive composition of claim 1 to the animal, thereby treating, preventing, or decreasing incidence of rumen acidosis in the animal.

15. The method of claim 14, wherein said administration raises or maintains the pH of the rumen of the animal above pH 5.6.

16. The method of claim 14, wherein the ruminant animal is a cow, goat, sheep, buffalo, deer or other member of the Ruminantia suborder of mammals.

17. The method of claim 16, wherein the ruminant animal is a dairy cow or a beef cow.

\* \* \* \* \*